(12) United States Patent
Tsai et al.

(10) Patent No.: US 7,136,159 B2
(45) Date of Patent: Nov. 14, 2006

(54) EXCIMER LASER INSPECTION SYSTEM

(75) Inventors: Bin-Ming Benjamin Tsai, Saratoga, CA (US); Yung-Ho Chuang, Cupertino, CA (US); J. Joseph Armstrong, Milpitas, CA (US); David Lee Brown, Sunnyvale, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 169 days.

(21) Appl. No.: 10/096,318

(22) Filed: Mar. 12, 2002

(65) Prior Publication Data

US 2004/0095573 A1 May 20, 2004

Related U.S. Application Data

(63) Continuation-in-part of application No. 09/796,117, filed on Feb. 28, 2001, now Pat. No. 6,842,298.

(60) Provisional application No. 60/231,761, filed on Sep. 12, 2000.

(51) Int. Cl.
*G01N 21/00* (2006.01)
(52) U.S. Cl. .................................... 356/237.5
(58) Field of Classification Search .. 356/237.1–237.4; 250/548, 559.04
See application file for complete search history.

(56) References Cited

U.S. PATENT DOCUMENTS

| | | | |
|---|---|---|---|
| 1,973,066 A | 9/1934 | Hauser et al. | |
| 2,661,658 A | 12/1953 | Dyson | |
| 3,237,515 A | 3/1966 | Altman | |
| 4,106,046 A * | 8/1978 | Nathanson et al. | 257/234 |
| 4,155,630 A | 5/1979 | Ih | |
| 4,334,199 A * | 6/1982 | Ham | 372/57 |
| 4,347,001 A | 8/1982 | Levy et al. | |
| 4,511,220 A | 4/1985 | Scully | |
| 4,628,938 A | 12/1986 | Sandland et al. | |
| 4,758,088 A | 7/1988 | Doyle | |
| 4,779,966 A | 10/1988 | Friedman | |
| 4,792,695 A * | 12/1988 | Blandford | 250/559.24 |
| 4,795,244 A | 1/1989 | Uehara | |
| 4,898,471 A | 2/1990 | Stonestrom et al. | |
| 4,926,489 A | 5/1990 | Danielson et al. | |
| 4,944,593 A * | 7/1990 | Kalstroem et al. | 356/626 |
| 4,971,428 A | 11/1990 | Moskovich | |
| 4,974,094 A | 11/1990 | Morito | |
| 5,031,976 A | 7/1991 | Shafer | |
| 5,067,811 A * | 11/1991 | Ouchi | 356/121 |
| 5,089,913 A | 2/1992 | Singh et al. | |
| 5,114,238 A | 5/1992 | Sigler | |
| 5,140,459 A | 8/1992 | Sagan | |
| 5,177,559 A | 1/1993 | Batchelder et al. | |
| 5,233,460 A | 8/1993 | Partlo | |

(Continued)

FOREIGN PATENT DOCUMENTS

DE 108181 1/1900

(Continued)

OTHER PUBLICATIONS

M.R. Bartz et al., "LED Print Analyzer," IBM Technical Disclosure Bulletin, vol. 14, No. 3, Aug. 1971.

(Continued)

*Primary Examiner*—Michael P. Stafira
(74) *Attorney, Agent, or Firm*—Smyrski Law Group, A.P.C.

(57) ABSTRACT

A system and method for inspecting a specimen, such as a semiconductor wafer, including illuminating at least a portion of the specimen using an excimer source using at least one relatively intense wavelength from the source, detecting radiation received from the illuminated portion of the specimen, analyzing the detected radiation for potential defects present in the specimen portion.

44 Claims, 42 Drawing Sheets

U.S. PATENT DOCUMENTS

| | | | |
|---|---|---|---|
| 5,274,494 A | | 12/1993 | Rafanelli et al. |
| 5,303,594 A | * | 4/1994 | Kurtz et al. ............... 73/727 |
| 5,313,479 A | | 5/1994 | Florence |
| 5,323,263 A | | 6/1994 | Schoenmakers |
| 5,428,442 A | | 6/1995 | Lin et al. |
| 5,488,229 A | | 1/1996 | Elliott et al. |
| 5,515,207 A | | 5/1996 | Foo |
| 5,596,411 A | * | 1/1997 | Fanton et al. ............. 356/369 |
| 5,636,066 A | | 6/1997 | Takahashi |
| 5,644,140 A | | 7/1997 | Biedermann et al. |
| 5,668,673 A | | 9/1997 | Suenaga et al. |
| 5,717,518 A | * | 2/1998 | Shafer et al. ............. 359/357 |
| 5,729,374 A | | 3/1998 | Tiszauer et al. |
| 5,774,222 A | * | 6/1998 | Maeda et al. ............. 356/394 |
| 5,798,829 A | | 8/1998 | Vaez-Iravani |
| 5,805,334 A | | 9/1998 | Takahashi |
| 5,805,357 A | | 9/1998 | Omura |
| 5,808,797 A | | 9/1998 | Bloom et al. |
| 5,808,805 A | | 9/1998 | Takahashi |
| 5,835,275 A | | 11/1998 | Takahashi et al. |
| 5,861,997 A | | 1/1999 | Takahashi |
| 5,880,891 A | | 3/1999 | Furter |
| 5,892,579 A | | 4/1999 | Elyasaf et al. |
| 5,990,983 A | | 11/1999 | Hargis et al. |
| 5,999,310 A | | 12/1999 | Shafer et al. |
| 6,057,917 A | * | 5/2000 | Petersen et al. ........... 356/213 |
| 6,064,517 A | | 5/2000 | Chuang et al. |
| 6,082,200 A | * | 7/2000 | Aslam et al. ............... 73/774 |
| 6,132,280 A | * | 10/2000 | Tanabe et al. .............. 445/58 |
| 6,133,986 A | | 10/2000 | Johnson |
| 6,137,570 A | * | 10/2000 | Chuang et al. .......... 356/237.5 |
| 6,175,645 B1 | | 1/2001 | Elyasaf et al. |
| 6,188,710 B1 | * | 2/2001 | Besaucele et al. ........... 372/60 |
| 6,268,093 B1 | | 7/2001 | Kenan et al. |
| 6,282,309 B1 | | 8/2001 | Emery |
| 6,285,701 B1 | * | 9/2001 | Albrecht et al. ............. 372/57 |
| 6,288,780 B1 | | 9/2001 | Fairley et al. |
| 6,320,657 B1 | * | 11/2001 | Aspnes et al. ............. 356/369 |
| 6,331,885 B1 | * | 12/2001 | Nishi ......................... 355/53 |
| 6,345,065 B1 | * | 2/2002 | Kleinschmidt et al. ....... 372/57 |
| 6,426,966 B1 | * | 7/2002 | Basting et al. ............... 372/19 |
| 6,512,631 B1 | * | 1/2003 | Shafer et al. ............. 359/355 |
| 6,548,797 B1 | | 4/2003 | Ai |
| 6,566,671 B1 | * | 5/2003 | Yoshida et al. .......... 250/559.4 |
| 6,667,796 B1 | * | 12/2003 | Nishi ......................... 355/30 |
| 2001/0046247 A1 | * | 11/2001 | Hartman ..................... 372/57 |
| 2002/0196418 A1 | * | 12/2002 | Hagiwara et al. ............ 355/67 |

FOREIGN PATENT DOCUMENTS

| | | |
|---|---|---|
| DE | 3742806 | 7/1989 |
| EP | 0798585 | 10/1997 |
| GB | 2269024 | 1/1994 |
| WO | 9712226 | 4/1997 |
| WO | 9908134 | 2/1999 |

OTHER PUBLICATIONS

D.S. Goodman, "Darkfield Illuminator Attachment," IBM Technical Disclosure Bulletin, vol. 27, No. 5, Oct. 1984.

J.L.C. Sanz et al., "Automated Visual Inspection with Dark-Field Microscopy," Journal of the Optical Society of America, Nov. 1985, USA, vol. 2, No. 11, pp. 1857-1862.

Carl Zeiss Brochure, "MSM 193 Microlithography Simulation Microscope," MSM 193 device introduced 1999.

* cited by examiner

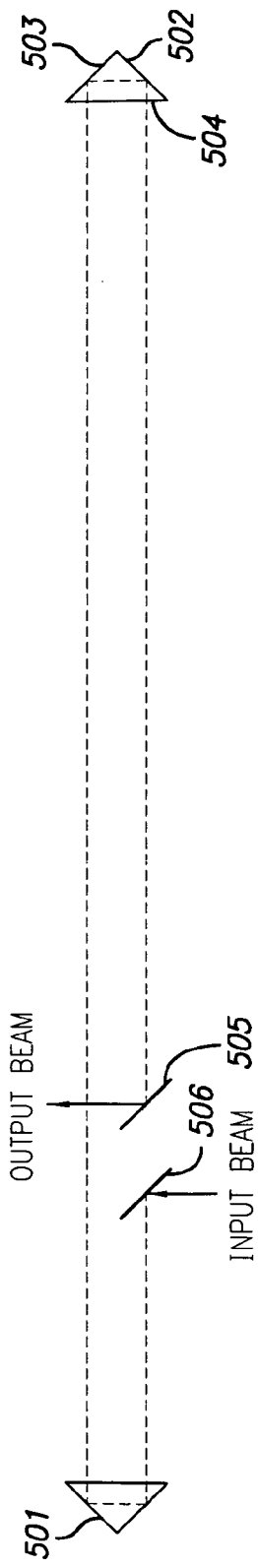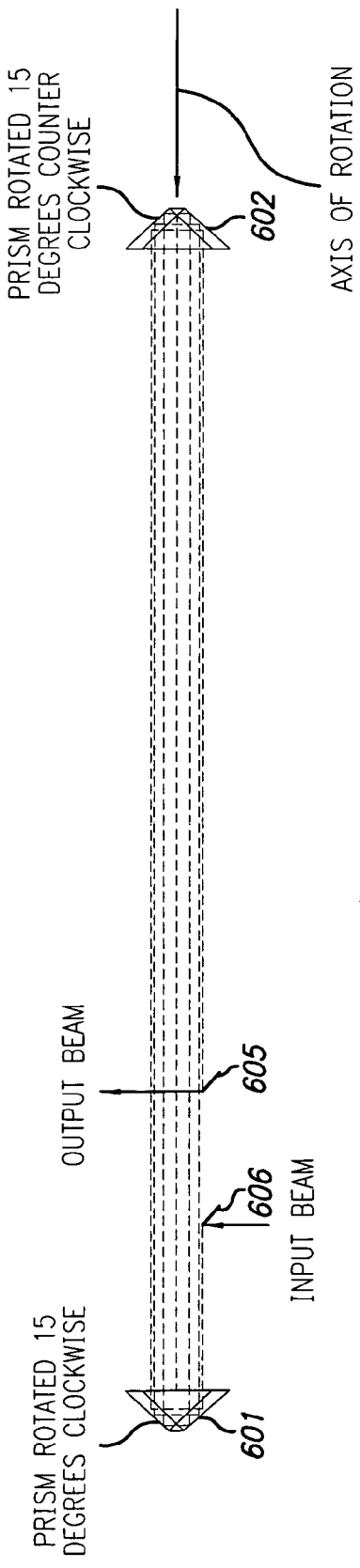
FIG. 5
FIG. 6

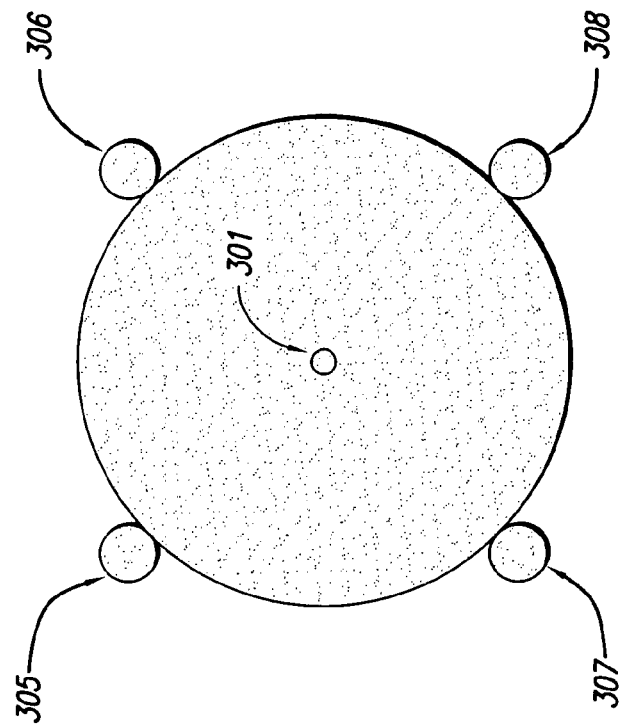
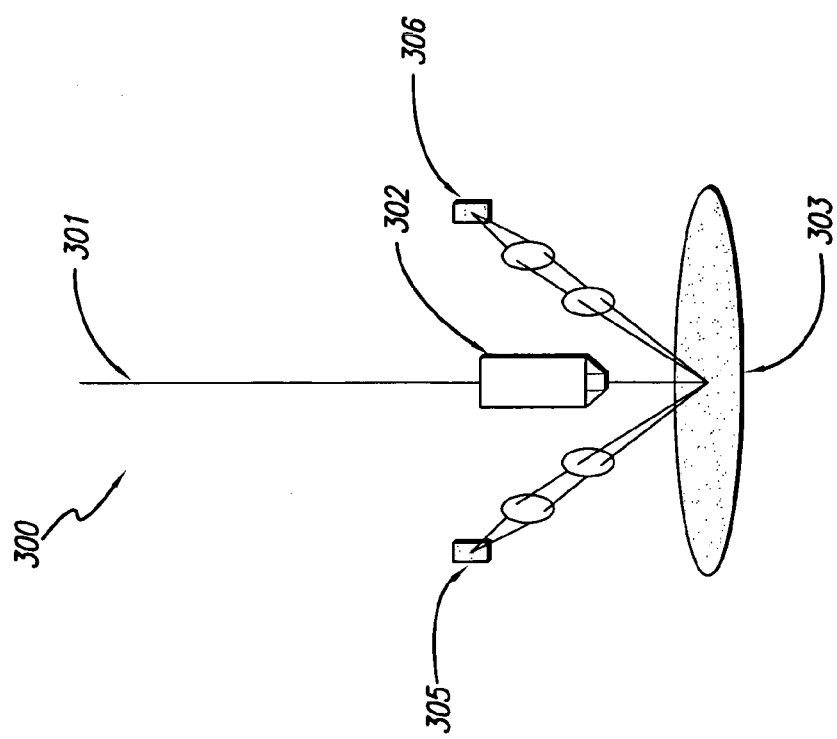
FIG. 28
FIG. 27

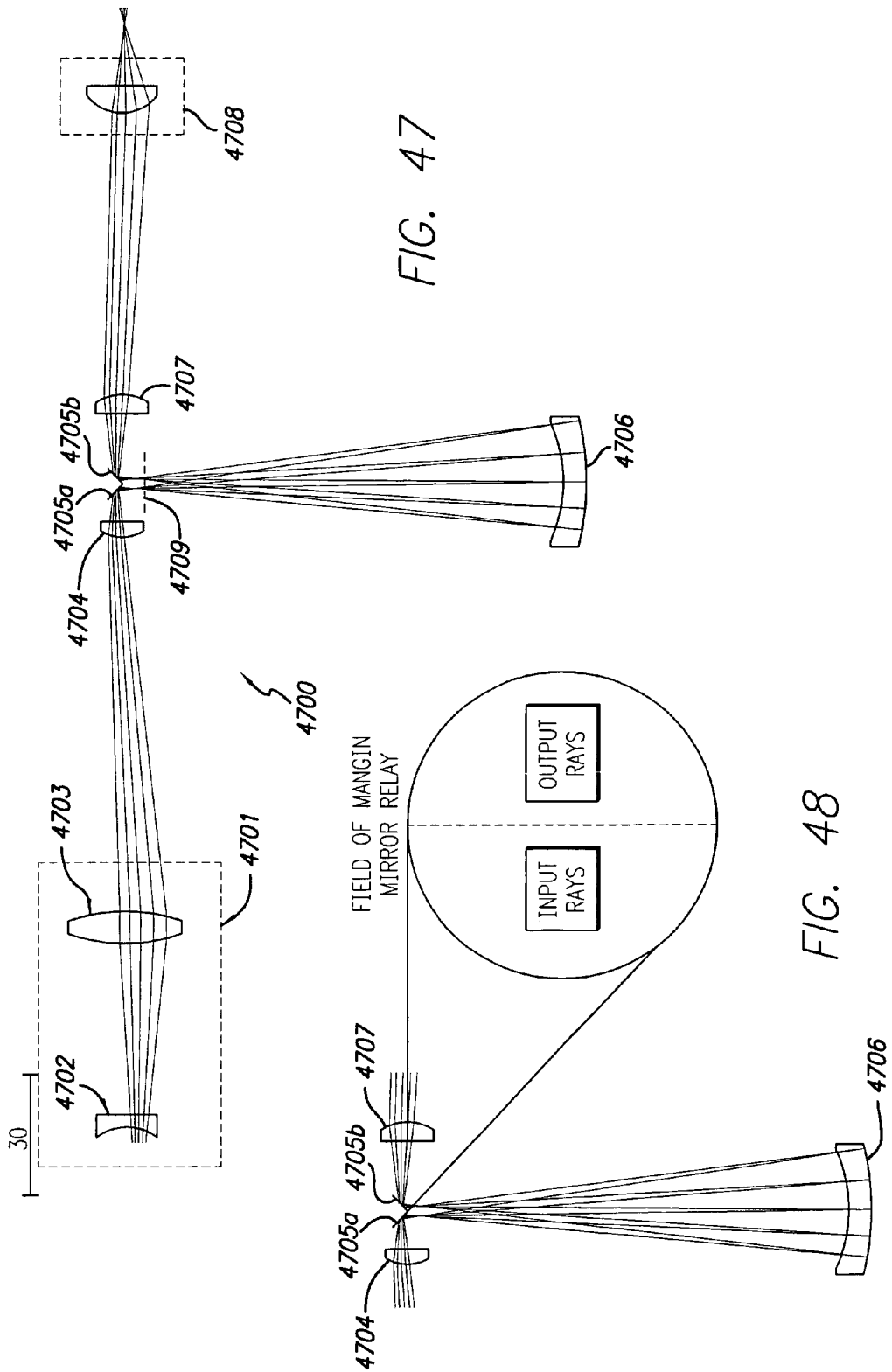

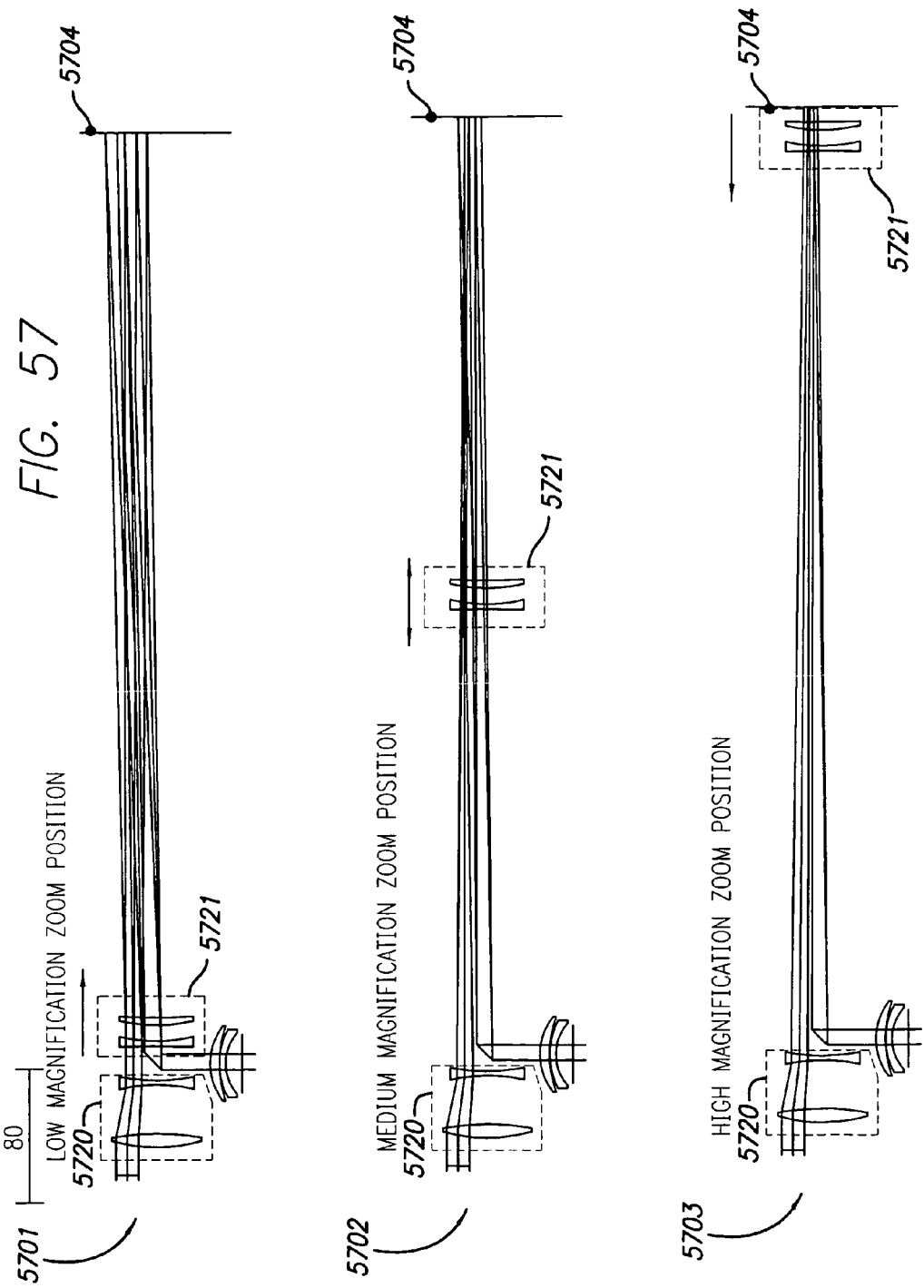

EXCIMER LASER INSPECTION SYSTEM

This application is a continuation in part of U.S. patent application Ser. No. 09/796,117, filed Feb. 28, 2001, now U.S. Pat. No. 6,842,298 entitled "Broad Band DUV/VUV Long Working Distance Catadioptric Imaging System," inventors Shafer et. al., which claims the benefit of U.S. Provisional Patent Application 60/231,761, filed Sep. 12, 2000.

BACKGROUND OF THE INVENTION

1. Field of the Invention

The present invention relates generally to the field of optical imaging and more particularly to optical systems for microscopic imaging, inspection and/or lithography applications.

2. Description of the Related Art

Many optical systems and electronic systems are available to inspect surface features of a specimen for defects, including specimens such as a semiconductor photomask or partially fabricated integrated circuit. Defects on such specimens may take the form of particles randomly localized on the specimen surface, scratches, process variations, repeating pattern defects, and so forth. Techniques and devices for inspecting specimens for these microscopic defects are generally available in the art and are embodied in various commercially available products, including those available from KLA-Tencor Corporation of San Jose, Calif., the assignee of the present application.

The aim of virtually any type of inspection system or technique is to rapidly and efficiently detect defects. With smaller and smaller features on specimen surfaces and the use of new materials and new manufacturing processes, detection of new and finer defects is required. It is also preferable to rapidly inspect a specimen surface in as short an amount of time as possible, from loading the specimen to removing it from the inspection position and characterizing the defects. Such speed requirements in the presence of smaller features mandates continuous improvements in the available techniques to accurately and adequately find specimen problems.

Inspection systems are available for wafer inspection, while still others target photomask inspection. The inspection systems currently available are highly complex, requiring a sophisticated combination of light source, illumination, imaging, positioning, automatic focusing, image sensor, data acquisition, and data analysis subsystems. A complete change in the inspection system may be required to allow the detection of new and smaller defects on a specimen.

Of the currently available systems, it should be noted that most use a non-pulsed light source from an arc lamp or a laser. A non-pulsed lamp or laser provides a relatively constant power to the specimen and is more easily implemented in a high speed inspection system. However, relatively constant and non-pulsed energy sources suffer from particular drawbacks. Short wavelengths have desirable characteristics for inspecting small defects. Few non-pulsed sources are available with the required power and brightness for high speed inspection at wavelengths below 300 nm. In addition, non-pulsed laser light sources do not produce light energy with relatively low spatial and temporal coherence, which can be a problem in certain circumstances. For this reason, these non-pulsed laser sources suffer from interference and speckle induced illumination discontinuities. Overcoming these problems requires time averaging of speckle patterns, such as by using a rotating ground glass plate.

It would therefore be desirable to have a system for inspecting a specimen that improves upon the systems previously available, and in particular for enabling inspection of specimens such as wafers and photomasks with short wavelength light that do not have the adverse effects associated with non-pulsed light sources.

SUMMARY OF THE INVENTION

The present invention is a system and method for inspecting a specimen, such as a semiconductor wafer or photomask, including illuminating at least a portion of the specimen using an excimer source employing at least one relatively intense wavelength from said source, detecting radiation received from the illuminated portion of the specimen, and analyzing the detected radiation to view potential defects present in the portion of the specimen.

These and other aspects of the present invention will become apparent to those skilled in the art from the following detailed description of the invention and the accompanying drawings.

DESCRIPTION OF THE DRAWINGS

FIG. 5 is a delay arrangement using two prisms, each prism including a TIR surface and an AR surface;

FIG. 6 illustrates two prisms rotated such that light energy entering makes a total of six round trips between prisms, thereby increasing overall delay time;

FIG. 27 presents a central dark ground imaging system wherein the laser passes through the collector at an approximately perpendicular angle to the object;

FIG. 28 is a top view of the normal dark field imaging system;

FIG. 47 is an example folded 0.7 NA catadioptric objective utilizing a single glass material;

FIG. 48 illustrates the effect of the lateral separation between rays transmitted to and received from the Mangin mirror;

FIG. 57 presents three different magnifications possible with the optically compensated zoom.

DETAILED DESCRIPTION OF THE INVENTION

Figure 1:
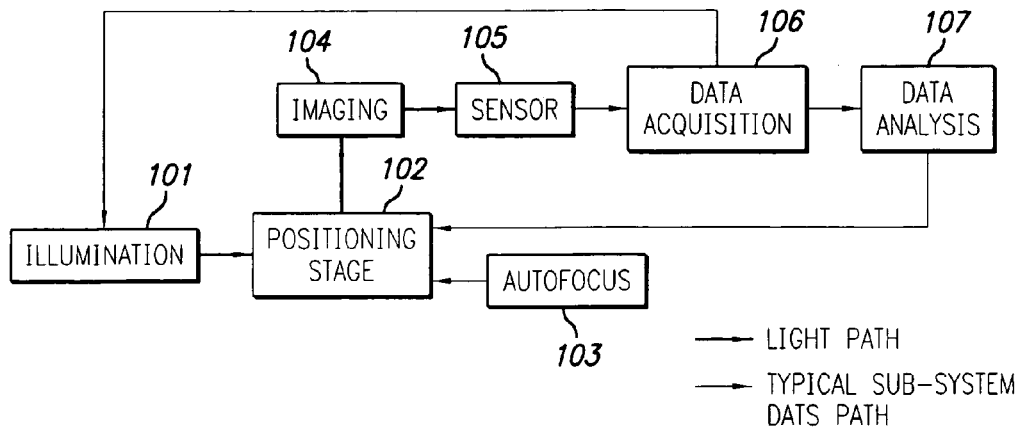
FIG. 1 illustrates functional aspects of the system disclosed herein.

The inspection system disclosed herein employs an excimer illumination subsystem having advantages over non-pulsed designs. FIG. 1 illustrates a typical inspection subsystem having an illumination subsystem 101, positioning stage 102, autofocus subsystem 103, imaging subsystem 104, sensor subsystem 105, data acquisition subsystem 106, and data analysis subsystem 107. The light path travels from the illumination subsystem 101 to the positioning stage 102, the imaging subsystem 104, and the sensor subsystem 105. Data passes between the autofocus subsystem 103 and the positioning stage 102, between the sensor and the data acquisition subsystem, and between the data acquisition subsystem and the illumination subsystem and the data analysis subsystem, and between the data analysis subsystem and the positioning stage.

Inspection Modes

Many different modes exist for inspecting partially fabricated integrated circuits and photomasks. Potential inspection modes include bright field, ring dark field, full sky, directional dark field, differential interference contrast, and confocal. These modes can be implemented in reflection for inspecting wafers and photomasks or in transmission for inspecting photomasks. An inspection system can support one or more of these inspection modes. In addition, an inspection mode referred to as aerial imaging can be used with photomasks to simulate the image profile at the wafer plane.

The bright field inspection mode is similar to common microscope systems where a magnified view of the object is projected onto a sensor. The advantage of bright field imaging is that the image produced is readily distinguishable. The size of image features accurately represents the size of object features multiplied by the magnification of the optical system. This technique can be more easily used with image comparison and processing algorithms for computerized object detection and classification on patterned objects. This inspection mode is commonly used for both wafer and photomask inspection.

The dark field inspection mode is primarily used to detect scattering from edges, small particles, and irregular surfaces. For example, smooth flat areas scatter very little light resulting in a dark image. Any surface features, particles, or objects protruding above the flat area scatter light and produce a bright. Dark field inspection modes provide a large signal for small features that scatter light. This large signal allows larger sensor pixels to be used for a given feature size, permitting faster wafer or photomask inspections. Fourier filtering can also be used to minimize the repeating pattern signal and enhance the defect signal to noise ratio.

Many different dark field inspection modes exist including ring dark field and directional dark field. Each uses a specific illumination and collection scheme such that the scattered and diffracted light collected from the object provides the best signal. The ring dark field inspection mode consists of illumination and imaging pupils that do not overlap. A typical example of this is an illumination NA that delivers light to the wafer or photomask through the high NA portion of the optical pupil. An aperture in the imaging pupil is used to block the central portion of the NA used for illumination and allow scattered light collected in the outer portion of the imaging pupil to pass and form an image. These systems have the advantage that features on the wafer or photomask are illuminated uniformly form all directions so features with different orientations are equally well imaged. The NAs can also be reversed with the illumination through the central portion of the NA and the imaging in the outer portion of the NA.

The directional dark field inspection mode can have a wide variety of configurations. Each configuration is optimized for particular defect types. One configuration, sometimes referred to as aperture shaping, uses apertures placed at the illumination and imaging pupils. The apertures are used to select different portions of the illumination and imaging pupils. For example, an aperture can be placed near the edge of the illumination pupil. This effectively delivers a small cone of light at a high incident angle to the wafer or photomask. Another aperture or apertures can then be placed in the imaging pupil to select a desired portion of the scattered light. For example, two apertures can be placed 90 degrees to the illumination pupil aperture selecting the light scattered sideways from features on the wafer or photomask. Many other examples of illumination and imaging pupil apertures can be used to optimize for specific defect types. Another configuration, sometimes referred to as laser directional dark field, uses one or more lasers that illuminate the sample at high angles of incidence from outside the objective. Often four illumination beams are chosen at 90 degree angles from one another. This helps eliminate any directional dependence of features on the sample. A further configuration, sometimes called internal laser dark field, is a hybrid of the aperture shaping and the laser directional dark field modes. In this mode a laser is injected into a particular location in the illumination pupil of an optical system.

The full sky optical configuration is a combination of bright field and ring dark field configurations. Full sky consists of using different amounts of attenuation. The relative bright field signal and dark field signal can be adjusted. This allows the detection of both bright field and dark field defects simultaneously using the same sensor.

The Differential Interference Contrast (DIC) inspection mode is primarily used for its ability to resolve gradients in the topology of object features. The image contrast increases for increasing gradients in the optical path. DIC mode uses a spatial shearing system with the shear distance on the order of the optical system resolution, and is typically implemented by separating the illumination into two orthogonal polarized beams. These beams interact with the features on the object and are the recombined before the image is formed.

The Confocal inspection mode is primarily used for its ability to resolve the topology differences of object features. Most optical configurations have difficulty detecting changes in the topology of features. The confocal configuration discriminates between different heights by using apertures near the illumination and imaging focus. Laser illumination can also be used to eliminate the need for the illumination aperture.

Each of the inspection modes can be implemented in reflection for inspecting wafers or photomasks, or in transmission for inspecting photomasks. Photomask inspection has the added advantage of being able to perform transmitted and reflected inspection simultaneously.

The Aerial Imaging configuration is typically used with transmitted light for photomask inspection. The goal of Aerial Imaging is to simulate the conditions present in a lithographic exposure tool. The main advantage of this inspection mode is that only photomask defects that will print on the wafer will be imaged. This mode tends to have an indirect measurement of defects on the photomask. If an error is detected in the image, the defect type causing the error can generally only be inferred.

Illumination

The present system employs an excimer laser illumination subsystem. This system is composed of an excimer laser that is optimized for inspection applications and optics to relay the excimer illumination onto the sample. In addition, optical assemblies for reducing the peak power of each pulse, improving the spatial uniformity, and reducing speckle contrast of each pulse may be employed.

An excimer laser used in a high speed inspection system has specialized requirements not available on commercial excimer lasers. These requirements affect the design of the laser. The requirements are a repetition rate high enough to support the desired data rate, long lifetime, low cost of ownership, low coherence, and stable output. In addition, the laser can be operated with its natural linewidth for improved speckle smoothing or line narrowed to simplify the optical design. The excimer laser distributes pulsed light energy at relatively high powers, with wavelengths including approximately 308 (XeCl), 248 (KrF), 222 (KrCl), 193 (ArF), 157 ($F_2$), and 126 nm, where such excimer lasers may include a discharge chamber containing two or more gases such as a halogen and one or two rare gases. Other gases, including but not limited to XeF (350 nm) may be employed with the excimer laser. Natural bandwidths range from several nm for a 248 nm excimer to 1 pm for a 157 nm laser, and bandwidths may be narrowed using dispersive components within the laser cavity. Excimer lasers employed may have high duty cycles to allow for continuous operation without the need for frequent maintenance. The excimer laser light source may include low jitter characteristics and pulse to pulse feedback may be employed using a specialized sensor or the image sensor itself.

It is also possible to reduce the contrast of interference and speckle by reducing the spatial coherence of the excimer laser. Traditionally, excimer lasers use plane mirror resonators. An excimer laser in this configuration typically has low spatial coherence. However, it is possible to use a cavity with curved reflective surfaces, or mirrors, to further reduce spatial coherence.

A further aspect of the present illumination subsystem is the ability to address speckle concerns and provide a system addressing peak power associated with energy transmission. The subsystem uses multiple beam splitters in an arrangement that has the ability in many environments to minimize the energy variation between pulses. This system allows for a flexible setup where various combinations of plate beamsplitters and cube beamsplitters in different arrangements and geometries may be used while still within the scope of the teachings of the current invention.

Typical optical delay lines can be a major source of losses. The losses in the delay arms result from imperfect optics such as mirrors having less than 100% reflectivity, beamsplitters with loss and unequal beamsplitting ratios, absorption of light energy in glass materials and coatings, and light energy scattering effects. These optical delay line losses adversely contribute to variations in the pulse-to-pulse energy unless a method of compensation is used. In the present pulse stretching scheme, components may be introduced between the beamsplitters to compensate for losses in the beamsplitters, mirrors, and optical delay lines. The net result is that the pulse energies tend to be more uniform. High efficiency within the system minimizes the required introduction of compensating losses.

Figure 2:
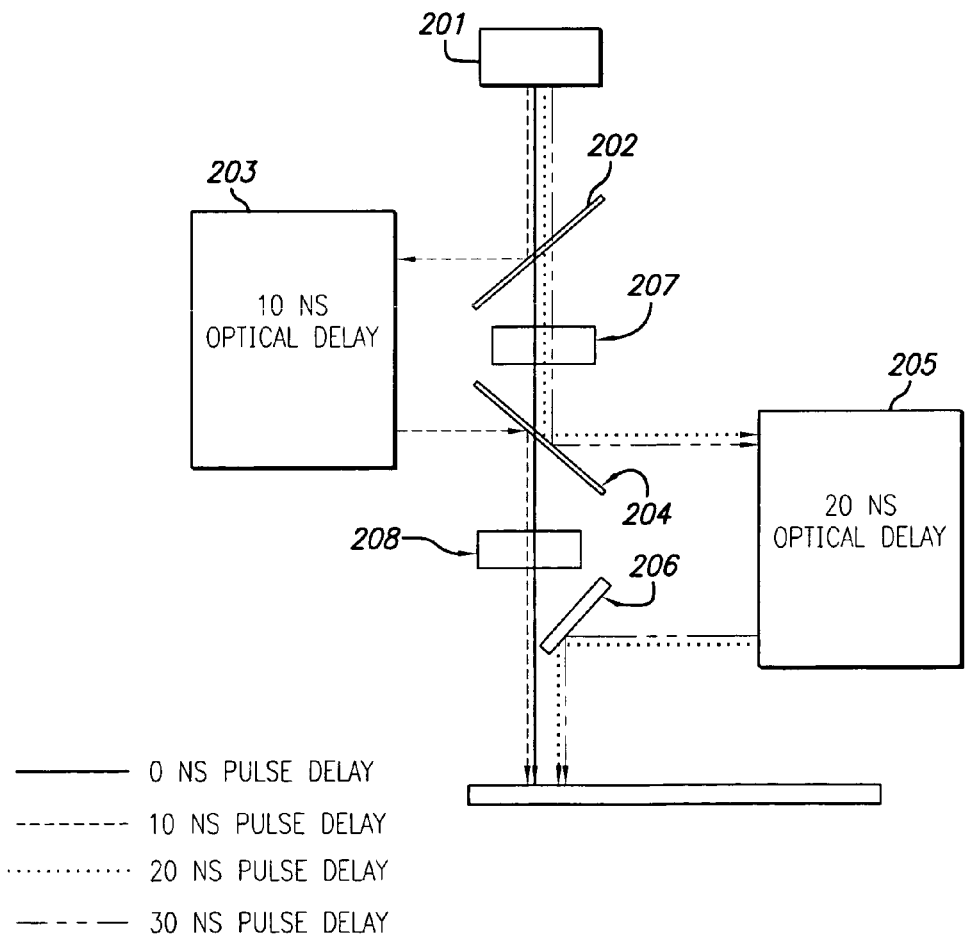
FIG. 2 illustrates an aspect of the design used to reduce the peak power of a laser pulse, and one that can be altered by varying the angles of the components to reduce speckle contrast for a single laser pulse.

A schematic of an aspect of a scheme to generate four pulses is shown in FIG. 2. From FIG. 2, light energy is initially generated by an excimer laser 201. The light energy is shown as four separate beams to more clearly illustrate the formation of four separate pulses. In most real situations only a single light beam would originate from the excimer laser. The light energy from excimer laser source 201 is a pulsed light source. Light is transmitted toward beamsplitter 202, which splits the light energy. The pulse reflected by beamsplitter 201 is directed to the 10 ns optical delay 203, and beamsplitter 204. Beamsplitter 204 may again either split the beam or permit the beam to pass through. If it passes through, it is directed to the 20 ns optical delay 205, mirror 206, and to the specimen. In the case of the pulsed light energy passing through beamsplitter 202, said light energy contacts loss compensator 207 and subsequently passes to beamsplitter 204. Loss compensator 207 compensates for imperfect optical components such as the beamsplitter 202 or loss in optical delay 203. In this manner, light energy reflected by beamsplitter 202 contacts beamsplitter 204 at the same or nearly the same energy as light energy passing through beamsplitter 202 and loss compensator 207. Similarly, light energy from beamsplitter 204 that passes through loss compensator 208 strikes the sample surface at approximately the same energy as light passing the 20 ns optical delay 205 and mirror 208. If the light from source 101 is polarized, mirror 208 could be replaced by a waveplate and polarizing beamsplitter. In this manner the beams can be easily co-aligned. This mechanization provides for varying delays of the pulsed light energy such that light energy strikes the specimen surface at a desired time with relatively uniform energies.

The design presented in FIG. 2 generates four pulses each delayed by a different amount of time.

The pulse passing directly through both beamsplitters has no delay introduced, while deflecting off both beamsplitters introduces a 10 nanosecond delay. 20 and 30 nanosecond delays can also be introduced in this arrangement as shown. This introduction of delay reduces the peak power of the pulses contacting the specimen surface.

Figure 3:
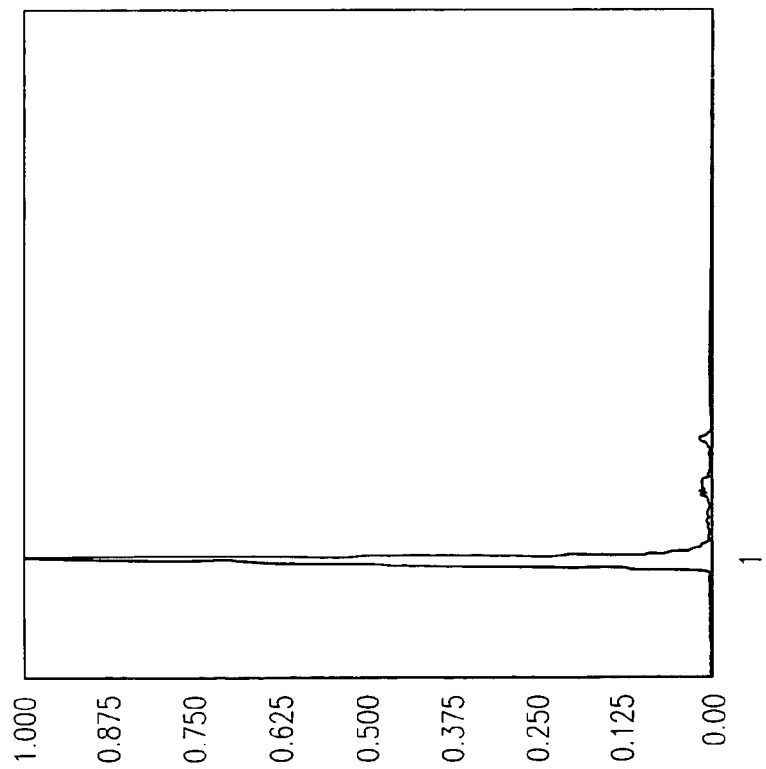
FIG. 3 shows a plot of the intensity of a single pulse.
Figure 4:
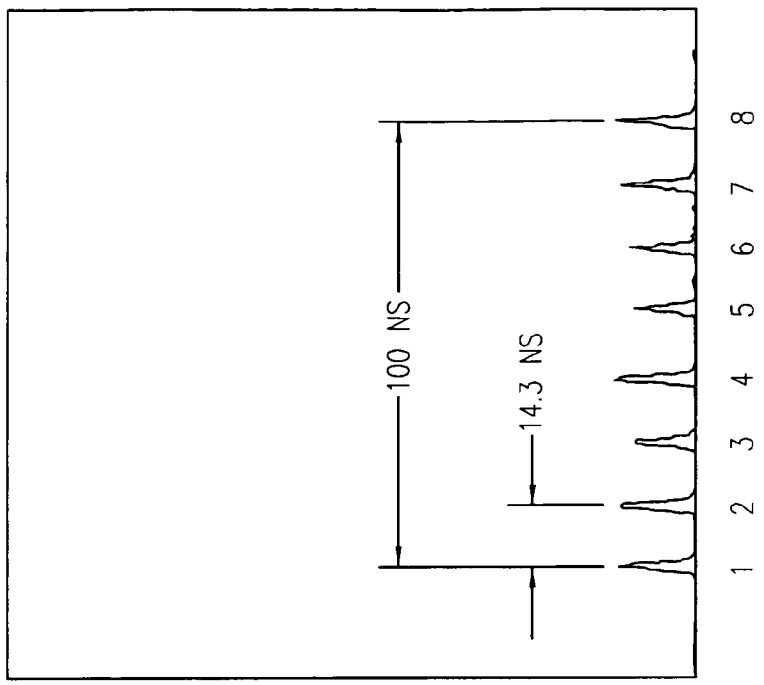
FIG. 4 is a plot of the intensity of multiple pulses, specifically eight pulses, resulting from the use of the system and method similar to the one illustrated in FIG. 2.

The effects of using a design similar to the one illustrated in FIG. 2 are illustrated in FIGS. 3 and 4. The system used to generate the pulses in FIG. 4 is capable of producing eight pulses delayed by varying amounts of time. In FIG. 4, a 532 nm laser pulse is delivered to the specimen surface. The magnitude of the energy striking the surface is 100 percent. FIG. 4 shows the multiple pulses delivered to the surface, wherein the spacing between pulses is 14.2 nanoseconds, and eight pulses are delivered in 100 nanoseconds. The magnitude of the pulses delivered is on the order of 12.5 percent. Thus rather than exposing the surface with a single large energy pulse, the surface is contacted by multiple smaller pulses.

A scheme to create multiple pulses from a single pulse poses problems with producing a uniform energy for the multiple pulses. This is especially true when a large number of pulses or long delays are required. In addition, maintaining uniform pulse amplitudes is further complicated in the UV-DUV portion of the spectrum. Optical losses tend to be very high because of increased absorption, less efficient AR and HR coatings, and increased scattering. However, even efficient optical systems can still suffer significant differences in pulse energies. In this scheme, compensators are used to add additional losses, similar to those produced by the beamsplitters, mirrors, optical delay lines, and so forth, in order to make the pulse energy uniform.

Many different schemes can be used for compensation. A common technique is to use attenuation in the form of reflective or absorbing filters. The appropriate filters can be used to compensate for the losses and make the pulse energies uniform. Continuously variable filters are available that allow exact matching. In addition, other techniques can be used, such as employing a polarization based attenuator when using polarized light.

The optical delay line is an important component of the present system. Imaging relays or stable optical cavities are preferred because they maintain the beam profile and stability over long optical delay paths. Many of these schemes are commonly known in the industry. Reflective cavities such as White cells, Herriott cells, or other reflective multipass cells are typical examples. One major problem with these types of multipass cells is they can be very inefficient. If long optical delays are necessary, many cavity round trips will be required with many mirror reflections. In the DUV-VUV spectral range, where mirror coatings may not be highly reflective, the efficiency of an all reflective optical delay line may be unacceptable. For this reason it is desirable to employ optical delay schemes that minimize losses.

In the DUV-VUV spectral region, antireflection coatings are typically more efficient than HR coatings. In addition, interfaces at Brewster's angle and TIR surfaces can have extremely low loss. The present design allows the use of novel optical delay schemes that can utilize Brewsters angle surfaces, TIR surfaces and transmissive surfaces that can be AR coated to greatly enhance the efficiency of the optical delay scheme. One such novel optical delay scheme utilizing these types of surfaces is illustrated in FIG. 5. The system of FIG. 5 utilizes two prisms, left prism 501 right prism 502, having total internal reflections and an AR coated surface as an optical delay mechanism. This arrangement has the additional advantage that the optical delay can be tuned simply by rotating the prisms about their common axis. From FIG. 5, the light beam is introduced into the arrangement and is deflected by a mirror 506 to left prism 501, which directs light outward toward right prism 502. Right prism 502 has two TIR (total internal reflection) surfaces 503 and an AR (anti-reflective) surface 504 for directing the beam back toward left prism 501. After a single pass through the arrangement, light energy exits the arrangement, shown as the output beam in FIG. 5 using mirror 505 to direct the light energy outward. Additional methods can be used to direct the input and output beams. Examples of these methods include a single mirror using the front surface for the input and the rear surface for the output, or a prism using TIR and AR surfaces in much the same manner as prism 501 and 502. In addition, the input and output beams can be located in a variety of positions within the cavity to suit the particular application. This produces the necessary delay for the system in an efficient manner. As may be appreciated, the desired time of the delay directly affects the spacing between the various components.

Figure 7:
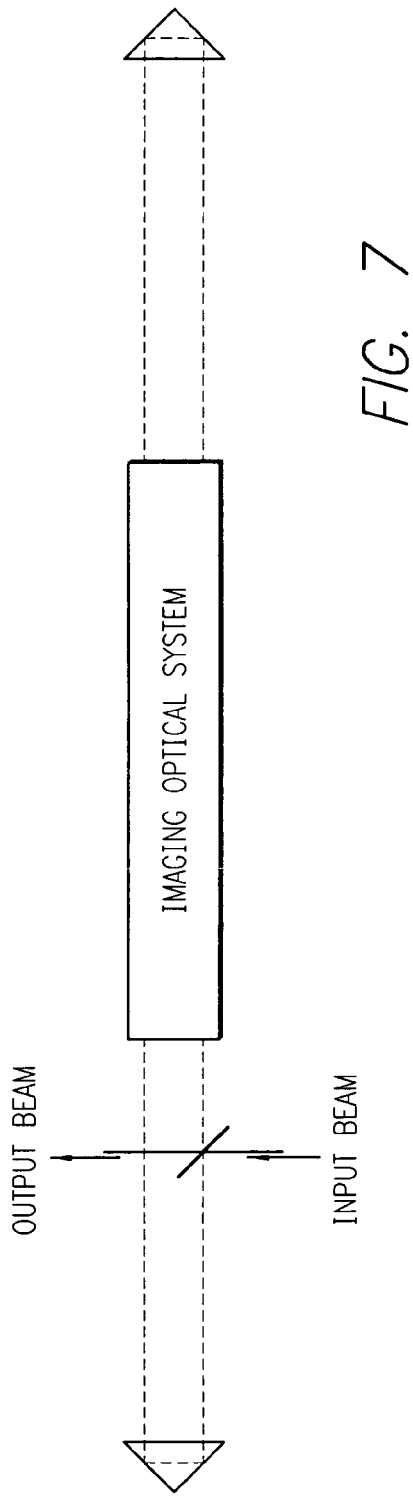
FIG. 7 is a delay arrangement employing a single image relay lens.
Figure 8:
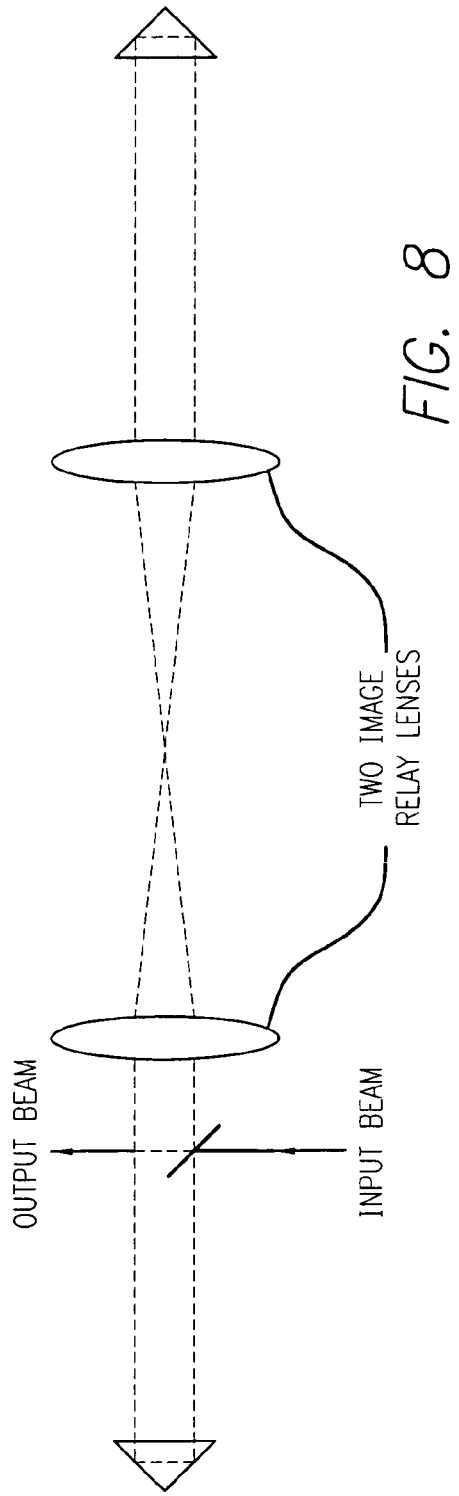
FIG. 8 illustrates a delay arrangement having two image relay lenses.

Further delays may be obtained by creating multiple trips between the reflecting surfaces prior to passing the light energy out of the arrangement. The increase in delay by rotation of the left prism 501 and right prism 502 are shown in FIG. 6. The arrangement shown in FIG. 6 has the limitation that the beam is not re-imaged as it passes back and forth between the prisms. An image relay can be added to the arrangement of FIG. 6 by placing a lens or lenses between the prisms. Addition of a lens or lenses provides for re-imaging such that an image may be retrieved and processed at varying points in the design, thus providing increased control over the quality of the image received. An imaging relay can be inserted in the optical delay arrangement as shown in FIG. 8. This optical delay improves the stability and maintains the beam size for long optical delays. An image relay example using two lenses in an afocal telescope arrangement is shown in FIG. 7. Alternately, one or more prism surface can be curved to act as a lens, in the case of an AR surface, or a curved mirror, in the case of a TIR surface, for purposes of re-imaging the light.

Figure 9:
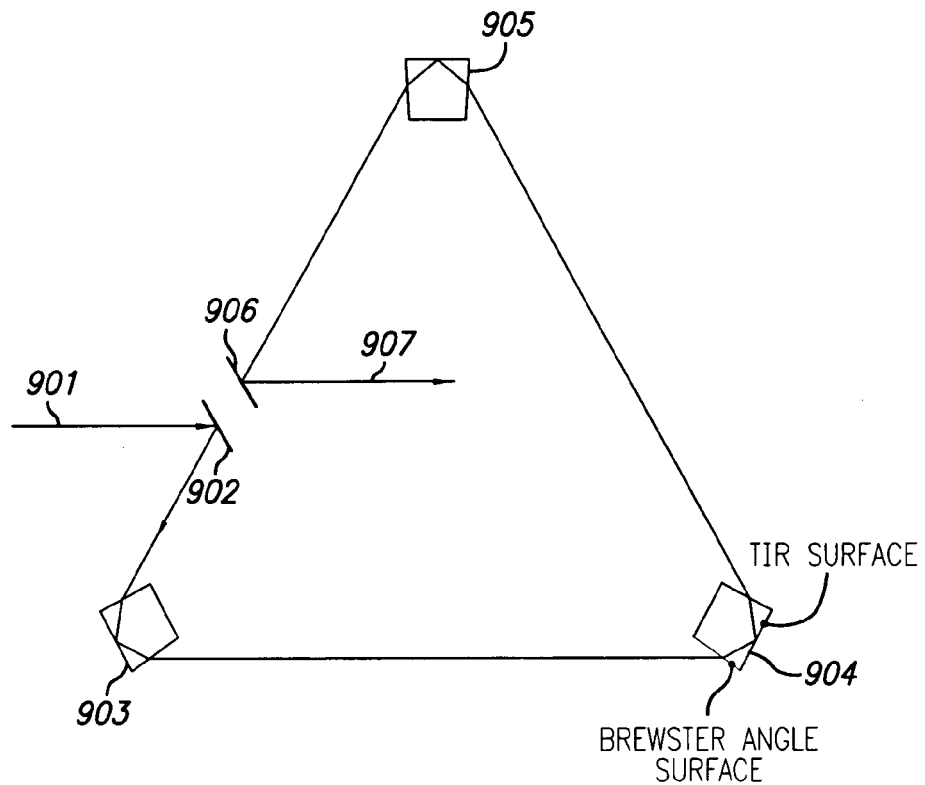
FIG. 9 presents a delay arrangement wherein three prisms are used each having a TIR surface and incorporating a Brewster's angle surface.

Novel optical delay schemes utilizing TIR and Brewster's angle surfaces are also possible. One such optical delay geometry is shown in FIG. 9. From FIG. 9, input beam 901 is directed into the arrangement and redirected using a mirror 902 toward first prism 903. First prism 903 directs the received beam toward second prism 904, which directs the beam toward third prism 905. Each prism has a TIR surface and two Brewster angle surfaces to efficiently deflect and transmit the light energy. Once light energy is reflected by third prism 905, it is output as output beam 907 from the arrangement using a mirror 906. A lens or lenses can also be added to this geometry to re-image the light, either in the path of the light or at the entrance or exit of one of the prisms. Multiple round trips can be achieved by providing a small angle of the beam out of the plane of the drawing in FIG. 9. This will cause the beam to walk down the surfaces of the prisms with each round trip.

The system further includes the ability to reduce speckle effects in transmitted and received light. It can be shown that when a laser beam enters a diffuser at a different angle, the speckle pattern of the light energy leaving the diffuser also changes. This change in speckle pattern for different angles enables generation of multiple speckle patterns by multiple beams at multiple angles when light energy passes through a diffuser. These speckle patterns can be integrated together to reduce the speckle contrast. However, in order for integration to function properly, each speckle pattern must arrive at the detector at slightly different times. Varying arrival times of speckle patterns can be achieved by using the same optical apparatus previously described to reduce the peak power of a laser pulse. The optical apparatus, such as that illustrated in FIG. 2, generates multiple pulses separated in time from a single input pulse.

Figure 10:
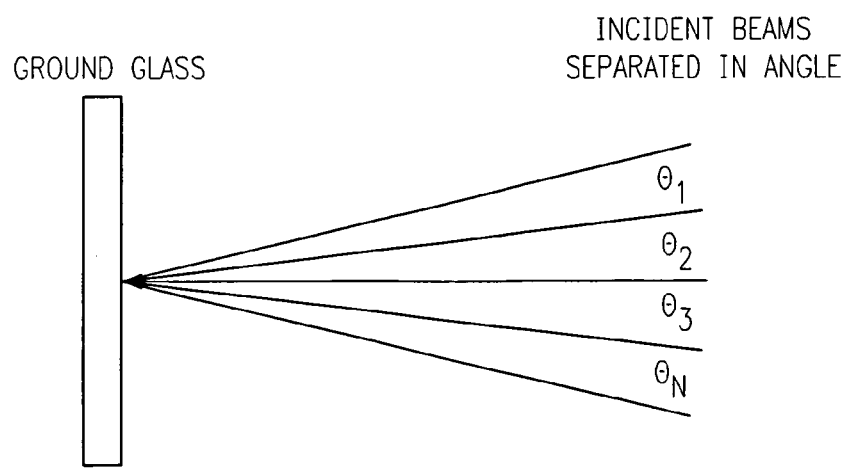
FIG. 10 is a preferred angular arrangement of pulses to apply to ground glass to reduce speckle contrast in accordance with the design of FIG. 2.
Figure 11:
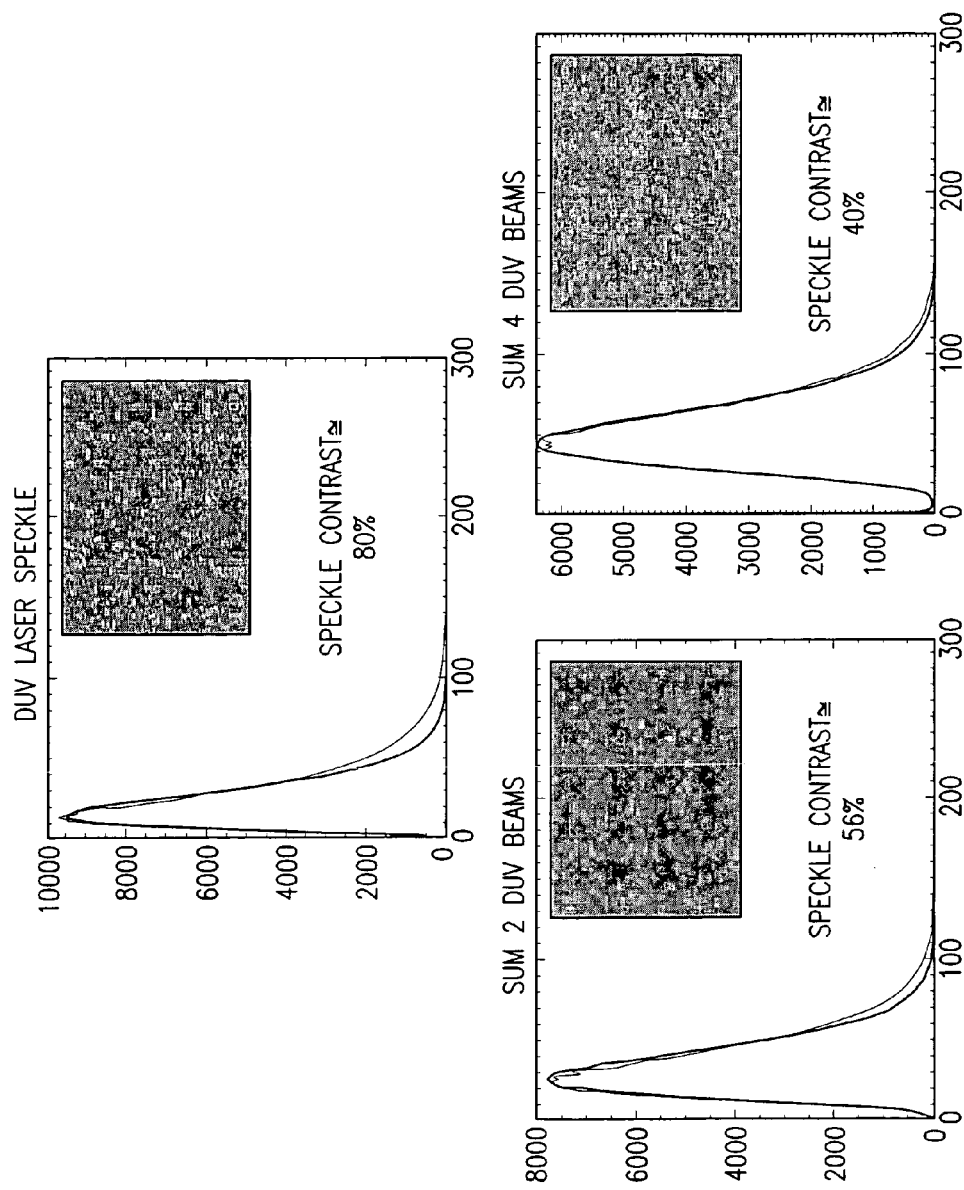
FIG. 11 shows the results of a standard laser pulse, the use of two DUV pulses, and four DUV pulses and the associated speckle contrasts.

The difference between using the system illustrated in FIG. 2 for reducing peak power and using the system to reduce speckle contrast is the alignment of the optical apparatus. Typically, when multiple pulses are generated to reduce the peak power of a single pulse, all the optical paths are co-aligned to have the same optical axis and the same beam position at the exit of the optical apparatus. However, for reducing the speckle contrast, it is desirable to have different angles between the different optical paths. Different angles are achieved by slightly changing the angles of the mirrors and beamsplitters in the optical apparatus. This angular change produces different angles between each output pulse as the pulse exits the optical apparatus and enters the diffuser as shown in FIG. 10. The result of using two and four pulses to reduce the contrast of a speckle pattern is shown in FIG. 11. From FIG. 11, a typical DUV laser arrangement without the implementation of FIG. 2 having varying angles between optical paths produces a speckle contrast of 80 percent. Use of the implementation of FIG. 2 may entail, for example in a two DUV beam arrangement, light energy being directed through the beamsplitters and loss compensators for one channel, i.e. the 0 ns loss leg of FIG. 2, as well as the 10 ns path. Such an implementation requires redirecting at least one path of light energy, such as the energy emitting from the 10 ns delay path, so as to contact the surface at an angle different from the 0 ns energy path in a manner as demonstrated in FIG. 10, i.e. at an offset angle from the 0 ns path. Using this type of implementation, speckle contrast may be reduced to on the order of 56 percent. Use of four separate and summed DUV beams, such as all four paths illustrated in FIG. 2, reduces the speckle contrast to on the order of 40 percent.

One problem with this scheme is that diffusers may not be efficient. In the arrangement illustrated in FIG. 2, a phase plate may be inserted in the system instead of a diffuser to increase efficiencies. Phase plates with multiple levels or continuous profiles can provide efficiencies approaching 100%.

Figure 12:
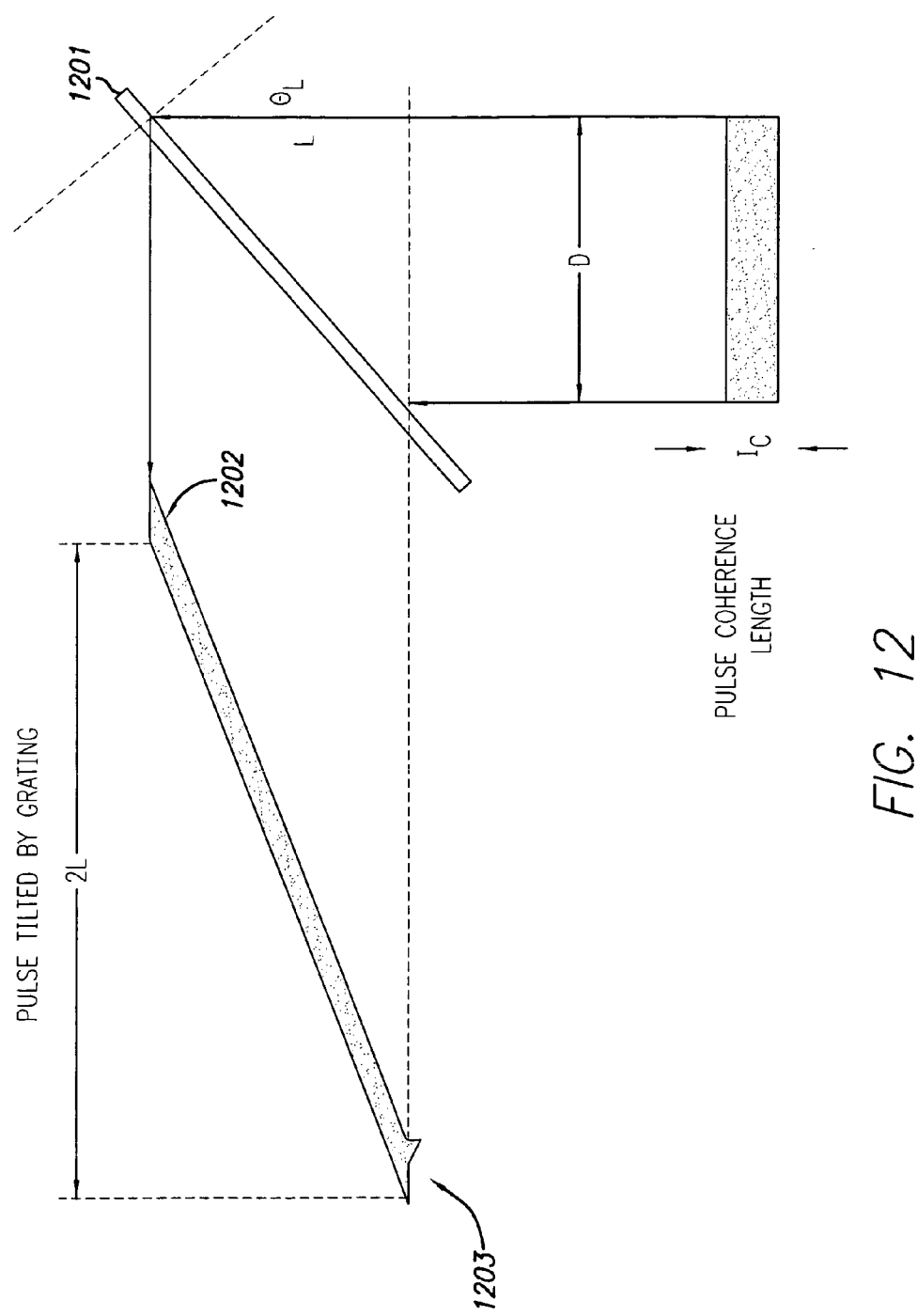
FIG. 12 is an alternate aspect of the method and apparatus for reducing speckle contrast employing an angularly offset diffraction grating.

The second method for reducing speckle contrast using a single pulse employs a grating to produce an optical delay from one side of the pulse to the other. The use of a grating to delay a portion of the pulse is illustrated in FIG. 12. Grating 1201 causes one side of the laser wavefront to be delayed in time. This delay caused by grating 1201 changes across the beam making the wavefront tilt in time. In FIG. 12, the wave emanates from the light generating device (not shown) at the bottom of the illustration. The pulse has a diameter D and in the arrangement shown the left portion of the beam strikes the grating 1201 and is redirected by the grating 1201 before the right half of the pulse strikes the grating. The distance covered in a fixed period of time is the same for the right and left side of the pulse, and thus by the time the right side of the pulse reaches location 1202, the left side of the pulse has reached location 1203. From the illustration, the right side of the pulse covers an additional distance L before striking grating 1201. The illustration shows an approximate 45 degree angle between the pulse and grating 1201, but in practice other angles could be employed while still within the scope of the invention. In the illustrated 45 degree angle case, the right side of the pulse covers a distance that is ultimately 2 L shorter than the distance covered by the left side of the pulse. This differential in time or in distance covered produces a differential akin to the delay produced by the implementation of FIG. 2. The resultant tilted wavefront can be used in combination with a diffuser or phase plate to reduce the speckle contrast.

Figure 13:
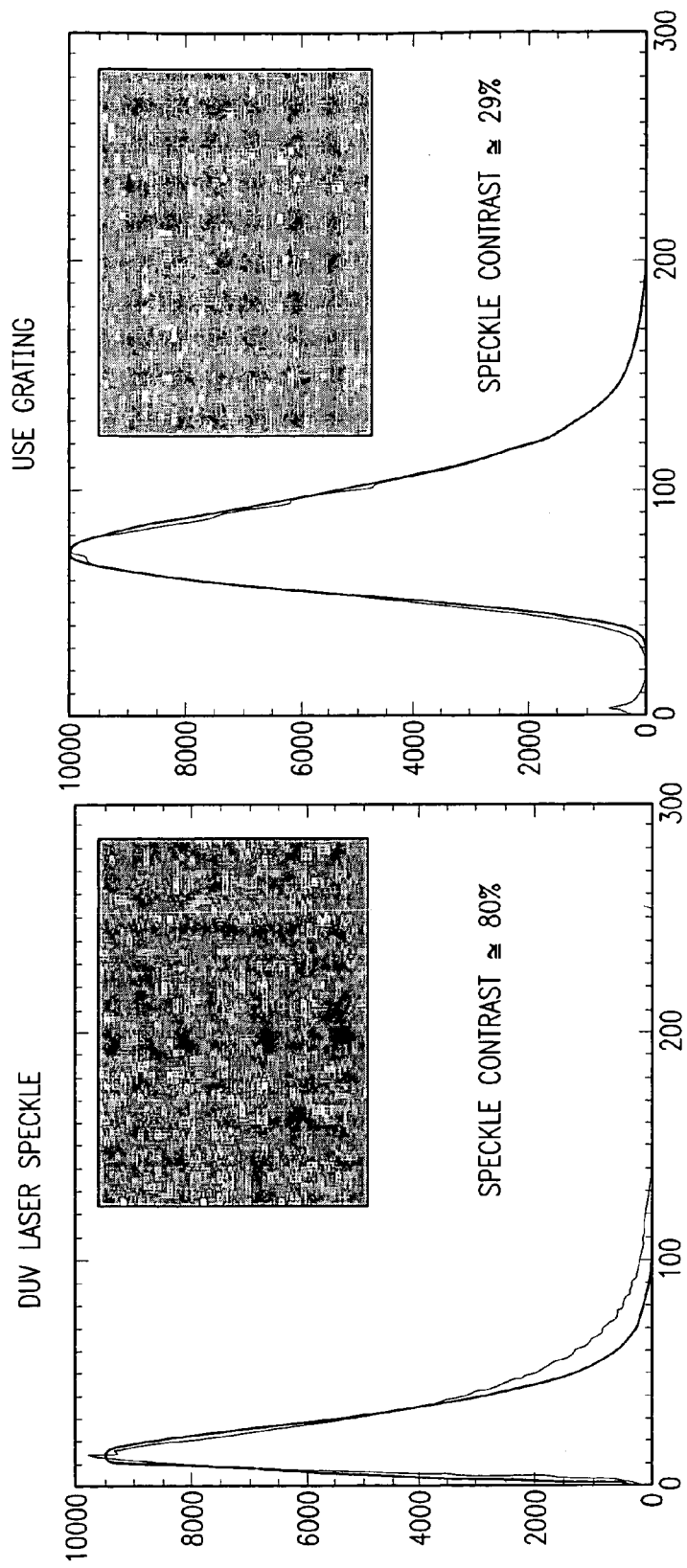
FIG. 13 is the resultant speckle contrast of the grating arrangement used in FIG. 12.
Figure 14:
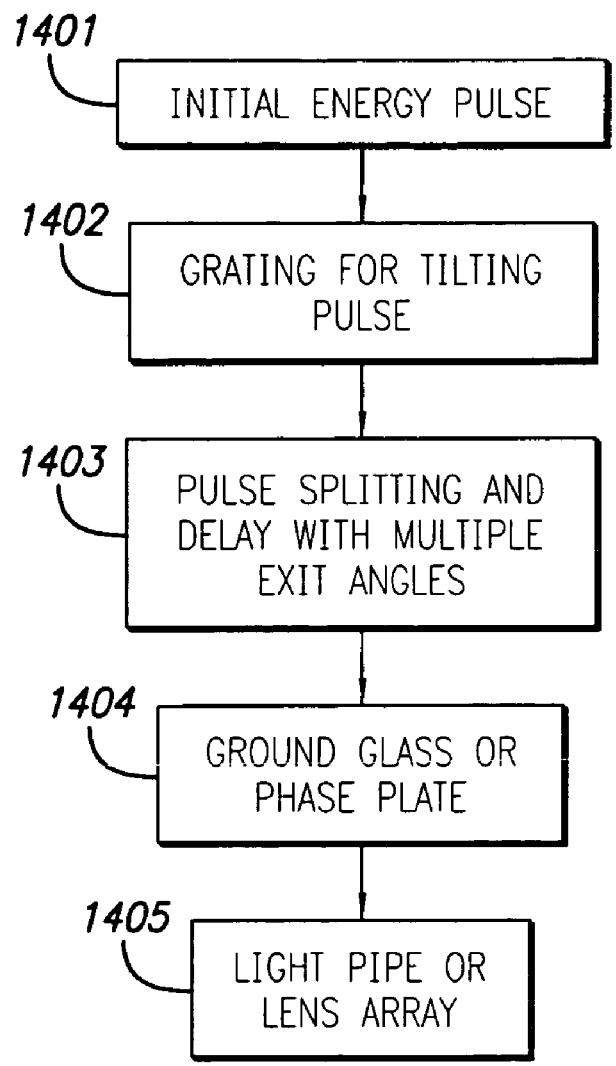
FIG. 14 illustrates a functional diagram of the elements used in a device that reduces peak power and speckle contrast.

From FIG. 12, the initial laser pulse will have a well defined coherence length. After the pulse passes through grating 1201 one side of the pulse is delayed and the coherence length remains the same. The right side of the pulse is delayed with respect to the left side by:

$$\text{Delay} = 2L = 2D \tan \theta_i$$

where D is the diameter of the input beam and $\theta_i$ is the diffraction angle. This mechanization effectively breaks up the pulse into many independent sections that do not interfere with each other. These independent sections combine in intensity to reduce the speckle contrast. The number of independent sections is equal to:

$$\text{Sections} = \frac{2L}{l_c}$$

where 2 L is the maximum delay and $l_c$ is the coherence length. The result of the use of a grating such as that presented in FIG. 12 to reduce the contrast of a speckle pattern in shown in FIG. 13. From FIG. 13, speckle contrast may be reduced from 80 percent for a single pulse to 29 percent using a grating as shown in FIG. 13.

Speckle reduction techniques using the implementation of FIG. 2 and that of FIG. 11 may be used in combination to further reduce speckle contrast. In addition, the use of optical delays and gratings or other redirectional or delaying elements can be used in combination with a light pipe or lens array to produce an ideal uniform illumination source with low peak power and low speckle contrast. FIG. 13 illustrates the operation and elements in a system for reducing speckle contrast. Step 1301 involves generating the initial laser pulse. Step 1302 provides for tilting the pulse using a grating such as the grating 1201 presented in FIG. 12. Step 1403 comprises splitting the pulse received from the grating and delaying the pulse using multiple exit angles. Step 1404 indicates passage of the varying angle and delayed pulses through ground glass or phase plates and subsequently passing the received light energy to a light pipe or lens array in step 1405. Other combinations of the pulse delay or dividing and combining techniques disclosed herein are possible while still within the course and scope of the invention.

The system and method described for creating multiple pulses from a single pulse effectively increases the repetition rate of a repetitively pulsed source. For example, if a 2 kHz excimer laser is used in combination with the system designed to create four pulses as described in FIG. 2, the repetition rate is increased to 8 kHz. In addition, the system and method described for reducing the speckle contrast from a single pulse using a grating to delay one side of a pulse with respect to the other side effectively increases the pulse length in time. It is therefore conceivable that by using both of these techniques in combination, a continuous or nearly continuous source can be produced from a high repetition rate source. To illustrate this, assume a laser operating at 80 MHz with a 100 ps pulse width is used in combination with a system, similar to that described in FIG. 2, designed to create 32 pulses with the appropriate delays, the repetition rate is effectively increased to 2.6 GHz. The pulse separation of the 2.6 GHz source is around 400 ps. Now if the 100 ps pulse can be stretched to 400 ps, the source can be considered continuous. Using a grating at a symmetric 45 degree angle, the 100 ps pulse can be stretched to 400 ps using a beam 2.4 inches in diameter. One potential problem with this approach is the spectral dispersion created by the grating. This can be eliminated by adding a second grating. This eliminates the spectral dispersion while maintaining the optical delay from one side of the pulse to the other.

Positioning

The positioning subsystem for an excimer laser based inspection system has several desirable aspects. Some of the desirable aspects are high speed positioning of the specimen, rotation capability for alignment of the specimen, translation along the optical axis for focusing of the specimen, and position output for are synchronizing with the excimer laser.

High speed positioning of the specimen can be achieved using a precision stage. Stages of this type typically use air bearings on a precision surface, including but not limited to granite, to define the motion. High speed motion is most often achieved using one or more linear motors. It is also possible to produce high speed motion using a lead screw with servo motors. The excimer laser based inspection system may have loose requirements for vibration and speed variation in the stage if only a single pulse is used for illuminating the sample. This is because the illumination pulse typically lasts only 10 nanoseconds to 1 microsecond or so with pulse stretching. A short exposure time may effectively make stage may appear to be stationary. Small variations in the stage position may be within the overlap area of the individual exposure frames.

There are several desirable scanning options for a stage used for high speed inspection. The primary method commonly used to inspect patterned samples like wafers and photomasks is to use a raster scan. In this technique the stage moves the sample across the imaging subsystem field of view in one direction. The stage is then incremented in the orthogonal direction and the stage moves the sample across the imaging subsystem field in the opposite direction. This is repeated until the desired area of the sample is inspected. It is also possible to move the sample in an R-theta scan. In this technique the sample is rotated across the imaging subsystem field of view. As one rotation is complete the radius is increased until the desired area of the sample is inspected. The sample can be stepped I the radial direction or continuously moved to create a spiral inspection path.

It may also be desirable to have rotation capability on a raster scanning positioning subsystem. This allows features on the sample such as straight lines or objects oriented in rows or linear patterns to be aligned with the scanning direction. As the sample is scanned the line or pattern will maintain the same position on the image sensor. This can simplify and speed up the high speed data analysis.

There are two approaches to synchronizing the stage and excimer laser. In one approach, the excimer laser is synchronized with the stage position. An excimer laser can be triggered with high accuracy to coincide with the desired illumination area on the sample. Triggering requires the stage have the ability to provide accurate position output using encoders, distance measuring interferometers, or other position sensing devices. In another approach the stage is synchronized to the excimer laser firing. Synchronization according to this approach requires the stage speed to be varied so the desired stage position coincides with the arrival of the laser pulse.

Focusing the sample can be performed using a stage having the ability to move along an axis parallel to the optical axis and orthogonal to the scanning plane. Focusing often has several desirable aspects. Focusing may be fast enough to maintain focus during a high speed scan. This may require operation at 1000 Hz or higher. The resolution may be high enough to stay substantially within the depth of focus of the optical system. For high NA, short wavelength systems, this is often less than 50 nm. This requires a high resolution motion system such as a PZT system.

Imaging

Figure 17:
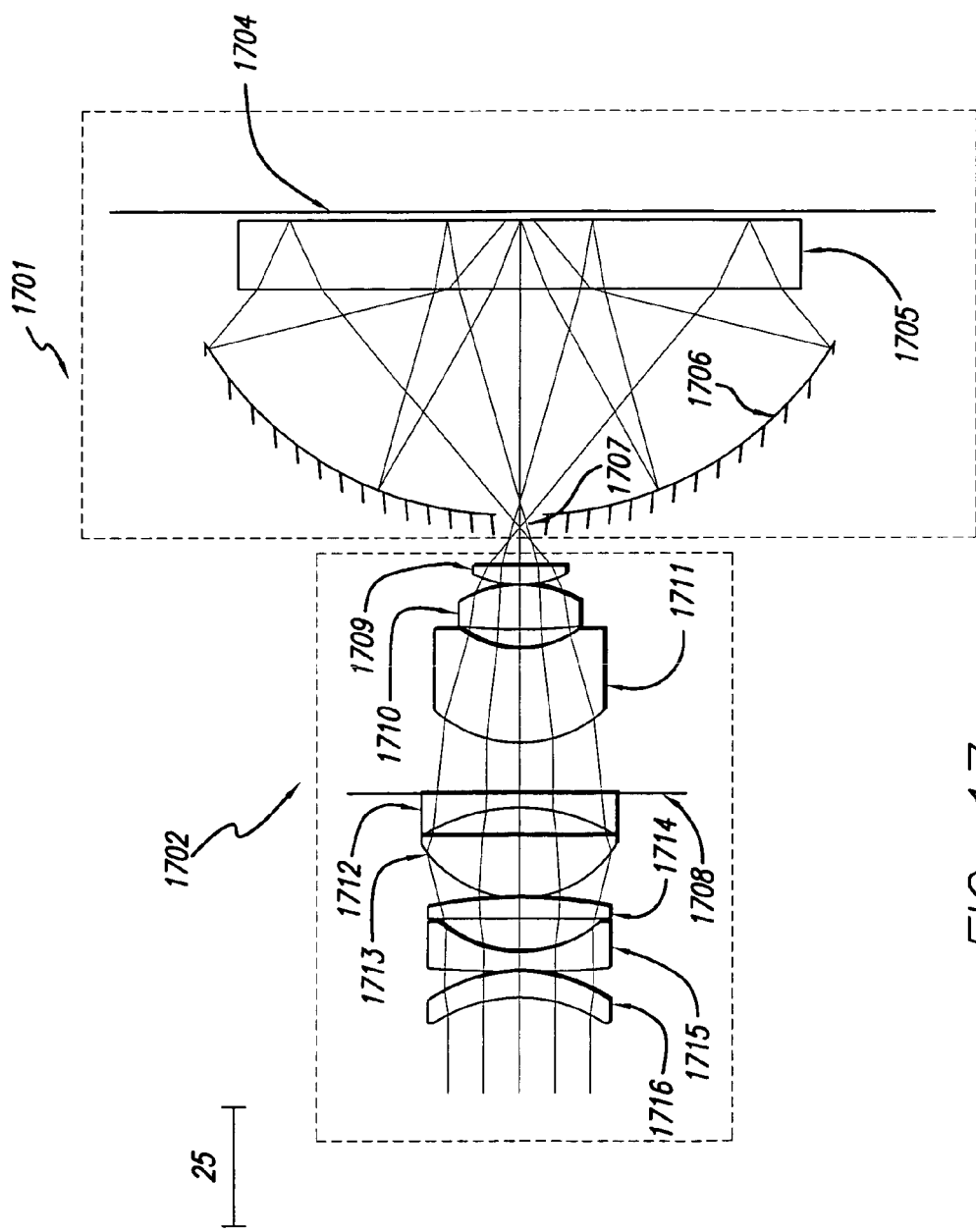
FIG. 17 is a multimode catadioptric dark field imaging system constructed to have a 0.97 NA.

The design of the imaging element of the system may be a high numerical aperture (NA) system having a large field and accommodating the narrow band excimer laser light source to support a variety of imaging modes. Single shot imaging may not require use of a TDI sensor, while multiple shot imaging addresses issues of blurring, is synchronized between shots, and is smoothed via optics, laser, sensor variation, and peak power techniques. Broadband and narrowband imaging is supported, where broadband may include diffractive optics and the use of two materials for all refractive imaging. The optical design may utilize more than one wavelength for autofocus, optics with an external pupil or Fourier plane, and zoom capability. Purging and contamination control of the optics may be provided, such as being oxygen free for 157 nm light energy sources. Referring now to FIG. 17, shown is a figure illustrating an apparatus that combines the functions of several imaging systems. This apparatus, based on a high NA catadioptric optical design, is a narrow band optical system having an NA greater than 0.90 and is highly corrected for low and high order monochromatic aberrations. The system may have a numerical aperture of greater than 0.65. Preferably the numerical aperture is greater than 0.90. The field size preferably ranges from 0.5 to 2.0 mm.

The high NA catadioptric optical system disclosed herein may have an NA in air up to 0.99 and a field size of greater than 1 mm. Such a system has relaxed manufacturing tolerances and only requires a single glass material. Use of a single glass material in the catadioptric system is very advantageous when the system is optimized for the spectrum below 300 nm because only a few glasses with high transmission are available.

The high NA catadioptric objective illustrated may be used and optimized for light beams having different wavelengths, from the infrared to the deep ultraviolet. For example, in the ultraviolet spectrum, light beams having wavelengths of 193 nm, 213 nm, 244 nm, 248 nm, 257 nm, 266 nm, and so forth are possible using the concepts disclosed herein, with adjustments that would be apparent to those of ordinary skill in the art. For wavelengths from 110–200 nm, fluoride glasses may be used because of their advantageous transmission properties.

The illustrated catadioptric optical system provides high quality imaging performance at numerical apertures (NAs) up to 0.99. This NA range represents the capability to illuminate and image at very high angles of incidence. The relationships between the numerical aperture in air and the angle of incidence to the sample are that:

$NA = n * \sin(\text{angle of incidence})$ where the index n has a value of 1.000 for air.

The following table summarizes the relation between NA and the angle of incidence in air:

| NA (in air) | Angle of incidence (degrees) |
|---|---|
| 0.90 | 64 |
| 0.91 | 66 |
| 0.92 | 67 |
| 0.93 | 68 |
| 0.94 | 70 |
| 0.95 | 72 |
| 0.96 | 74 |
| 0.97 | 76 |
| 0.98 | 79 |
| 0.99 | 82 |

FIG. 17 is a 0.97 NA design having a 1 millimeter field size. The design is optimized for a 266 nm wavelength and uses only fused silica. The system has a Strehl ratio of 0.98 and can resolve on the order of 6,000 spots along one dimension of the 1 mm field. As will be discussed below, increased field sizes are achievable using this system. For a 1.5 mm field size, the Strehl ratio decreases to 0.95 and the number of resolvable spots along one dimension of the field increases to approximately 9,000. For a 2.0 mm field size, the Strehl ratio decreases to 0.85 and the number of resolvable spots along one dimension of the field increases further to approximately 12,000. An increase in the number of resolvable spots increases the efficiency for a given configuration and faster inspection of an object is possible. Possible applications of this optical system include wafer and photomask inspection, material masking and cutting operations, UV lithography, biological microscopy, metallurgical microscopy and others.

Note that the elements of FIG. 17 are drawn to scale, with the number and line in the upper left corner indicating a distance in millimeters, here 25 millimeters. This notation is used throughout several figures included herein.

The design in FIG. 17 includes a catadioptric group 1701 proximate to an intermediate image, and a focusing optics group 1702. Light scattered, diffracted, and reflected by the object 1704 is collected by the catadioptric group 1701 which forms an intermediate image 1707. The focusing optics group 1702 corrects for the aberrations present in the intermediate image. The working distance of the design presented in FIG. 17 is approximately 0.5 millimeters, or a distance of approximately 0.5 millimeters exists between the object 1704 and the single refractive element 1705. The central obscuration is limited to 10 percent of the beam diameter.

From FIG. 17, catadioptric group 1701 includes near flat reflector with a reflective surface coating 1705 and a dome-shaped reflector 1706. The near flat reflector with a reflective surface coating 1705 can be a parallel fused silica plate having zero power. Focusing optics group 202 includes first focusing lens element 1709, second focusing lens element 1710, third focusing lens element 1711, fourth focusing lens element 1712, fifth focusing lens element 1713, sixth focusing lens element 1714, seventh focusing lens element 1715, and eighth focusing lens element 1716. The focusing optics group 1702 corrects for high order spherical aberration and coma. The focusing optics group design uses a field lens concept originally developed by Offner, but the Offner design only works for systems having near zero field size. The large fields in these objective designs require unique optimization techniques. The complexity and shapes of the lenses in the focusing group 1702 become extremely critical for high NA values, such as those exceeding 0.90, and for large field sizes.

The ultra high NA disclosed allows for a variety of flexible illumination schemes. Illumination angles from 0 to 85 degrees can be implemented, thereby allowing maximum flexibility when choosing an illumination angle.

Figure 18:
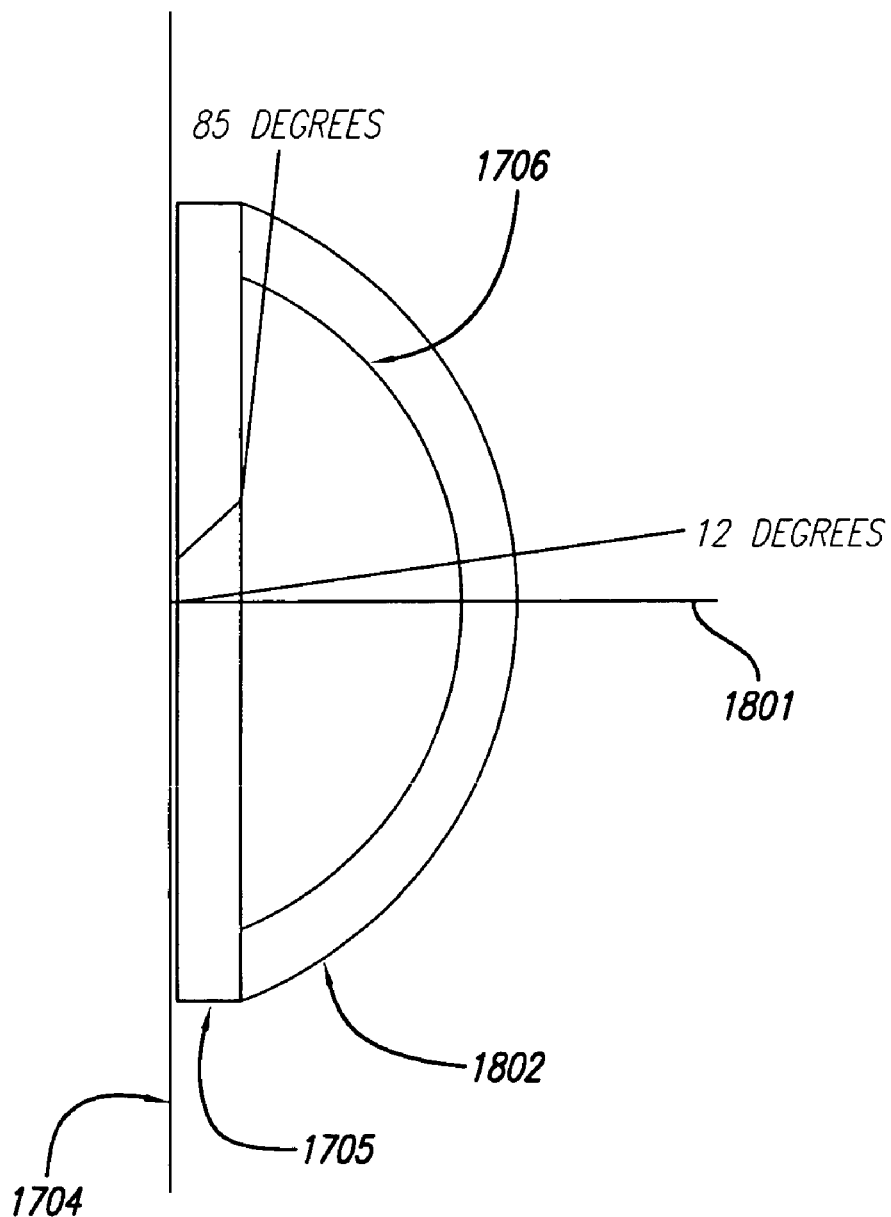
FIG. 18 is a cutaway side view of dome-shaped reflector and the fused silica lens mirror element.
Figure 19:
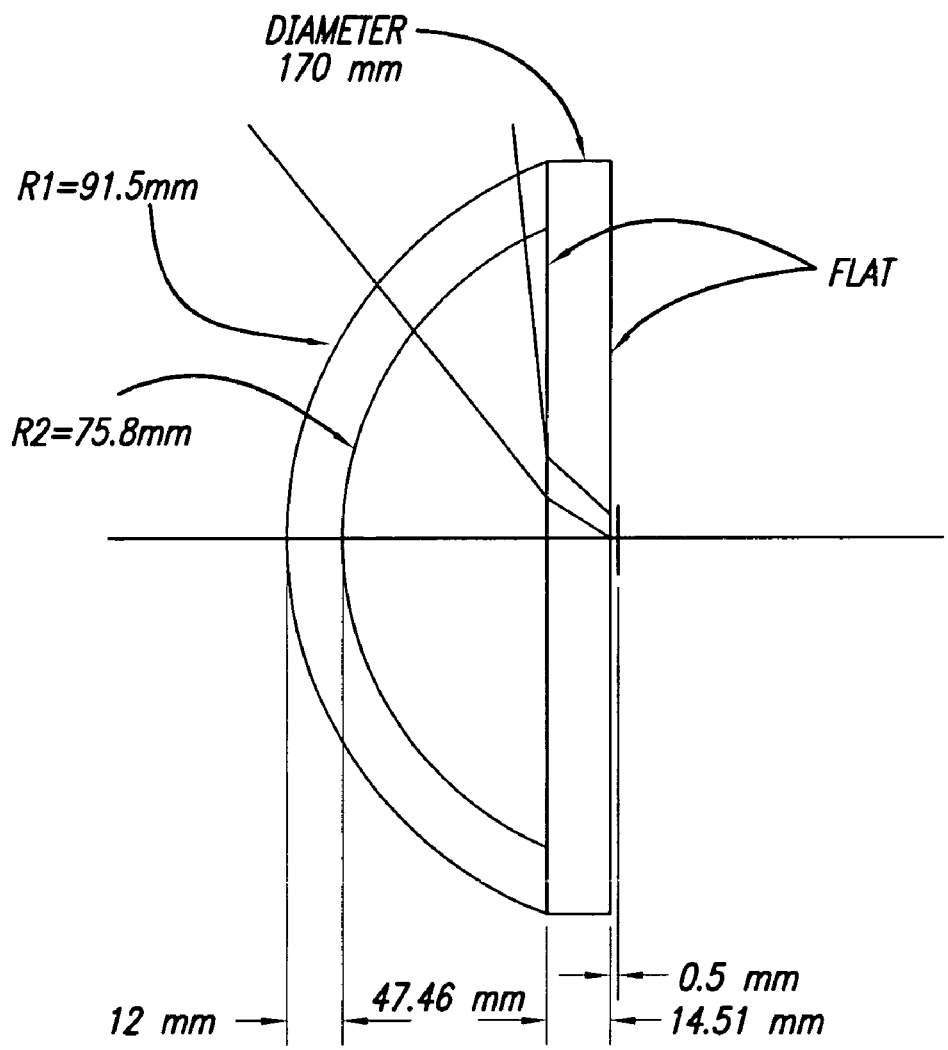
FIG. 19 illustrates the dimensions of the catadioptric group in one aspect.

The catadioptric optical system has two primary methods for illumination. First, light energy can enter through the lenses of the optical system at angles from 0 to the angle defined by the objective NA. Second, for oblique illumination at angles from about 12 to 85 degrees, the preferred method is by introducing the illumination through an aperture in the coating of the dome-shaped reflector as shown in FIG. 18. As a result, illuminating light only passes through a few surfaces, thereby reducing the potential for multiple surface reflection and scattering to reach the imaging detector. As shown therein, a beam introduced through an aperture in the mirror coating 1706 maintains the same angle with respect to the wafer 1704 when it exits the objective. In other words, illumination introduced at an angle of 85 degrees to the normal 1801 exits the fused silica single refractive element 1705 at the same 85 degree angle. For the lens design shown in FIG. 17, the dimensions for the catadioptric group to provide uniform angles of incidence are as shown in FIG. 19. The thickness of fused silica near flat reflector 1705 is 14.51 mm with a diameter of 170 mm. The dome-shaped reflector 1706 has an inner radius of curvature of 75.8 mm, and an outer radius of curvature of 91.5 mm. The distance on the centerline between the inner edge and the outer edge of the dome-shaped reflector 1706 is 12 mm, and the distance from the inner edge of the dome-shaped reflector to the fused silica near flat reflector 205 is 47.46 mm.

If the design is reoptimized by changing the thickness or radius of curvature of the near flat reflector 1705 or the inner radius of the dome-shaped reflector 1706, the thickness and/or outer radius of curvature 1802 of dome-shaped reflector 1706 may be modified to preserve the angle of illumination. Under oblique illumination, in addition to preserving the angle when a beam enters and exits the objective, the catadioptric elements do not introduce any power to the illumination beam. A collimated beam of light energy entering through an aperture in a mirror coating will be collimated when it exits the objective. The aperture in coating of the dome-shaped reflector 1706 may include a slit of non-mirrored surface, single holes of non-mirrored surface, a physical hole in the mirror, a partial mirror coating, or a coating that selectively transmits the wavelength of interest. In addition, multiple beams at multiple angles may also be used for illumination. For example, using oblique illumination, two beams separated azimuthally by approximately 90 degrees may be used for illumination to minimize shadowing effects.

The catadioptric imaging system effectively collects light scattered, diffracted, and reflected at different angles by the object and maps these scattering angles to a plane. This plane is located at the pupil of the system and each position on this pupil plane corresponds to a position on the dome-shaped reflector 1706. Each location in the pupil plane corresponds to different scattering angles, and apertures placed at this pupil plane can be used to limit the range of scattering angles reaching the image detector. This pupil plane roughly corresponds to the Fourier plane of the object. Such a system supports collection NAs up to 0.99 for illumination angles between 0 and 85 degrees.

The wide range of illumination and collection angles possible with this catadioptric optical system allows it to support multiple imaging modes. These modes include, but are not limited to, variable NA bright field, full sky, ring dark field, inverted ring dark field, directional dark field, double dark field, central dark ground, Manhattan geometry, confocal bright field, confocal dark field, as well as conoscopic imaging. Many other schemes are also possible in which the illumination angle is between 0 and approximately 85 degrees and the collection angle between 0 and approximately 82 degrees.

Figure 26:
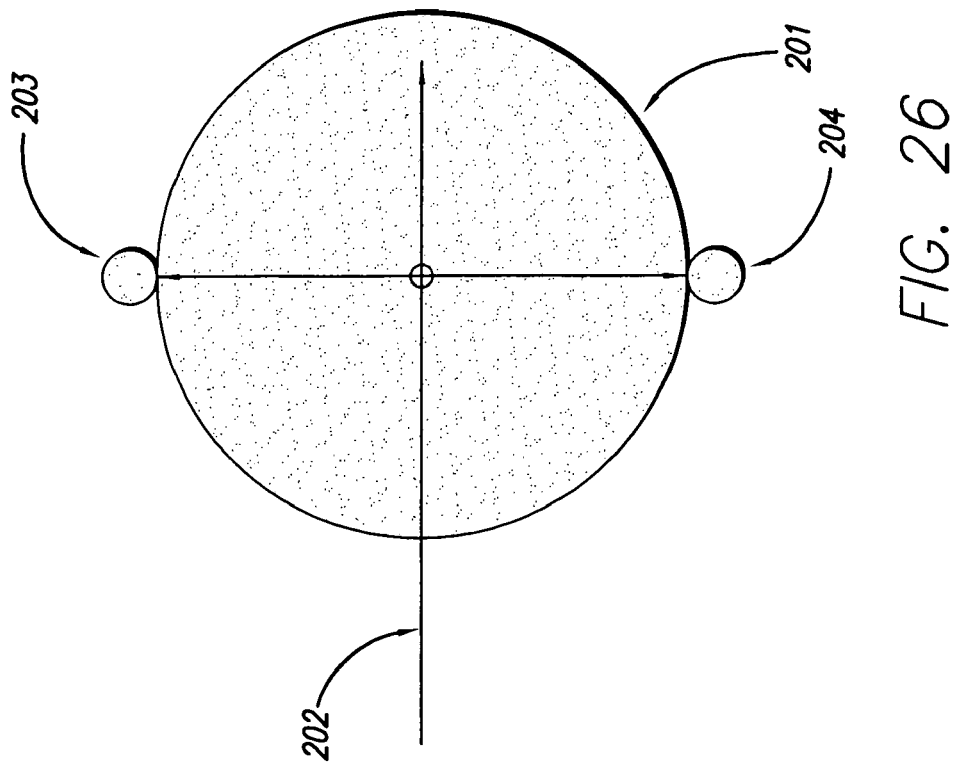
FIG. 26 is a top view of the double dark field system.
Figure 25:
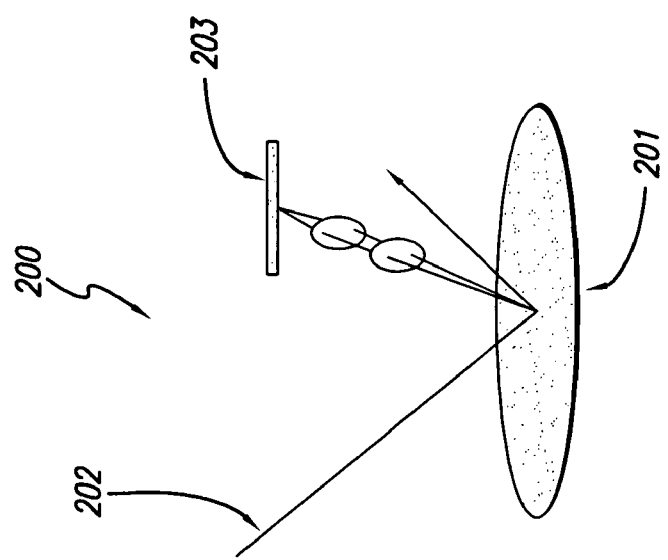
FIG. 25 illustrates a side view of a double dark field design system that illuminates the object at a relatively high angles of incidence.

FIGS. 25 through 28 illustrate illumination of the specimen, such as a wafer surface, using dark field illumination. FIG. 25 is side view of a double dark field design system 200 that illuminates the object 201 using laser beam 202 directed at a relatively low angle of incidence. Collectors 203 and 204 are mounted at different angles from the laser beam 202, typically 90 degrees. FIG. 26 illustrates a top view of the system with the collectors 203 and 204 mounted 180 degrees from one another and 90 degrees from the laser 202. Variations of these angles are possible. This provides enhanced collection capability and allows detection of particular object faults. FIG. 27 illustrates a variation of a central dark ground imaging system 300, wherein the laser beam 301 passes through the collector 302 at an approximately perpendicular angle to the object 303. The light beam strikes the object and is diverted, depending upon the features encountered, toward various collectors mounted about the object. Four collectors 305–308 in FIG. 28 have been employed in the past, each at an angle 90 degrees from the nearest collectors, as shown in FIG. 3b. Different numbers of collectors may be used at various angles depending upon the type of object scanned and the defects anticipated.

Variable NA bright field mode may be employed using the concepts disclosed herein. The illumination of the object in this system is similar to that in a standard microscope. The light may be injected into the optical system using a beam splitter and then projected through the focusing group 1702. Light energy then passes through the aperture in the dome-shaped reflector 1706 and strikes the reflective surface on near flat reflector 1705. Light energy then passes back through the near flat reflector 1705, striking dome-shaped reflector 1706, passing once again through the near flat reflector 1705 to illuminate object 1704. Note that the right surface of the near flat reflector 1705 shown in FIG. 17 is necessarily clear, or non-opaque, at the center portion such that light may contact object 1704 but has a reflective interior surface outside the center portion to provide reflectivity. Variable illumination NA can be obtained by using an aperture at the objective pupil plane, in the collimated range of the objective, or in separate optics before the beam splitter. The light passes through the objective and is then scattered, diffracted, and reflected from the object. The light from the object returns through the objective and through the beam splitter. The variable NA of the light from the object can be obtained by using an aperture at the objective pupil plane or in the collimated range of the objective. An image is formed on a detector using additional lenses as described below. Narrow band illumination may be employed. The bright field illumination could be a narrow band laser or a broad band source with a narrow band filter. To reduce the problem of speckle and interference from narrow band light, a moving ground glass or some other technique to introduce random phase may be placed into the beam before light enters the objective. Other speckle reduction techniques are disclosed below.

Alternately, the system can operate in full sky mode. This mode is a variation of the variable NA bright field mode described above. Full sky uses the same type of variable NA illumination, however, the NA of the light collected from the object should be as large as possible. Imaging in this mode collects as much light as possible coming from the object, especially in the higher angles. Full sky mode can minimize contrast variations introduced by grain and rough films.

The system can also operate in ring dark field mode. This is a standard type of dark field imaging where the illumination angles are limited to a high NA ring and the imaging angles are limited to the NAs less than those used by the ring illumination. The ring illumination can be injected into the optical system using a beam splitter. The ring illumination can be formed by a ring reflector or by separate illumination optics previous to a beam splitter. To form the high NA ring in the separate illumination optics an aperture can be placed at an equivalent pupil plane. This method of forming the ring illumination can have the aperture block a substantial portion of the light. To avoid this, the ring can be formed by using one or more axicons, a diffractive optic, a holographic optic, a segmented optic, combinations of these devices, and so forth. The low NA imaging can be obtained by placing an aperture at the pupil plane of the objective to limit the angles reaching the detector.

Alternately, the system can operate in inverted ring dark field mode. This mode is the inverse of ring dark field mode and uses the low NAs for illumination and a high NA ring for imaging. Variable low NA illumination can be obtained by using a low NA spot mirror or separate illumination optics before the beam splitter as described in the variable NA bright field section above. High NA imaging can be obtained by placing an aperture at the pupil plane of the objective or in the collimated range to limit the angles reaching the detector.

Figure 20:
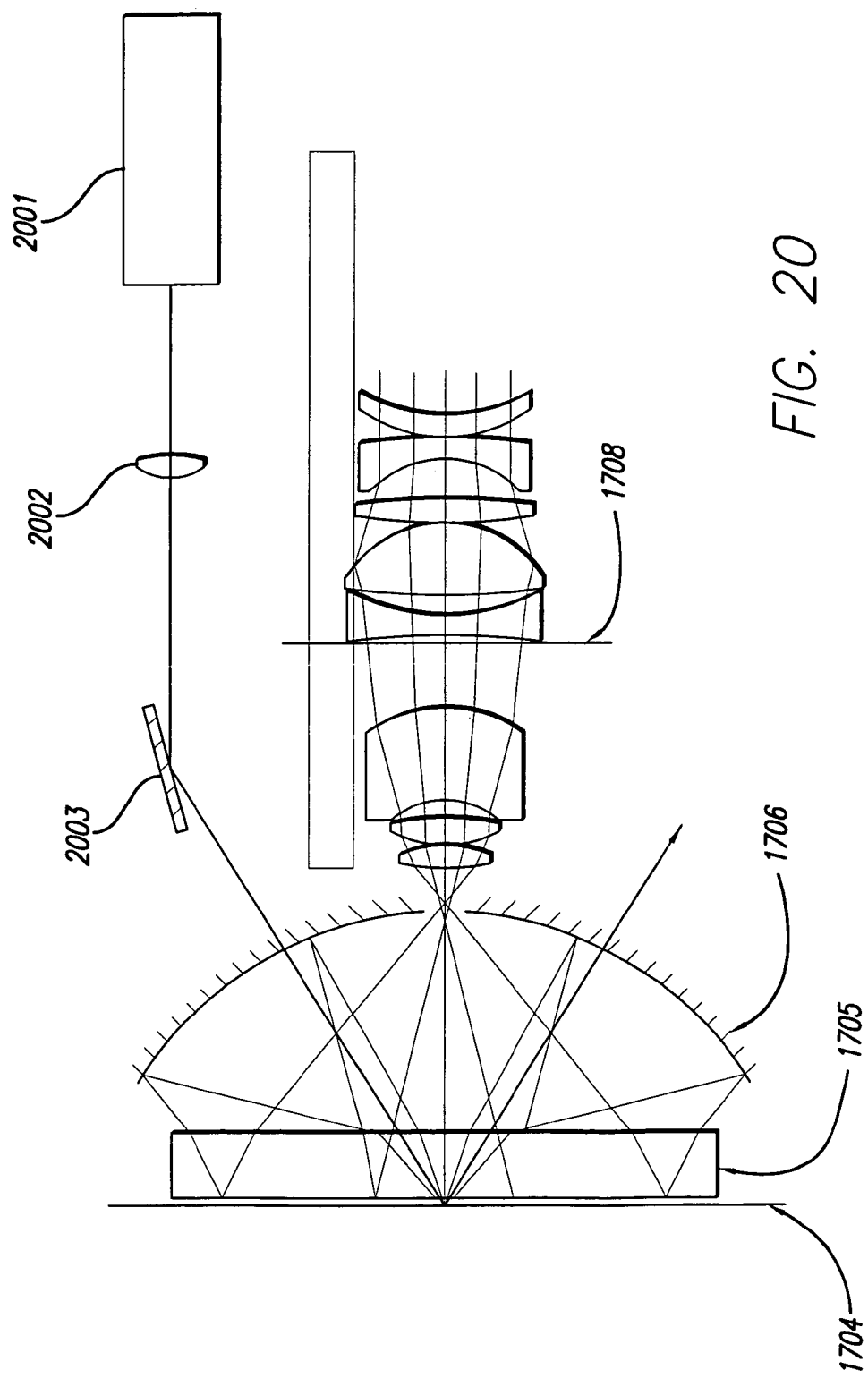
FIG. 20 presents a catadioptric dark field imaging system and having a variable angle of incidence from an illumination source.

The system can also operate in directional dark field mode using oblique illumination, as shown in FIG. 20. Such an implementation can collect scattered and diffracted light from the object at variable NAs from the near normal portion of light to the full angular range of the catadioptric objective. In the directional dark field mode, the system illuminates the object by injecting the illuminating beam through an aperture in the mirror coating shown in FIG. 20. Illumination source 2001 emits a beam of light to lens 2002, which collimates the beam and transmits the beam to mirror 2003. Mirror 2003 directs the collimated beam through the dome-shaped reflector 1706, striking the near flat reflector 1705 and the object 1704. The specular reflection from object 1704 is transmitted out of the system through another aperture in the coating of the dome-shaped reflector 1706. The scattered and diffracted light from the object 1704 is collected by the dome-shaped reflector 1706. The dome dome-shaped reflector 1706 then reflects the light to lens mirror element 1705 which in turn reflects the light to the imaging lenses in the system. Limiting the collection angles of the scattered and diffracted light is accomplished by using an aperture in the pupil plane or in the collimated range of the objective.

Figure 21:
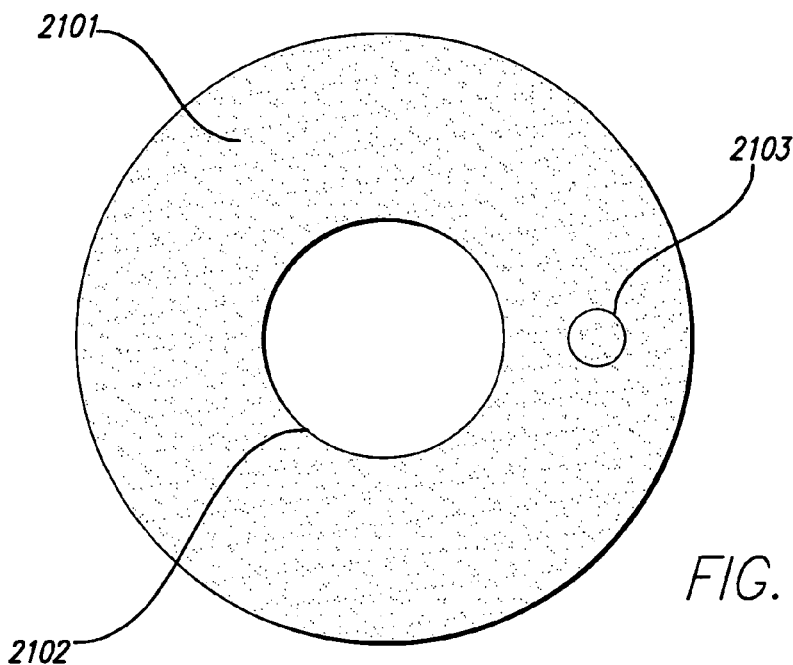
FIG. 21 is a pupil aperture that may be used with the catadioptric system when selecting the directional dark field mode.

Apertures of any size may be used from large apertures that substantially transmit the full NA of the system to small apertures that substantially transmit only the near normal light. FIG. 21 is an example of a pupil aperture 2101 that allows imaging light to pass through the central region 2102 and blocks light outside this area with annular block. Such an aperture can be used to limit collection angles to those less than the illumination angle.

Figure 22:
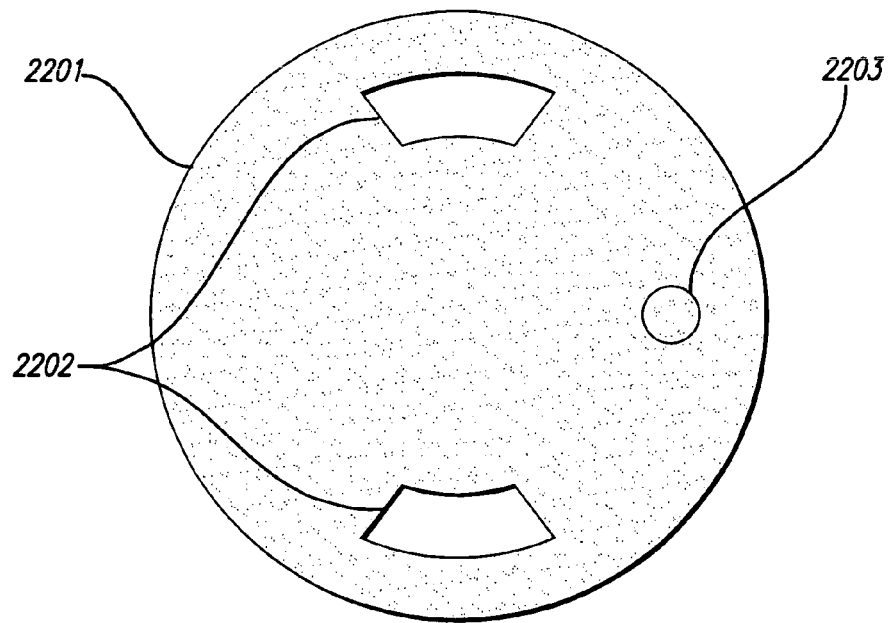
FIG. 22 presents an aperture that may be used with the catadioptric system when selecting the double dark field mode.

The system can further operate in double dark field mode using the oblique illumination and collecting the near 90 degree azimuthal portions of scattered and diffracted light. In the double dark field mode, the system illuminates the object by injecting the illumination through an aperture in the mirror coating as is done in the directional dark field case. The system uses an aperture in the pupil plane or in the collimated range to limit the collection to the near 90 degree azimuthal portions of scattered and diffracted light. Such a collection aperture may be as shown in FIG. 22. The aperture 2201 illustrated in FIG. 22 has two apertures 2202 which collect the near 90 degree azimuthal scattering of a double dark field system.

Figure 23:
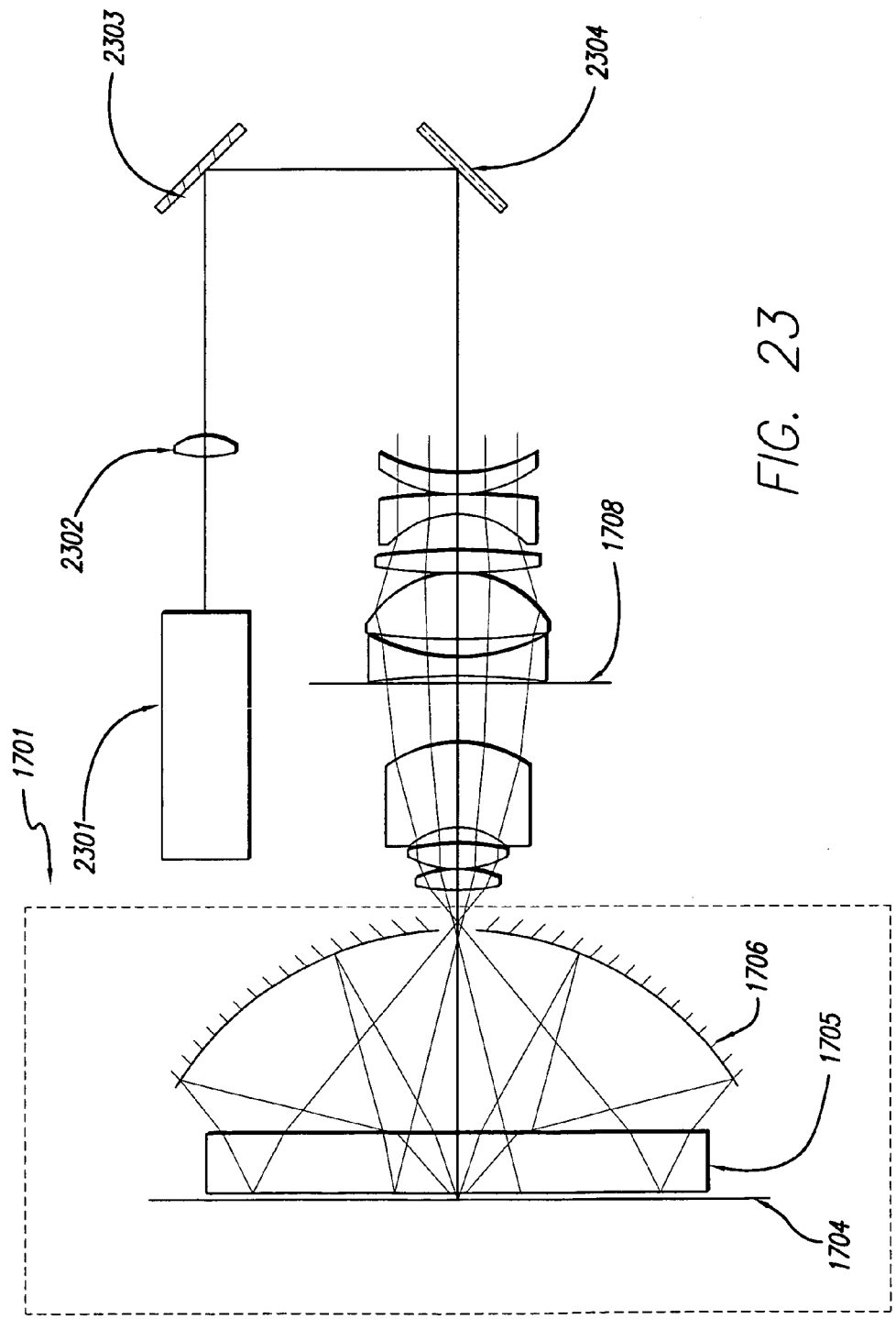
FIG. 23 illustrates operation in the central dark ground mode using normal illumination.

Additionally, the system can operate in the central dark ground mode using normal illumination illustrated in FIG. 23. In FIG. 23, illumination source 2301 emits a beam of light to lens 2302, which compensates for the power in the focusing optics group 202 and transmits the beam to mirror 2303. Mirror 2303 directs the beam toward a spot mirror 2304, which directs the beam through the focusing optics group 1702 and into the catadioptric group 1701. The beam strikes the near flat reflector 1705 at an angle from approximately 0 to 12 degrees from the normal of the near flat reflector 1705 then strikes the object 1704. The scattered, diffracted, and reflected light from the object 1704 is collected by the dome-shaped reflector 1706. The dome-shaped reflector 1706 then reflects the light to lens mirror element 1705 which in turn reflects the light to the imaging lenses in the system. In this mode the specular reflection from the object is blocked and remaining portions of the scattered and diffracted light are transferred to the detector. The specular reflection can be blocked by the spot mirror 2304 or by an aperture placed in the pupil plane or the collimated range.

Figure 24:
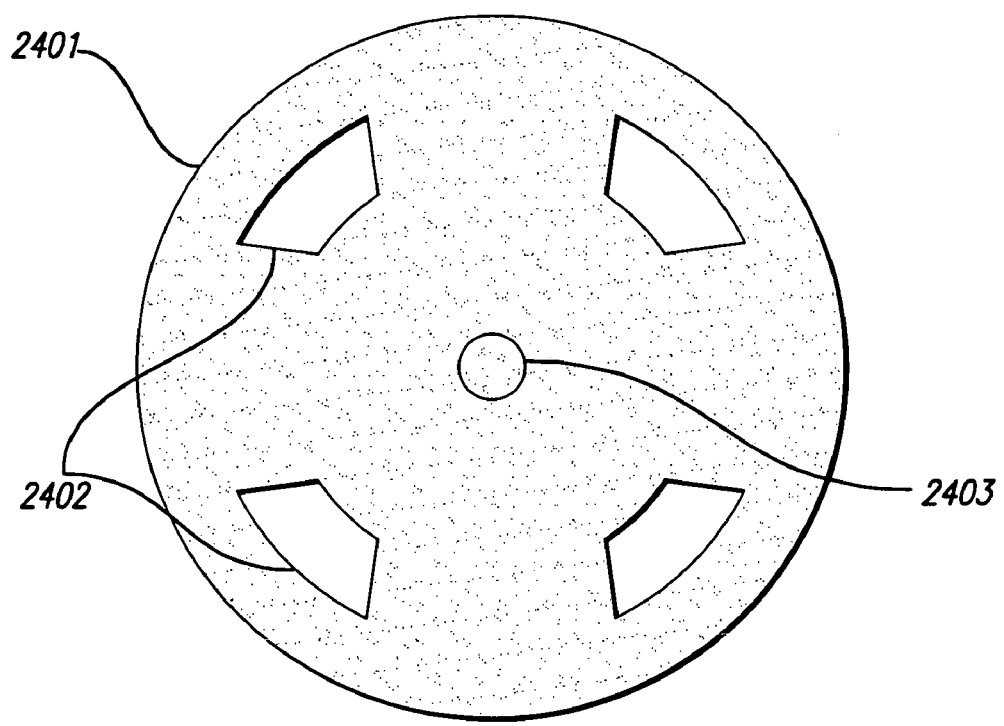
FIG. 24 illustrates an aperture that may be used with the catadioptric system when selecting the Manhattan geometry mode.

The system can also operate in the Manhattan geometry mode. This mode can use normal illumination as described in the central dark ground mode or oblique illumination as described in the directional dark field mode. The Manhattan geometry uses high angle light collection from four different quadrants. An aperture that provides this type of collection may be as shown in FIG. 24. FIG. 24 is a filter 2401 having four apertures 2402 for capturing high angle scattering in portions of the four separate quadrants. Such a filter may be used in connection with a system as shown in FIGS. 27 and 28.

Additionally, the system disclosed herein can operate in the bright field confocal imaging mode. This mode takes advantage of the short depth-of-focus obtainable by using a high NA objective and short wavelength illumination. Bright field confocal mode illuminates the object with a single point or a line focus. The illumination spot on the object is then imaged through an aperture in front of a detector. This aperture and detector can be a pinhole and a single point detector, in the case of a single point focus, or a slit and a linear detector array, in the case of a line focus. The object, illumination spot, aperture, or a combination thereof is then scanned to collect information about an area on the object being examined.

Additionally, the system can operate in the dark field confocal imaging mode. Dark field confocal imaging mode also takes advantage of the short depth-of-focus obtainable by using a high NA objective and short wavelength illumination. This is a unique imaging mode is made possible by the high NA diffraction limited illumination. High NA ring illumination produces a diffraction limited spot or line and the remaining NA can support diffraction limited imaging. For example, the illumination can occupy a ring from 0.9 to 0.97 NA and the NA up to 0.9 can be used for imaging. The illumination spot on the object is imaged, using an NA that is less than the illumination NA, through an aperture in front of a detector. This aperture and detector can be a pinhole and a single point detector, in the case of a single point focus, or a slit and a linear detector array, in the case of a line focus. The system scans the object, illumination spot, aperture, or a combination thereof to collect information about an area on the object being examined.

The system can alternately operate in the conoscopic mode. In this mode oblique illumination is used as described above in the section on directional dark field or normal illumination can be used as described in relation to central dark ground mode. In this mode lenses are not required to form an image on a detector. The light at the pupil plane or in the collimated range of the objective can be placed directly on a single detector, multiple detectors, or a detector array. An aperture limiting the range of angles reaching the detector can also be used at the pupil plane or in the collimated range prior to the detector. The portions of the pupil plane that are most sensitive to the features of interest can be selected for detection. This signal may then be compared to other similar signals form similar objects to detect changes in the features on the object.

As may be appreciated from the previous paragraphs, the concept disclosed herein is that multiple imaging modes can be implemented using a single optical system or machine in connection with the excimer laser illumination device. The ultra high NA disclosed for illumination and collection permits the implementation of imaging modes using the same optical system, thereby allowing optimization of imaging for different types of defects or samples. Illumination angles from 0 to 85 degrees can be easily implemented, thereby allowing maximum flexibility when choosing an illumination angle. Collection angles from 0 to 82 degrees are possible.

Further, it should be noted that oblique dark field illumination through the dome-shaped reflector in the modes disclosed herein does not interfere with image pupil filtering. This dark field illumination can be achieved through an aperture in the mirror coating with the entrance angle being the same angle striking the object. This feature permits the illumination and imaging pupils to be separate from one another, and thus the illumination and imaging pupil do not interfere with one another. The unique oblique illumination scheme used in the different dark field modes renders the catadioptric system disclosed herein much more flexible with respect to desired illumination schemes and aperturing and filtering techniques.

FIGS. 21, 22, and 24 are some examples of different pupil apertures that may be used to select different imaging modes. As with all mode selection apertures illustrated, these may be fabricated from a section of clear glass with appropriate portions, such as annular block 2103, screened out using an opaque material, such as paint or other non-transparent material. Other means of forming such filters, such as using metal or composite material, may be used while still within the scope of the current system.

A liquid crystal device, micro-mirror array, or some other addressable array device can be used to segment the pupil. For example, a liquid crystal array can be placed at the pupil plane. Portions of the array can be made opaque and other portions transparent to correspond to the desired pupil aperture, such as those in FIGS. 21, 22, and 23.

The dimensions for the system illustrated in FIG. 17 are as follows, where the surface numbers 0 through 26 track the surfaces and gaps the light passes through and reflects off in performing the different imaging modes:

This is an all fused silica design with a 0.97 NA, 1.0 mm field size, and a 15.46 mm focal length. This design is for use at a wavelength of 0.266 micrometers where the index of fused silica is 1.499776.

| | Aperture (mm) | Surface Radius (mm) | Thickness (mm) | Radius | [element] Material |
|---|---|---|---|---|---|
| 0 | | — | 1.0917e+20 | 3.5297e+18 | Air |
| 1 | [3216] | −33.497056 | 5.689687 | 18.000000 | Fused Silica |
| 2 | [3216] | −32.189281 | 0.100000 | 19.000000 | Air |
| 3 | [3215] | 196.880765 | 4.000000 | 19.000000 | Fused Silica |
| 4 | [3215] | 25.684572 | 6.560210 | 17.000000 | Air |
| 5 | [3214] | 357.899464 | 5.000000 | 19.000000 | Fused Silica |
| 6 | [3214] | −90.078811 | 0.100000 | 19.000000 | Air |
| 7 | [3213] | 24.037819 | 12.750000 | 20.500000 | Fused Silica |
| 8 | [3213] | 432.836029 | 5.920196 | 20.500000 | Air |
| 9 | [3212] | −40.013173 | 3.250000 | 19.500000 | Fused Silica |
| 10 | [3212] | — | — | 20.500000 | Air |
| 11 | [3208] | — | — | 35.000000 | Aperture stop |
| 12 | | — | 10.624120 | 35.000000 | Air |
| 13 | [3211] | 26.394355 | 20.000000 | 17.500000 | Fused Silica |
| 14 | [3211] | 19.724315 | 4.038458 | 12.000000 | Air |
| 15 | [3210] | 128.412673 | 9.508548 | 12.500000 | Fused Silica |
| 16 | [3210] | −24.741473 | 0.100000 | 12.500000 | Air |
| 17 | [3209] | 21.128369 | 4.000000 | 9.5000000 | Fused Silica |
| 18 | [3209] | −155.179382 | 10.50000 | 9.5000000 | Air |
| 19 | [3206] | — | 47.457785 | 0.122526 | Air |
| 20 | [3205] | — | 14.508002 | 58.000000 | Fused Silica |
| 21 | [3205] | — | −14.508002 | 58.000000 | Reflect. |
| 22 | [3205] | — | −47.457785 | 58.000000 | Air |
| 23 | [3206] | 75.786086 | 47.457785 | 64.000000 | Reflect. |
| 24 | [3205] | — | 14.508002 | 58.000000 | Fused Silica |
| 25 | [3205] | — | 0.5000000 | 58.000000 | Air |
| 26 | | — | 0.500543 | | |

Surface 26 represents the gap distance between near flat reflector 1705 and object 1704. Note that surface 11 represents the aperture allowing light to pass from surface 10 on element 1712, and surface 12 represents the size of the air gap between within focusing group 1702.

Figure 29:
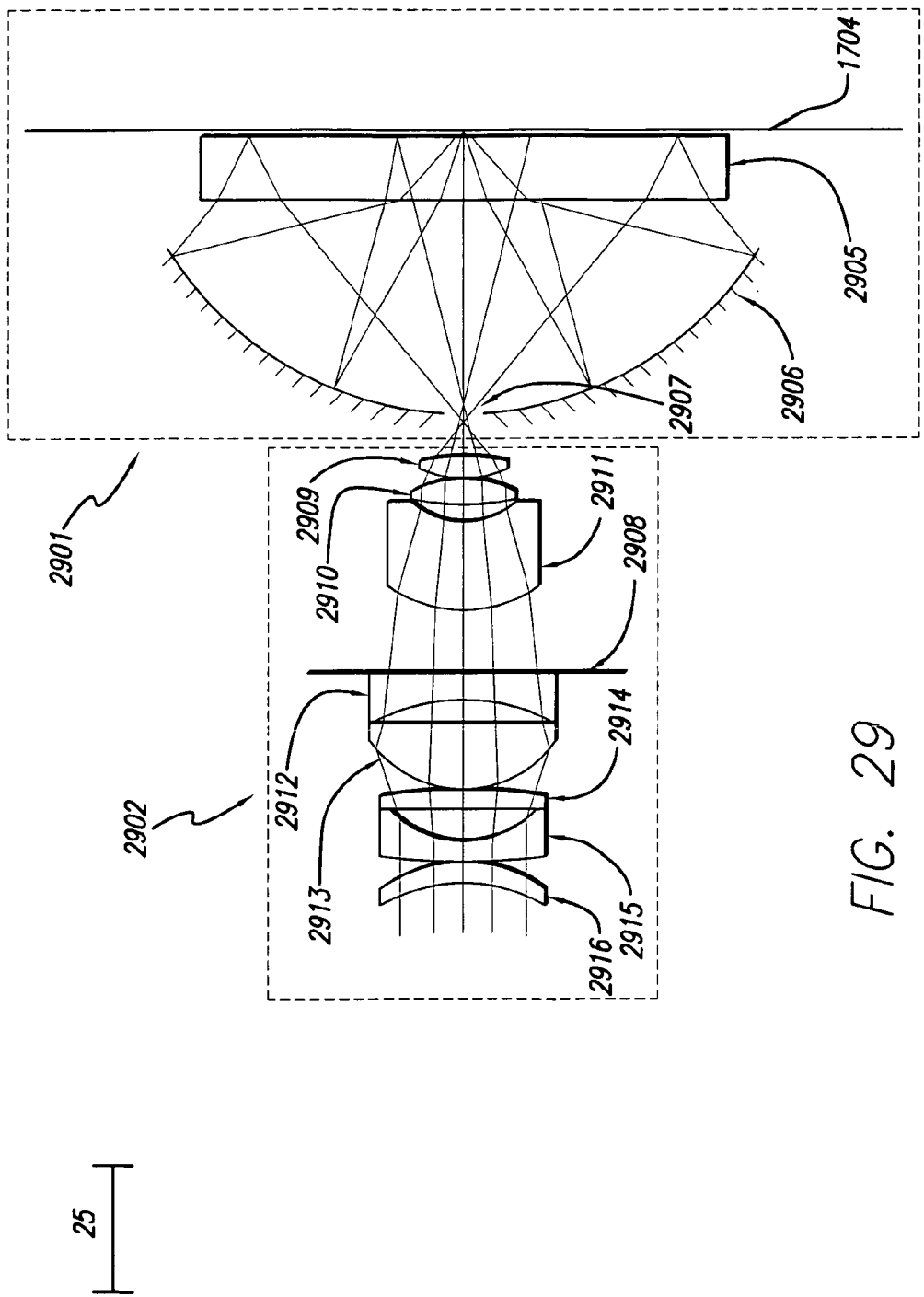
FIG. 29 is a multimode catadioptric dark field imaging system constructed to have a 0.98 NA.

An alternative aspect of this system may include higher NA values, an example of which is illustrated in FIG. 29. This aspect of the system is optimized for use at 0.98 NA. Note that the system of FIG. 29 uses the same basic components and configuration as that shown in FIG. 17, using a 0.98 NA catadioptric group 2901 and a 0.98 NA focusing optics group 2902. As may be appreciated from the figure and the following table, the system components or surfaces are similar to the 0.97 NA system, with some slightly differing surface curvatures and spatial separations between the elements.

Dimensions for the system of FIG. 29 are as follows (with surface numbering similar to that from the table and drawing of FIG. 2):

This aspect of the system is an all fused silica design with a 0.98 NA, 1.0 mm field size, and a 15.31 mm focal length. This design is for use at a wavelength of 0.266 micrometers where the index of fused silica is 1.499776.

| Aperture (mm) | Surface Radius (mm) | Thickness (mm) | Radius | [element] Material |
|---|---|---|---|---|
| 0 | — | 1.0917e+20 | 3.5661e+18 | Air |
| 1 | [2916] | −34.690724 | 5.000000 | 18.000000 | Fused Silica |
| 2 | [2916] | −32.508483 | 0.100000 | 19.000000 | Air |
| 3 | [2915] | 251.168193 | 4.000000 | 19.000000 | Fused Silica |
| 4 | [2915] | 25.262657 | 6.670812 | 17.250000 | Air |
| 5 | [2914] | 512.120638 | 5.000000 | 19.000000 | Fused Silica |
| 6 | [2914] | −85.950636 | 0.100000 | 19.000000 | Air |
| 7 | [2913] | 24.030210 | 13.002285 | 21.000000 | Fused Silica |
| 8 | [2913] | 386.838892 | 6.258149 | 21.000000 | Air |
| 9 | [2912] | −38.824067 | 3.250000 | 19.750000 | Fused Silica |
| 10 | [2912] | — | — | 20.500000 | Air |
| 11 | [2908] | — | — | 35.000000 | Aperture stop |
| 12 | | — | 13.615825 | 35.000000 | Air |
| 13 | [2911] | 28.596934 | 20.000000 | 18.000000 | Fused Silica |
| 14 | [2911] | 20.398707 | 3.564297 | 12.500000 | Air |
| 15 | [2910] | 53.168289 | 8.560685 | 13.500000 | Fused Silica |
| 16 | [2910] | −25.471785 | 0.100000 | 13.500000 | Air |
| 17 | [2909] | 24.150867 | 3.564297 | 10.000000 | Fused Silica |
| 18 | [2909] | −265.293182 | 10.00000 | 10.000000 | Air |
| 19 | [2906] | — | 47.439408 | 0.422526 | Air |
| 20 | [2905] | — | 14.890298 | 60.000000 | Fused Silica |
| 21 | [2905] | — | −14.890298 | 60.000000 | Reflect. |
| 22 | [2905] | — | −47.439408 | 60.000000 | Air |
| 23 | [2906] | 75.808460 | 47.439408 | 60.000000 | Reflect. |
| 24 | [2905] | — | 14.890298 | 66.000000 | Fused Silica |
| 25 | [2905] | — | 0.5000000 | 60.000000 | Air |
| 26 | | — | 0.500549 | | |

An additional aspect of the system is optimized for use at 0.99 NA. Note that the system of FIG. 30 uses the same basic components and configuration as that shown in FIG. 17, using a 0.99 NA catadioptric group 3001, and a 0.99 NA focusing optics group 3002.

As may be appreciated from the figure and the following table, the system components or surfaces are similar to the 0.97 NA system, with some slightly differing surface curvatures and spatial separations between the elements.

This aspect of the system is an all fused silica design with a 0.99 NA, 1.0 mm field size, and a 15.15 mm focal length. This design is for use at a wavelength of 0.266 micrometers where the index of fused silica is 1.499776.

Figure 30:
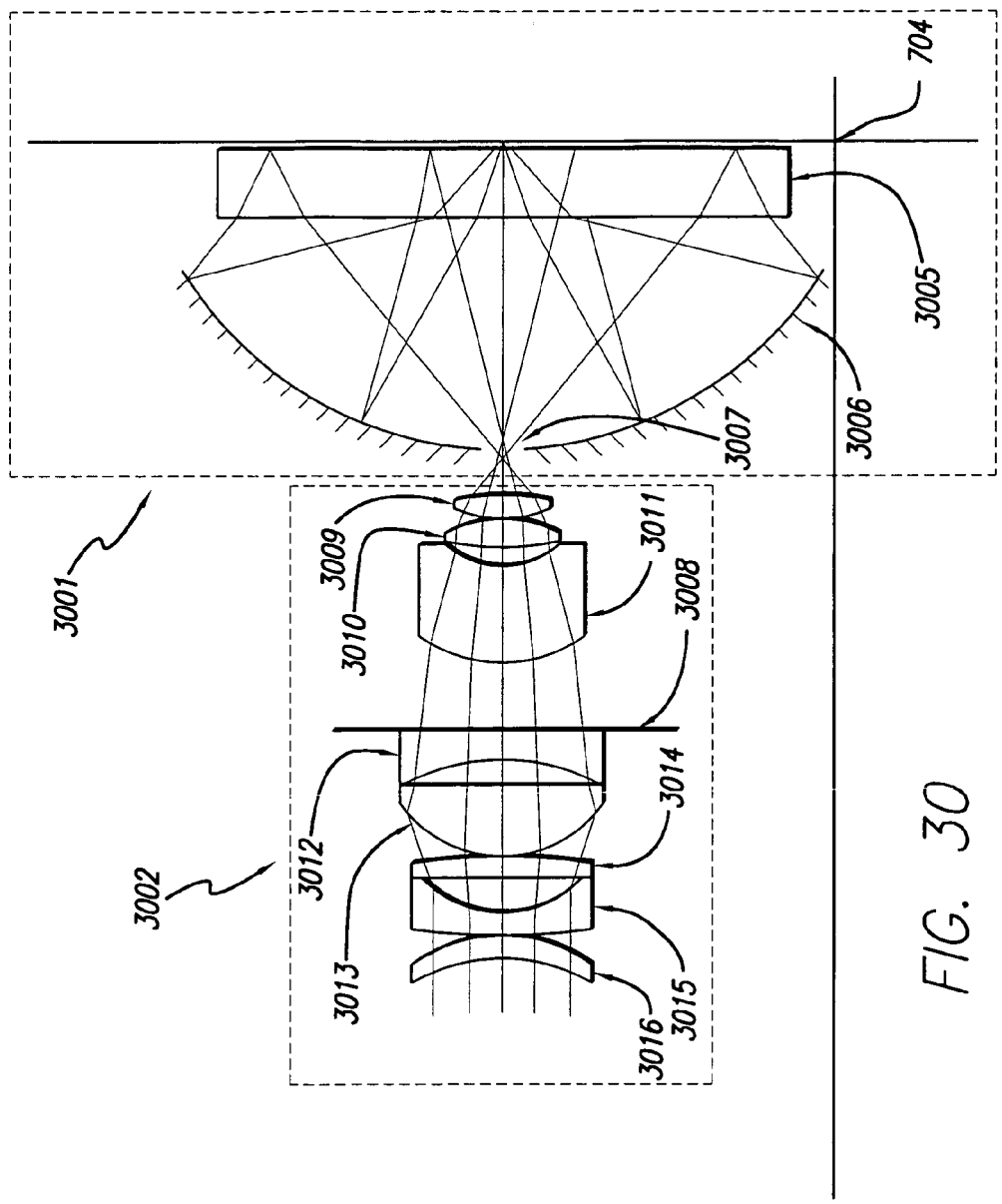
FIG. 30 is a multimode catadioptric dark field imaging system constructed to have a 0.99 NA.

Dimensions for the system of FIG. 30 are as follows (with surface numbering similar to that from the table and drawing of FIG. 17):

| Aperture (mm) | Surface Radius (mm) | Thickness (mm) | Radius | [element] Material |
|---|---|---|---|---|
| 0 | — | 1.0917e+20 | 3.6025e+18 | Air |
| 1 | [3016] | −35.203096 | 5.000000 | 18.000000 | Fused Silica |
| 2 | [3016] | −32.502313 | 0.100000 | 19.000000 | Air |
| 3 | [3015] | 222.523869 | 4.000000 | 19.000000 | Fused Silica |
| 4 | [3015] | 24.420515 | 6.583213 | 17.250000 | Air |
| 5 | [3014] | 262.694007 | 5.000000 | 19.000000 | Fused Silica |

-continued

| Aperture (mm) | Surface Radius (mm) | Thickness (mm) | Radius | [element] Material |
|---|---|---|---|---|
| 6 | [3014] | −125.012490 | 0.100000 | 19.000000 | Air |
| 7 | [3013] | 24.105961 | 13.752435 | 21.000000 | Fused Silica |
| 8 | [3013] | 778.092175 | 6.309114 | 21.000000 | Air |
| 9 | [3012] | −38.092856 | 3.250000 | 20.000000 | Fused Silica |
| 10 | [3012] | — | — | 21.000000 | Air |
| 11 | [3008] | — | — | 35.000000 | Aperture stop |
| 12 | | — | 15.423856 | 35.000000 | Air |
| 13 | [3011] | 34.922533 | 20.000000 | 18.500000 | Fused Silica |
| 14 | [3011] | 22.960530 | 3.322518 | 13.500000 | Air |
| 15 | [3010] | 50.507026 | 7.000000 | 13.750000 | Fused Silica |
| 16 | [3010] | −24.636821 | 0.100000 | 13.750000 | Air |
| 17 | [3009] | 24.316233 | 4.000000 | 11.000000 | Fused Silica |
| 18 | [3009] | 2052.1 | 10.50000 | 11.000000 | Air |
| 19 | [3006] | — | 47.541690 | 0.122526 | Air |
| 20 | [3005] | — | 15.730439 | 64.000000 | Fused Silica |
| 21 | [3005] | — | −15.730439 | 64.000000 | Reflect. |
| 22 | [3005] | — | −47.541690 | 64.000000 | Air |
| 23 | [3006] | 76.143722 | 47.541690 | 68.000000 | Reflect. |
| 24 | [3005] | — | 15.730439 | 64.000000 | Fused Silica |
| 25 | [3005] | — | 0.5000000 | 64.000000 | Air |
| 26 | | — | 0.500832 | | |

Yet another aspect of the system is optimized for use at 0.97 NA with an approximately 4 mm field of view. Note that the system of FIG. 31 uses the same basic configuration as that shown in FIG. 17, using a catadioptric group 3101 and a focusing group 3102. As may be appreciated from the figure and the following table, the system components or surfaces are similar to the previous 1 mm field size systems, with some slightly differing surface curvatures and spatial separations between the elements.

Figure 31:
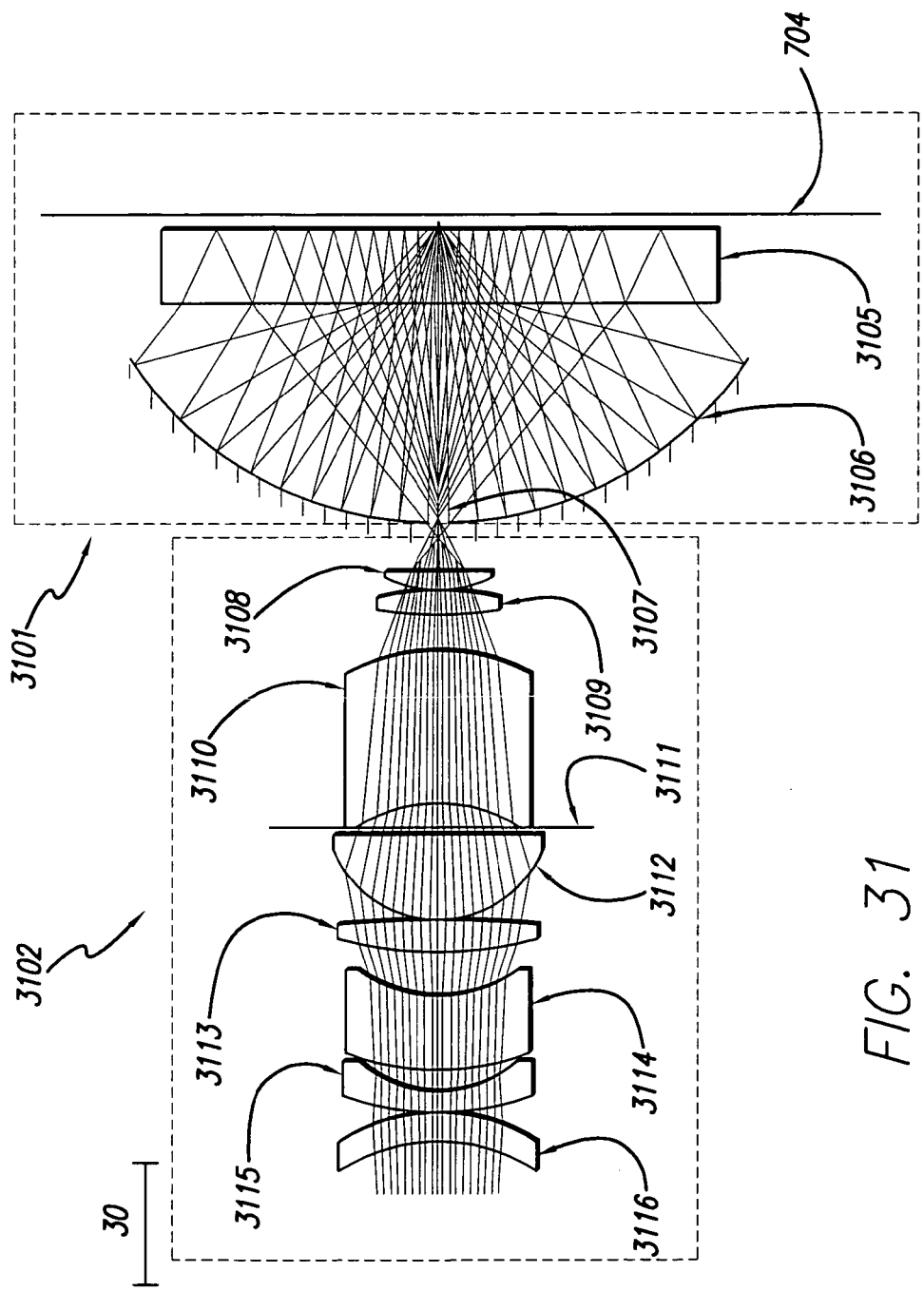
FIG. 31 is a system having increased field size, specifically approximately 4.0 millimeters.

An example of an imaging system having increased field size is illustrated in FIG. 31. As shown therein, nine lenses 3108–3117 contribute with a catadioptric group to increase field size to 4.0 mm for a 0.97 NA.

Aperture stop 3112 is located halfway through the lens arrangement. From FIG. 31, the ray spacing is unequal in the middle of the design, although the rays become equally spaced at the left side of the lens arrangement. This illustrates the one-to-one correspondence between the rays in the dome and the output plane. This ray spacing provides higher order correction capability. As the lens arrangement causes the ray spacing to be unequal on the strongly curved ninth surface (left surface on lens 3113), the rays encounter more spherical aberration on the ninth surface than normal, towards the edge of the aperture, and thereby provide the higher order spherical aberration needed to compensate for the catadioptric elements. The system illustrated in FIG. 31 has a Strehl ratio ranging from 0.50 to 0.73 over the 4.0 mm field size.

This aspect of the system is an all fused silica design with a 0.97 NA, 4.0 mm field size, and a 17.53 mm focal length. This design is for use at a wavelength of 0.266 micrometers where the index of fused silica is 1.499776.

Dimensions for the system of FIG. 31 are as follows (with surface numbering similar to that from the table and drawing of FIG. 17):

| Aperture (mm) | Surface Radius (mm) | Thickness (mm) | Radius | [element] Material |
|---|---|---|---|---|
| 0 | — | 1.0000e+20 | 1.1429e+19 | Air |
| 1 | [3116] | −49.313195 | 7.000000 | 26.000000 | Fused Silica |
| 2 | [3116] | −48.825209 | 0.100000 | 26.000000 | Air |
| 3 | [3115] | 75.954248 | 5.500000 | 25.000000 | Fused Silica |
| 4 | [3115] | 34.364908 | 5.563965 | 21.500000 | Air |
| 5 | [3114] | 80.813499 | 17.867130 | 24.000000 | Fused Silica |
| 6 | [3114] | 39.762098 | 10.928315 | 21.500000 | Air |
| 7 | [3113] | 102.036933 | 8.0000000 | 26.000000 | Fused Silica |
| 8 | [3113] | −255.018249 | 0.100000 | 26.000000 | Air |
| 9 | [3112] | 29.518372 | 21.076921 | 27.000000 | Fused Silica |
| 10 | [3112] | 2.8375e+03 | 1.775488 | 27.000000 | Air |
| 11 | | — | — | 40.000000 | |
| 12 | [3111] | — | 6.140712 | 40.000000 | Air Fourier plane |
| 13 | [3110] | −43.892944 | 39.000220 | 22.000000 | Fused Silica |
| 14 | [3110] | −48.033761 | 8.316604 | 24.000000 | Air |
| 15 | [3109] | 106.289831 | 6.000000 | 16.000000 | Fused Silica |
| 16 | [3109] | −68.034207 | 0.100000 | 16.000000 | Air |
| 17 | [3108] | 34.181630 | 4.500000 | 14.000000 | Fused Silica |
| 18 | [3108] | −1.0338e+04 | 12.00000 | 14.000000 | Air |
| 19 | [3107] | — | 55.056163 | 0.138656 | Air |
| 20 | [3105] | 5.4047e+03 | 19.061584 | 67.898763 | Fused Silica |
| 21 | [3105] | — | −19.061584 | 67.898763 | Reflect. |
| 22 | [3105] | 5.4047e+03 | −55.056163 | 67.898763 | Air |
| 23 | [3106] | 89.730011 | 55.056163 | 75.820285 | Reflect. |
| 24 | [3105] | 5.4047e+03 | 19.061584 | 67.898763 | Fused Silica |
| 25 | [3105] | — | 0.5000000 | 67.898763 | Air |
| 26 | [3104] | — | 2.005791 | | |

Figure 32:
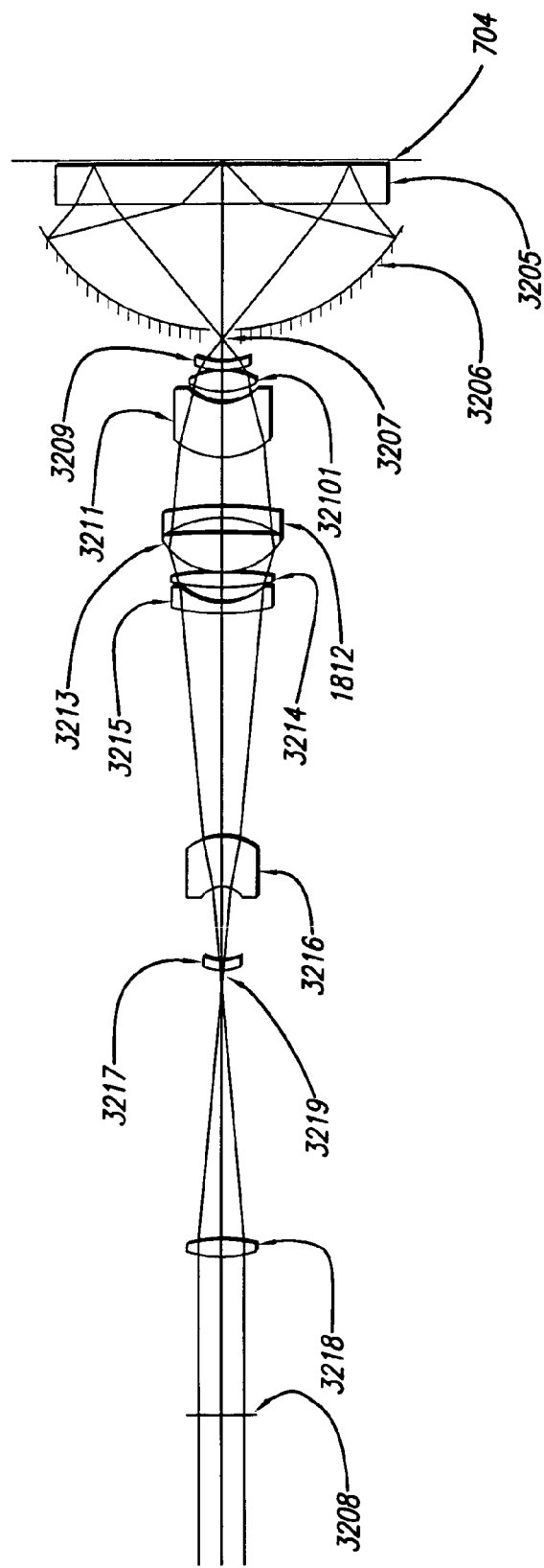
FIG. 32 presents a catadioptric system having a relayed pupil plane.

Yet a further aspect of the current design provides an external pupil plane conjugate to the internal pupil plane of the objective as shown in FIG. 32. This pupil plane will exactly correspond to the Fourier plane of the object because it is also in the collimated range of the objective. This external pupil plane allows for improved access to the Fourier plane for filtering and aperturing. The pupil plane is relayed, using a series of lenses 3209–3218 to an external plane 3208. The design has a 0.97 NA, 1.0 millimeter field diameter, and 0.5 millimeter working distance. The relayed pupil arrangement shown has a Strehl ratio greater than 0.90 and in the configuration shown a focal length of 12.37 millimeters.

The system of FIG. 32 has the following dimensions:

| Aperture (mm) | Surface Radius (mm) | Thickness (mm) | Radius | [element] Material |
|---|---|---|---|---|
| 0 | | — | 1.0000e+10 | 6.4667e+08 | Air |
| 1 | | — | — | 7.5000000 | Fourier Plane |
| 2 | [3208] | — | 62.515852 | 7.5000000 | Air |
| 3 | [3218] | 73.034166 | 5.000000 | 14.000000 | Fused Silica |
| 4 | [3218] | −93.305910 | 91.324812 | 14.000000 | Air |
| 5 | [3217] | 21.680281 | 4.0000000 | 8.5000000 | Fused Silica |
| 6 | [3217] | 51.554023 | 43.401528 | 8.5000000 | Air |
| 7 | [3216] | −10.644592 | 20.000000 | 8.5000000 | Fused Silica |
| 8 | [3216] | −19.624195 | 77.871853 | 14.000000 | Air |
| 9 | [3215] | 225.891254 | 4.0000000 | 18.000000 | Fused Silica |
| 10 | [3215] | 28.200709 | 5.753232 | 17.500000 | Air |
| 11 | [3214] | 383.158596 | 6.000000 | 19.000000 | Fused Silica |
| 12 | [3214] | −82.143752 | 0.100000 | 19.000000 | Air |
| 13 | [3213] | 26.7469644 | 14.000000 | 21.500000 | Fused Silica |
| 14 | [3213] | −185.222466 | 5.859221 | 21.500000 | Air |
| 15 | [3212] | −36.664980 | 4.000000 | 20.500000 | Fused Silica |
| 16 | [3212] | −135.155561 | 20.360279 | 21.000000 | Air |
| 17 | [3211] | 28.058433 | 20.0000000 | 18.000000 | Fused Silica |
| 18 | [3211] | 17.433830 | 4.434055 | 12.500000 | Air |
| 19 | [3210] | 34.161468 | 7.500000 | 12.500000 | Fused Silica |
| 20 | [3210] | −24.210328 | 0.100000 | 12.500000 | Air |
| 21 | [3209] | 22.396238 | 3.500000 | 10.000000 | Fused Silica |
| 22 | [3209] | 81.185257 | 11.50000 | 10.000000 | Air |
| 23 | [3207] | — | 48.014929 | 0.122526 | Air |
| 24 | [3205] | — | 15.264241 | 62.000000 | Fused Silica |
| 25 | [3205] | — | −5.264241 | 62.000000 | Reflect. |
| 26 | [3205] | — | −48.014929 | 62.000000 | Air |
| 27 | [3206] | 77.029248 | 48.014929 | 66.000000 | Reflect. |
| 28 | [3205] | — | 15.264241 | 62.000000 | Fused Silica |
| 29 | [3205] | — | 0.5000000 | 62.000000 | Air |
| 30 | [3204] | — | 0.501766 | | |

Figure 33:
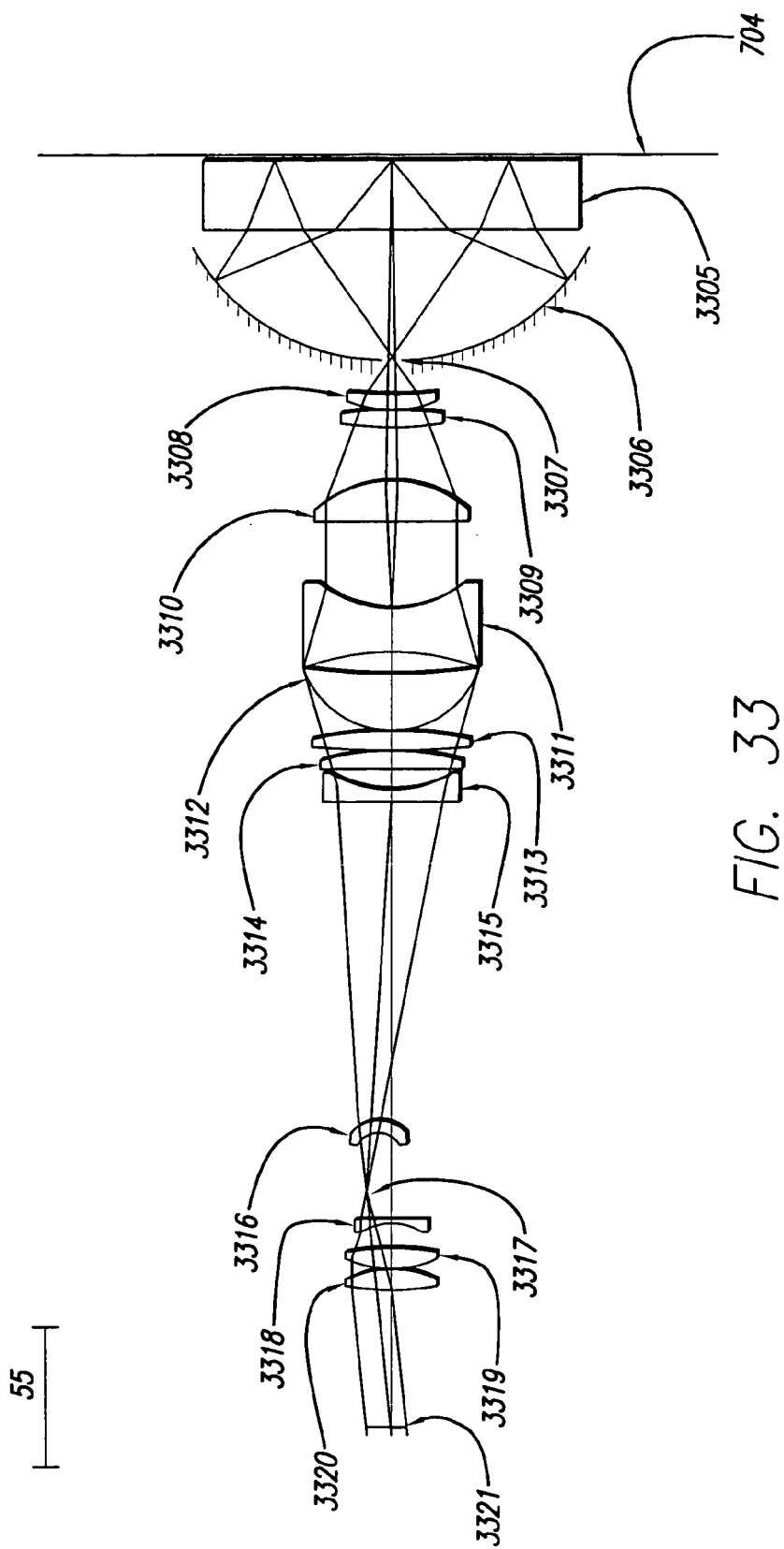
FIG. 33 presents an additional catadioptric system with a relayed pupil plane.

Still a further aspect of the current design also provides an external pupil plane conjugate to the internal pupil of the objective as shown in FIG. 33. This is an all fused silica design with a 0.98 NA, 2.0 mm field size, a 7.653 mm focal length, and 0.75 millimeter working distance. This design is for use at a wavelength of 0.266 micrometers where the index of fused silica is 1.499776.

The system of FIG. 33 has the following dimensions:

| Aperture (mm) | Surface Radius (mm) | Thickness (mm) | Radius | [element] Material |
|---|---|---|---|---|
| 0 | | — | 1.0000e+20 | 1.3065e+19 | Air |
| 1 | | — | — | 7.50000 | Fused Silica |
| 2 | | — | 56.10343 | 7.50000 | Air |
| 3 | | 172.92817 | 6.50000 | 17.00000 | Fused Silica |
| 4 | | −51.15640 | 1.00000 | 17.00000 | Air |
| 5 | | 36.69504 | 7.00000 | 17.00000 | Fused Silica |
| 6 | | −101.81708 | 9.33307 | 17.00000 | Air |
| 7 | | −40.11542 | 3.00000 | 13.00000 | Fused Silica |
| 8 | | −131.54232 | 32.30953 | 13.00000 | Air |
| 9 | | −10.54200 | 5.29845 | 8.00000 | Fused Silica |
| 10 | | −13.00226 | 126.38070 | 10.00000 | Air |
| 11 | | −1615.27308 | 4.50000 | 29.00000 | Fused Silica |
| 12 | | 60.17164 | 7.97588 | 27.00000 | Air |
| 13 | | −2.6045e+04 | 7.50000 | 30.00000 | Fused Silica |
| 14 | | −107.86582 | 0.10000 | 30.00000 | Air |
| 15 | | 407.32327 | 8.00000 | 33.00000 | Fused Silica |

-continued

| Aperture (mm) | Surface Radius (mm) | Thickness (mm) | Radius | [element] Material |
|---|---|---|---|---|
| 16 | −158.71706 | 0.1000 | 33.00000 | Air |
| 17 | 41.13105 | 22.90344 | 36.50000 | Fused Silica |
| 18 | 476.74020 | 8.02351 | 36.00000 | Air |
| 19 | −108.54992 | 17.81428 | 36.00000 | Fused Silica |
| 20 | 52.28708 | 32.71346 | 30.00000 | Air |
| 21 | 744.72666 | 17.00000 | 31.00000 | Fused Silica |
| 22 | −47.71508 | 21.21160 | 31.00000 | Air |
| 23 | 112.01284 | 7.00000 | 21.00000 | Fused Silica |
| 24 | −132.26649 | 0.10000 | 21.00000 | Air |
| 25 | 46.50995 | 6.00000 | 18.00000 | Fused Silica |
| 26 | 213.25215 | 13.00000 | 18.00000 | Air |
| 27 | — | 51.58643 | 0.13054 | Air |
| 28 | — | 26.79611 | 73.00000 | Fused Silica |
| 29 | — | −26.79611 | 73.00000 | Reflect. |
| 30 | — | −51.58643 | 73.00000 | Air |
| 31 | 88.23207 | 51.58643 | 77.00000 | Reflect. |
| 32 | — | 26.79611 | 73.00000 | Fused Silica |
| 33 | — | 0.75000 | 73.00000 | Air |
| 34 | — | — | 1.00123 | image |

Figure 34:
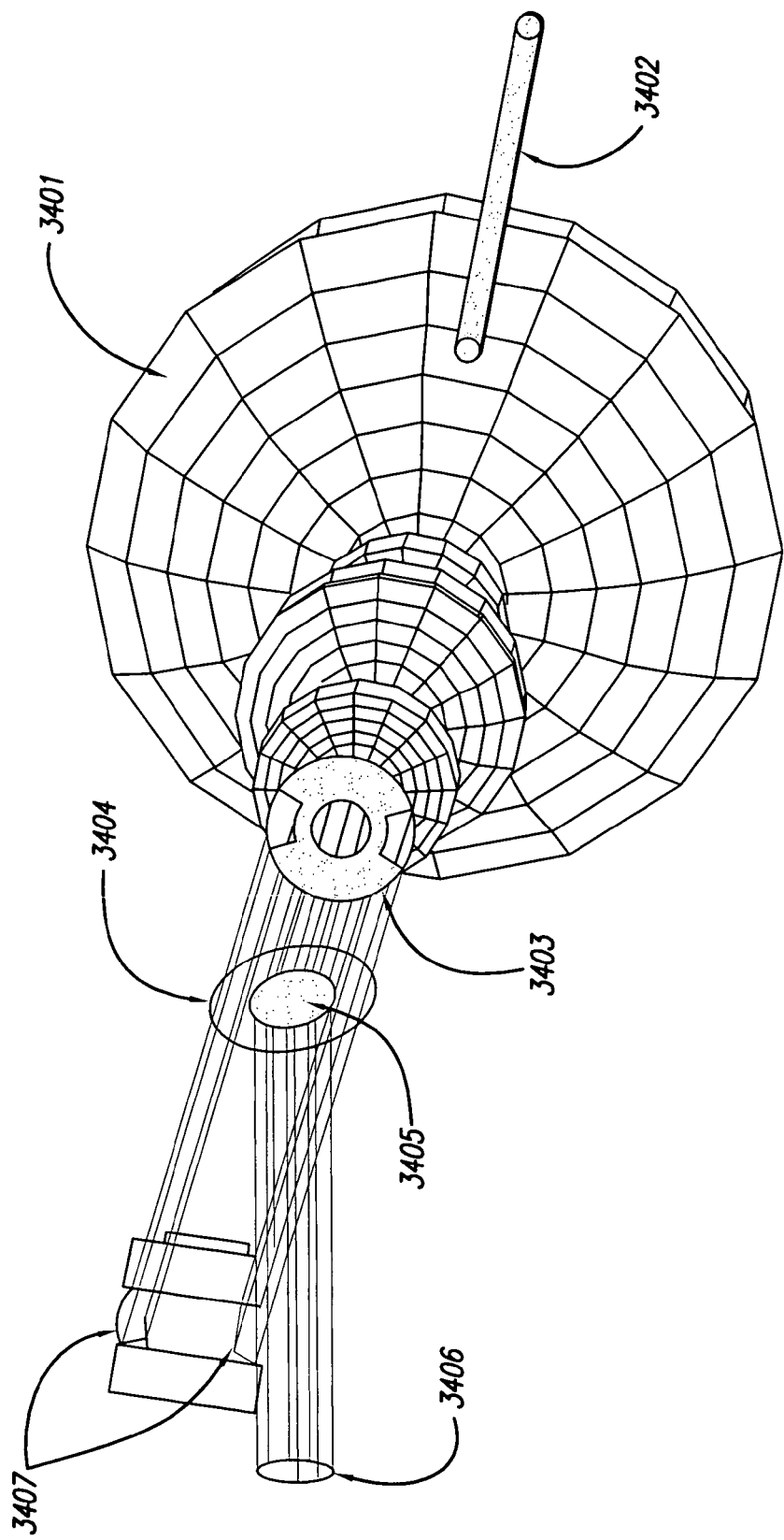
FIG. 34 illustrates the simultaneous operation of double dark field and directional dark field modes in the system disclosed herein.

Transferring the pupil to an external plane can affords simultaneous operation of various dark field schemes. For example, double dark field and directional dark field can be performed using the system illustrated in FIG. 34. The system illustrated in FIG. 34 is based on the catadioptric objective with a relayed pupil. From FIG. 34, the catadioptric system 3401 employs a laser for oblique illumination as shown by laser beam 3402. Scattered, diffracted, and reflected light collected from the object is filtered at the pupil plane by a filter 3403 similar to a composite of the filters illustrated in FIGS. 21 and 22. The light beam 3406 passing through the central opening in the pupil filter 3403 corresponds to the directional dark field scheme, while light passing through the outer openings of pupil filter 1903 corresponds to the double dark field scheme. Light energy for these two different dark field schemes may be separated using a plate 3404 having a reflective central spot 3406 and directed to separate detectors. Other simultaneous schemes are also possible, such as normal incidence dark field imaging using oblique and near normal collection.

Other methods of pupil shaping may be employed. For example, pupil shaping may create simultaneous operation with different dark field schemes. A diffractive optic, segmented optic, or other device can be placed at or near the pupil plane to direct different portions of the pupil to different locations. Multiple detectors or a single scanned detector can be used.

In a further aspect, a tube lens group can be used with the 0.97, 0.98, and 0.99 NA objectives in systems having a 1.0 mm field size. The tube lens group has the same 30 mm collimated beam diameter as used in those designs as shown in FIGS. 17, 29, 30 and 31 and is designed for the single wavelength of 0.266 micrometers. The tube lens group magnifies the 1.0 mm field size of the objectives onto a 36 mm detector. In accordance with other aspects disclosed herein, the tube lens group is designed to have a distant exterior pupil plane to match the buried interior pupil of the catadioptric objectives. A similar tube lens group can also be designed to work with objectives that have a larger field of view or a relayed pupil. The Strehl ratio of the tube lens group design is approximately 0.99 over the field. A more complicated tube lens group design is necessary for use with the larger field size objective due not only to larger field size but also to the lower magnification if the same size detector is used.

Figure 35:
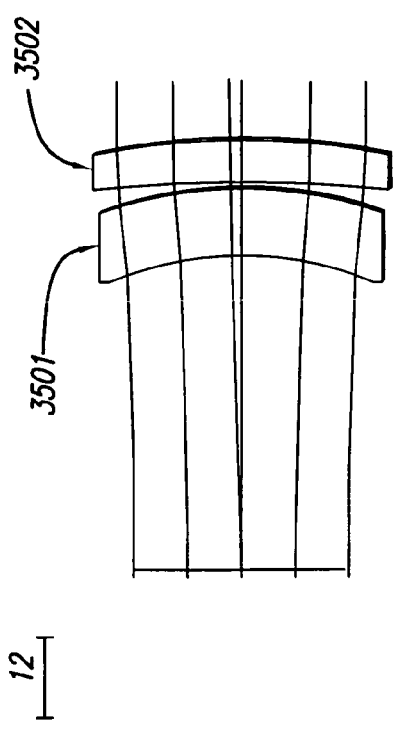
FIG. 35 shows an expanded view of the tube lens group.
Figure 36:
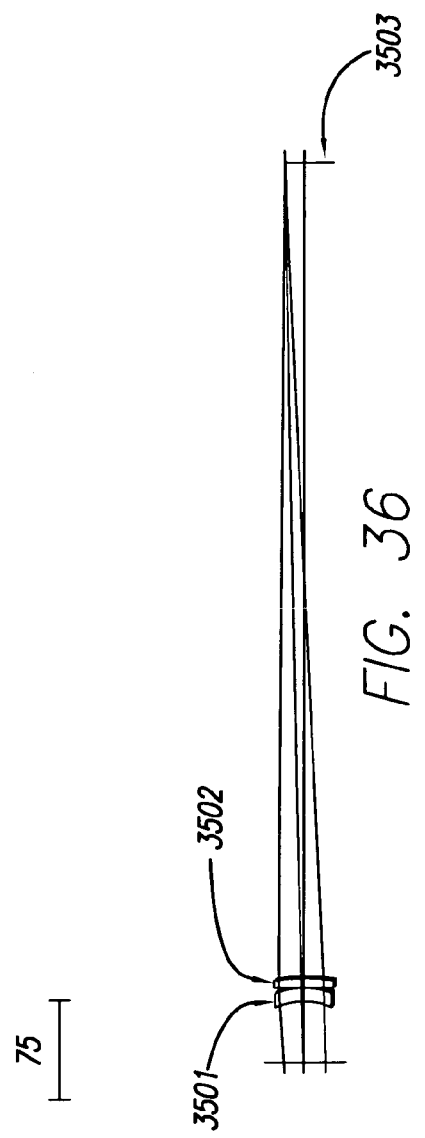
FIG. 36 presents a tube lens group for use with varying NA systems and providing mapping of a 1.0 millimeter field size image onto a 36 millimeter detector.

The tube lens group is illustrated in FIGS. 35 and 36 and includes lenses 3501 and 3502 as well as focal plane 3503. A tube lens group having focal length of 555.6 mm and an NA of 0.027 will have the following dimensions for 0.97, 0.98, and 0.99 NA objectives for a wavelength of 0.266 micrometers and a 30 mm beam diameter:

| Aperture (mm) | Surface Radius (mm) | Thickness (mm) | Radius | [element] Material |
|---|---|---|---|---|
| 0 | — | 1.0000e+20 | 3.2400e+18 | Air |
| 1 (Aperture Stop) | — | 46.090490 | 15.000000 | Air |
| 2 [3501] | −49.980600 | 10.00000 | 19.000000 | Fused silica |
| 3 [3501] | −56.665981 | 1.000000 | 20.000000 | Air |
| 4 [3502] | −217.218335 | 6.000000 | 21.000000 | Fused Silica |
| 5 [3502] | −111.297311 | 599.512125 | 21.000000 | Air |
| 6 | — | — | 18.000054 | Air |

The resultant image is thus 36 millimeters in length.

Figure 37:
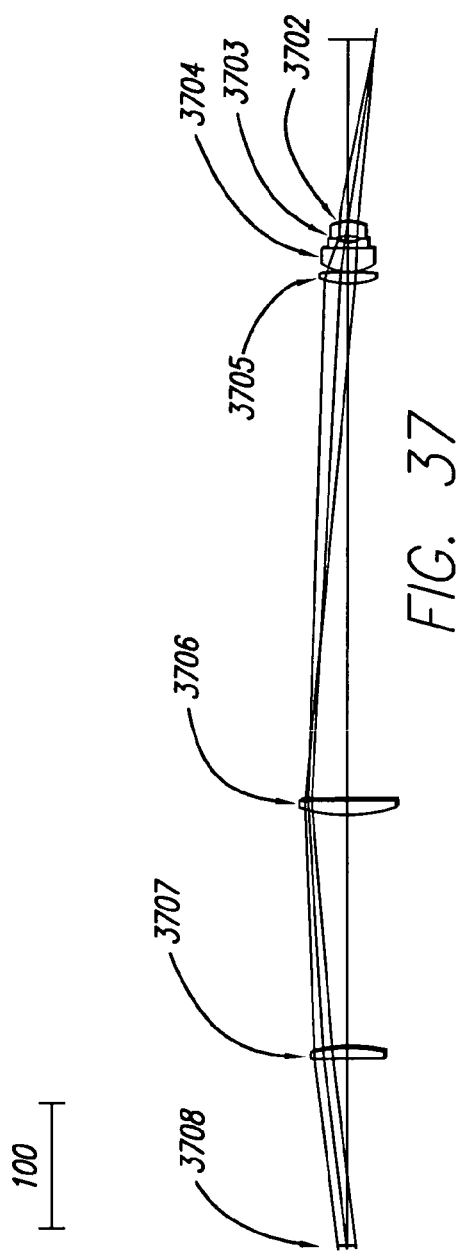
FIG. 37 is a six element varifocal tube lens group for providing magnifications from 20× to 200×.
Figure 38:
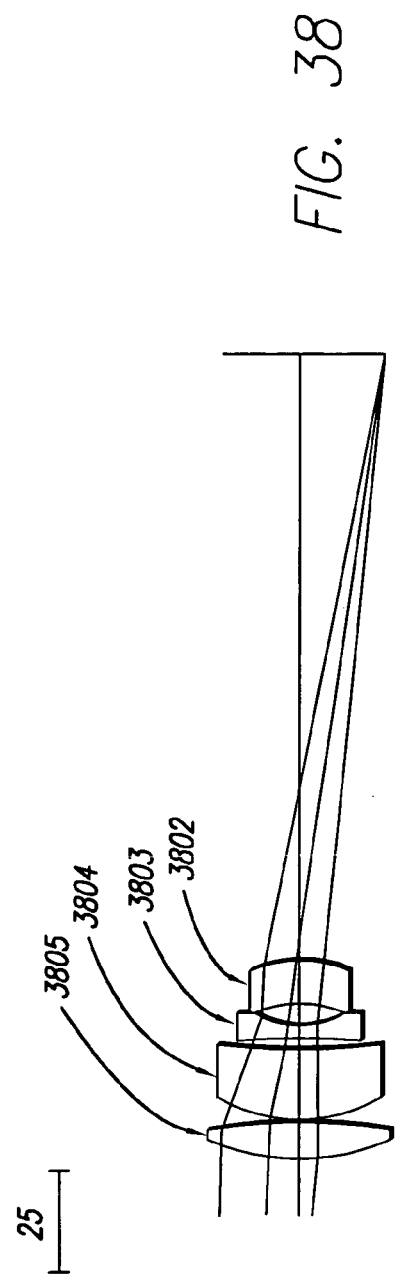
FIG. 38 illustrates the four elements of the varifocal tube lens group furthest from the pupil plane.

Still another aspect of the current system uses a six element varifocal tube lens group for 20× to 200× as shown in FIG. 37 and which can be independently corrected from the main system and which provides magnification and transposition from the pupil plane. At the edge of the 38 millimeter detector, for a 20× magnification, the Strehl ratio for a 0.266 micrometer wavelength is 0.955. This value improves over the rest of the detector and at magnifications greater than 20×. Worst case distortion from 20× to 200× is 0.06 percent. The nearest distance from a lens to the detector is 149 millimeters, and this distance increases by 777 millimeters in extending the magnification from 20× to 200×. The motion of the moving group of four lenses, as shown in FIG. 37, is 160 mm. Note that both FIGS. 37 and 38 illustrate the varifocal tube lens group at 20× magnification.

This varifocal tube lens group design may be used with an objective having a 15 mm diameter pupil, such as with the relayed pupil design described above. It may also be desirable to use this type of a varifocal tube lens group with an objective that does not have a relayed pupil. This is possible using the concepts disclosed herein, with adjustments that would be apparent to those of ordinary skill in the art.

This design is for use at 0.266 micrometers where the refractive index of fused silica is 1.49968. For the 20× magnification the system has focal length of 153 mm and an NA of 0.049. The dimensions are as follows:

| Aperture (mm) | Surface Radius (mm) | Thickness (mm) | Radius | [element] Material |
|---|---|---|---|---|
| 0 | — | 1.0000e+20 | 1.2456e+19 | Air |
| 1 [3708] | — | — | 7.5000000 | Fourier Plane |
| 2 [3708] | — | 152.90980 | 7.5000000 | Air |
| 3 [3707] | −1002.31432 | 7.000000 | 30.000000 | Fused Silica |
| 4 [3707] | −140.48005 | 192.59159 | 30.000000 | Air |
| 5 [3706] | 127.96246 | 10.000000 | 38.000000 | Fused |

-continued

| Aperture (mm) | Surface Radius (mm) | Thickness (mm) | Radius | [element] Material |
|---|---|---|---|---|
| 6 [3706] | 1694.87685 | 423.59936 | 38.000000 | Silica Air |
| 7 [3705] | 58.02517 | 8.0000000 | 21.000000 | Fused Silica |
| 8 [3705] | −126.99340 | 1.00992 | 21.000000 | Air |
| 9 [3704] | 34.98956 | 17.94389 | 19.000000 | Fused Silica |
| 10 [3704] | 136.51285 | 2.28230 | 14.500000 | Air |
| 11 [3703] | −132.38435 | 3.12463 | 14.000000 | Fused Silica |
| 12 [3703] | 20.90456 | 5.07104 | 10.500000 | Air |
| 13 [3702] | −25.78032 | 10.53393 | 10.500000 | Fused Silica |
| 14 [3702] | −27.58716 | 148.87138 | 11.500000 | Air |
| 15 | — | — | 19.05723 | |

Figure 39:
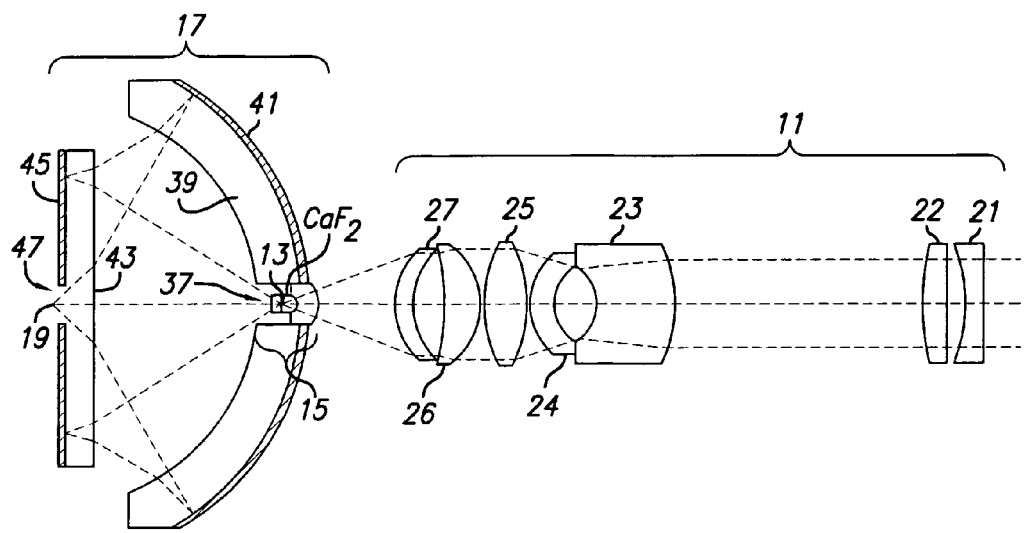
FIG. 39 is a schematic side view of a catadioptric imaging system in accord with the parent application.

FIG. 39 shows an alternate catadioptric imaging system suited for use in broadband deep ultraviolet applications and made up of a focusing lens group 11 for forming an intermediate image 13, a field lens group 15 disposed proximate to the intermediate image 13 for correcting chromatic aberrations, and a catadioptric group 17 for focusing light from the intermediate image 13 to a final image 19. The imaging system has the ability to correct both monochromatic (Seidel) aberrations and chromatic aberrations (longitudinal and lateral), as well as chromatic variations of the monochromatic aberrations, over a wavelength band that extends into the deep ultraviolet (UV) portion of the spectrum, covering 0.20 to 0.40 micron UV light. The catadioptric system can be adapted for a number of UV imaging applications, including as a UV microscope objective, a collector of surface scattered UV light in a wafer inspection apparatus, or as mask projection optics for a UV photolithography system.

The focusing lens group 11 in FIG. 39 includes seven lens elements 21–27, with two of the lens elements (21 and 22) separated by a substantial distance from the remaining five lens elements (23–27). The separations of the pair of lens elements 21 and 22 from the remaining five lens elements 23–27 is typically on the order of at least one-half the total combined thickness of the five lens elements 23–27. For example, lens elements 23–27 may span a distance of about 60 millimeters (mm) and lens element 22 may be 30 to 60 mm from lens element 23. The actual dimensions depend on the scale chosen. The two lenses 21 and 22 form a low power doublet for correcting chromatic variation of monochromatic image aberrations, such as coma and astigmatism. By having this doublet 21 and 22 relatively far from the other system components, the shift of the light beam with field angles on these two lenses is maximized. That in turn helps greatly in achieving the best correction of chromatic variation of aberrations.

The five lenses 23–27 of the main focusing subgroup consist of a thick strong negative meniscus lens 23, an opposite-facing relatively strongly-curved negative meniscus lens 24, a strong bi-convex lens 25, a strong positive meniscus lens 26, and an opposite-facing strongly-curved, but relatively very weak, meniscus lens 27 of either positive or negative power. Variations of this lens 23–27 subgroup are possible. The subgroup focuses the light to an intermediate image 13. The curvature and positions of the lens surfaces are selected to minimize monochromatic aberrations and to cooperate with the doublet 21–22 to minimize chromatic variations of those aberrations.

The field lens group 15 typically comprises an achromatic triplet, although any achromatized lens group can be used. Both fused silica and $CaF_2$ glass materials are used. Other possible deep UV transparent refractive materials can include $MgF_2$, $SrF_2$, $LaF_3$ and $LiF$ glasses, or mixtures thereof. In addition to refractive materials, diffractive surfaces can be used to correct chromatic aberrations. Because the dispersions between the two UV transmitting materials, $CaF_2$ glass and fused silica, are not very different in the deep ultraviolet, the individual components of the group 15 have strong curvatures. Primary color aberrations are corrected mainly by the lens elements in the catadioptric group 17 in combination with the focusing lens group 11. Achromatization of the field lens group 15 allows residual lateral color to be completely corrected.

The catadioptric group 17 of FIG. 39 includes a fused silica meniscus lens 39 with a back surface having coating 41, and fused silica lens 43 with a back surface having a reflective coating 45. The two lens elements 39 and 43 front surfaces face each other. The reflective surface coating 41 and 45 are typically aluminum, possibly with a dielectric overcoat to enhance reflectivity.

The first lens 39 has a hole 37 centrally formed therein along the optical axis of the system. The reflective coating 41 likewise ends at the central hole 37 leaving a central optical aperture through which light can pass unobstructed by either the lens 39 or its reflective coating 41. The optical aperture defined by the hole 37 is in the vicinity of the intermediate image plane 13 so that minimum optical loss occurs. The achromatic field lens group 15 is positioned in or near the hole 37. The second lens 43 does not normally have a hole, but there is a centrally located opening or window 47 where the coating is absent on the surface reflective coating 45. The optical aperture in lens 39 with its reflective coating 41 need not be defined by a hole 37 in the lens 39, but could be defined simply by a window in the coating 41 as in coating 45. In that case, light would pass one additional time through the refractive surfaces of lens 39.

Light from the source transmitted along the optical axis toward the intermediate image plane 13 passes through the optical aperture 37 in the first lens 39 and then through the body of the second lens 43 where it is reflected by the near planar (or planar) mirror coating 45 back through the body of the second lens 43. The light then passes through the first lens 39, is reflected by the mirror surface 41 and passes back through the first lens 39. Finally the light, now strongly convergent passes through the body of the second lens 43 for a third time, through the optical aperture 47 to the target image plane adjacent aperture 47. The curvatures and positions of the first and second lens surfaces are selected to correct primary axial and lateral color in conduction with the focal lens group 11.

Figure 40:
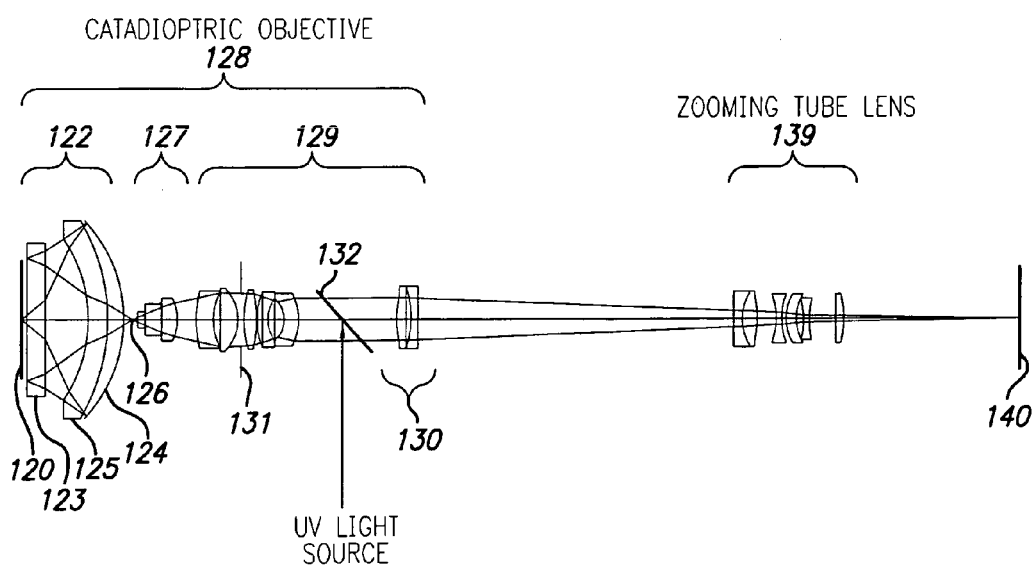
FIG. 40 is a schematic side view of a catadioptric imaging system.

For a flexible deep UV microscope system, it is important to provide various magnifications, numerical apertures, field sizes, and colors. In principle, an UV microscope system can comprise several catadioptric objectives, tube lenses, and zoom lenses. An ultra-broadband UV microscope imaging system as illustrated in FIG. 40 comprises a catadioptric objective section 128 and a zooming tube lens group sections 139. The catadioptric objective section 128 comprises a catadioptric lens group 122, a field lens group 127, and a focusing lens group 129. The beam splitter 132 provides an entrance for the UV light source. The aperture stop 131 is used to adjust the system imaging numerical aperture (NA). The microscope system images an object 120 (e.g., a wafer being inspected) to the image plane 140.

The catadioptric objective section 128 performs ultra-broadband imaging in the UV spectral region (about 0.20 to 0.40 micron wavelength). It has excellent performance for high numerical apertures and large object fields. This system uses the Schupmann principle in combination with an Offner field lens to correct for axial color and first order lateral color, and an achromatized field lens group to correct the higher order lateral color. The elimination of the residual higher order chromatic aberrations makes the ultra-broadband UV objective design possible.

The catadioptric lens group 122 includes a near planar or planar reflector 123, which is a reflectively coated lens element, a meniscus lens 125, and a concave spherical reflector. Compared to the reflectively coated lens element 39 in FIG. 39, this aspect uses a concave reflector 124 and a large meniscus lens 125 to simplify manufacturing. Both reflective elements have central optical apertures without reflective material to allow light from the intermediate image plane 126 to pass through the concave reflector, be reflected by the near planar (or planar) reflector 123 onto the concave reflector 124, and pass back through the near planar or planar reflector 123, traversing the associated lens element or elements on the way.

The achromatic multi-element field lens group 127 is made from two or more different refractive materials, such as fused silica and fluoride glass, or diffractive surfaces. The field lens group 127 may be optically coupled together or alternatively may be spaced slightly apart in air. Because fused silica and fluoride glass do not differ substantially in dispersion in the deep ultraviolet range, the individual powers of the several component element of the field lens group need to be of high magnitude. Use of such an achromatic field lens allows the complete correction of axial color and lateral color over an ultra-broad spectral range. In one aspect of the design, only one field lens component need be of a refractive material different than the other lenses of the system. Compared to group 15 in FIG. 39, the field lens group 127 is moved slightly from the intermediate image location to reduce the heat load and surface scattering of the field lens group.

The system may have a focusing lens group 129 with multiple lens elements, preferably all formed from a single type of material, with refractive surfaces having curvatures and positions selected to correct both monochromatic aberrations and chromatic variation of aberrations and focus light to an intermediate image. In the focusing lens group 129 a combination of lenses 130 with low power corrects the system for chromatic variation in spherical aberration, coma, and astigmatism.

The zooming tube lens 139 combined with the catadioptric objective 128 provides many desirable features. Such an all-refractive zooming lens ideally will allow the detector array 140 to be stationary during zooming, although the invention is not limited to this aspect. Assuming that the catadioptric objective system 128 does not also have any zooming function, there are two design possibilities open to the zooming tube lens system 139.

First, the zooming section 139 can be formed of the same refractive material, such as fused silica, and it must be designed so that primary longitudinal and primary lateral color do not change during zooming. These primary chromatic aberrations do not have to be corrected to zero, and cannot be if only one glass type is used, but they have to be stationary, which is possible. Then the design of the catadioptric objective 128 must be modified to compensate for these uncorrected but stationary chromatic aberrations of the zooming tube lens. Despite the limited image quality, this design possibility is very desirable since the whole combined microscope system may in certain circumstances be formed of a single material, i.e., fused silica, except for the calcium fluoride or a diffractive surface in the achromatized Offner-type field lens.

Second, the zooming tube lens group 139 can be corrected for aberrations independently of the catadioptric objective 128. This requires the use of at least two refractive materials with different dispersions, such as fused silica and calcium fluoride, or diffractive surfaces. The result may be a tube lens system that, because of unavoidable higher-order residuals of longitudinal and lateral color over the entire zoom range, is not capable of high performance over a very broad UV spectral region. Compromises must then be made in the form of reducing the spectral range, the numerical aperture, the field size of the combined system, or some combination of these compromises. The result is that the very high capabilities of the catadioptric objective cannot be duplicated with an independently corrected zooming tube lens.

The present system straddles the two situations just described. The zooming tube lens 139 is first corrected independently of the catadioptric objective 128, using two refractive materials (such as fused silica and calcium fluoride). Lens 139 is then combined with the catadioptric objective 128 and then the catadioptric objective is modified to compensate for the residual higher-order chromatic aberrations of the zooming tube lens system. This is possible because of the design features of the field lens group 127 and the low power lens group 130 of the catadioptric objective described earlier. The combined system is then optimized with all parameters being varied to achieve the best performance.

One unique feature of the present system is the particular details of the zooming tube lens. If the higher-order residual chromatic aberrations of this zooming system change during zoom, then the catadioptric objective cannot exactly compensate for them except at one zoom position. It is relatively easy for one skilled in the art to design a zooming tube lens system where the low-order chromatic aberrations do not change during zoom, and are corrected to zero as well. It can be very difficult to find a zooming tube lens design where the higher-order chromatic aberration residuals (which are uncorrectable to zero, in that system by itself) do not change during the zooming.

A tube lens section can be designed such that its higher-order chromatic aberrations do not change by any significant amount during zoom. If the detector array 140 is allowed to move during zoom, then the design problem becomes much easier, but that is not nearly as desirable as having an image position fixed relative to the rest of the system.

The imaging system of the system provides a zoom from 36× to 100× and greater, and integrates objectives, turret, tube lenses (to provide more magnifications) and zoom optics into one module. The imaging system reduces optical and mechanical components, improves manufacturability and reduces production costs. The imaging system has several performance advantages such as: high optical resolution due to deep UV imaging, reduced thin film interference effects due to ultra-broadband light, and increased light brightness due to integration of ultra-broad spectral range. The wide range zoom provides continuous magnification change. The fine zoom reduces aliasing and allows electronic image processing, such as cell-to-cell subtraction for a repeating image array. By placing an adjustable aperture in the aperture stop of the microscope system one can adjust the NA and obtain the desired optical resolution and depth of focus. The system is flexible with an adjustable wavelength, an adjustable bandwidth, an adjustable magnification, and an adjustable numerical aperture.

Three possible aspects of zoom lenses are provided. The first aspect provides linear zoom motion with a fixed detector array position. The second aspect provides linear zoom motion with a moving detector array position. The third aspect, in addition to zoom lenses, utilizes folding mirrors to reduce the physical length of the imaging system and fix the detector array position.

Figure 41:
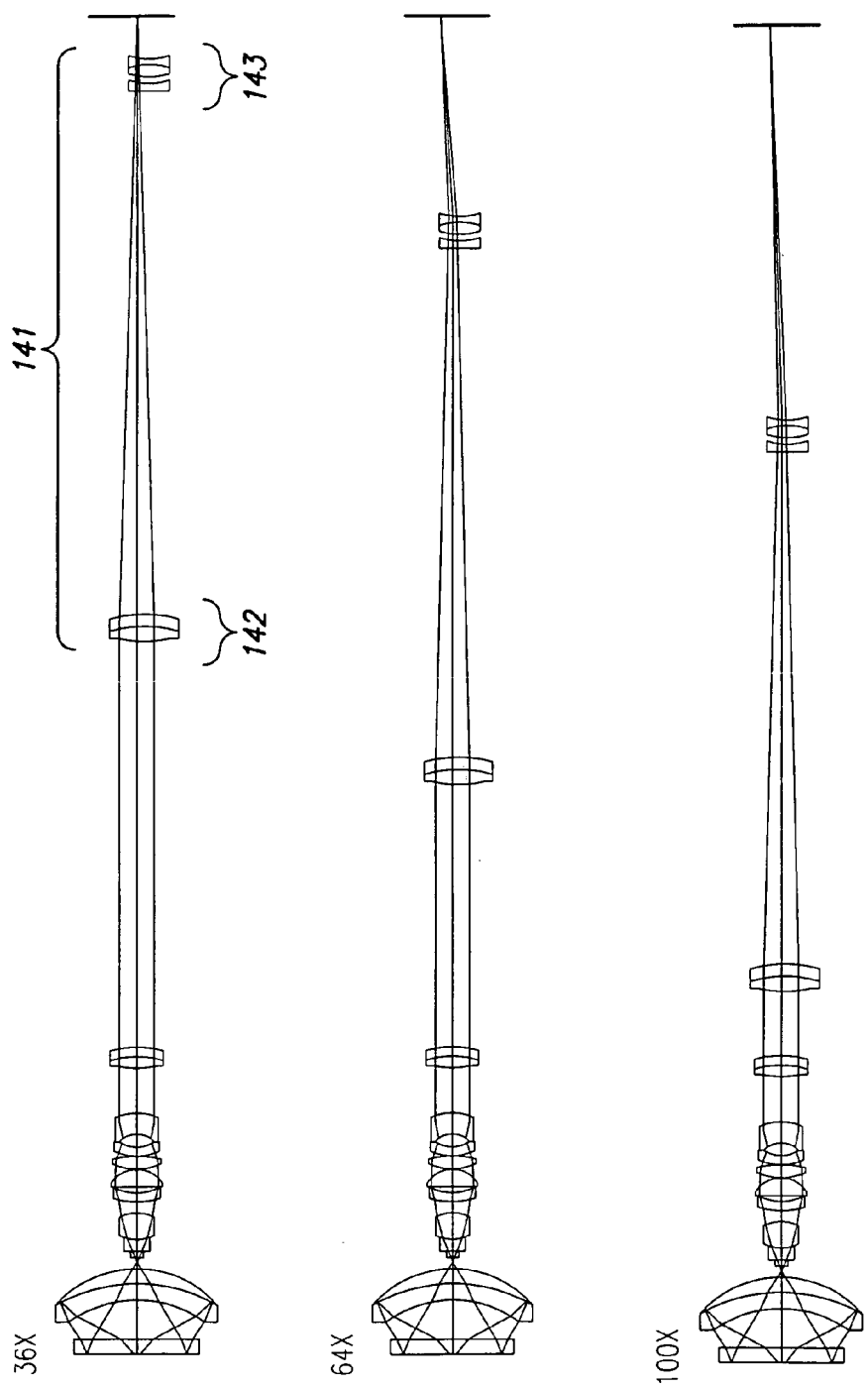
FIG. 41 is schematic side view of a catadioptric imaging system in the three positions having 36×, 64× and 100× power magnifications.

The first zoom lenses provide linear zoom motion with a fixed detector array position. FIG. 41 shows the 36× zoom arrangement of the lenses, the 64× zoom arrangement of the lenses and the 100× zoom arrangement of the lenses. The detector array 140 (not shown) is fixed. The zooming tube lens design 141 is comprised of two moving lens groups 142 and 143. The beam splitter is not shown in this and later figures for the purpose of clarity. The following table lists the surfaces shown in FIG. 41, where the surface numbering begins at "0" for the final image counting towards the object being inspected.

Lens Data for the First Aspect 0.90 N.A., fixed detector, 36×–100× zoom, 1.0 mm field size

| Surface | Radius | Thickness | | Material |
|---|---|---|---|---|
| 0 | — | 30.000000 | 36× | Air |
|  |  | 152.396279 | 64× |  |
|  |  | 318.839746 | 100× |  |
| 1 | −46.843442 | 4.000000 |  | Calcium fluoride |
| 2 | 67.017379 | 0.999804 |  | Air |
| 3 | 122.003494 | 7.000000 |  | Silica |
| 4 | −34.944144 | 4.496612 |  | Air |
| 5 | −42.883889 | 4.000000 |  | Calcium fluoride |
| 6 | −1.5857e+03 | 339.659737 | 36× | Air |
|  |  | 298.114540 | 64× |  |
|  |  | 279.997392 | 100× |  |
| 7 | −657.423731 | 9.000000 |  | Calcium fluoride |
| 8 | −67.124645 | 0.999689 |  | Air |
| 9 | −70.484550 | 6.000000 |  | Silica |
| 10 | 102.732012 | 28.382549 |  | Air |
| 11 | 170.942101 | 13.000000 |  | Calcium fluoride |
| 12 | −126.768482 | 274.177371 | 36× | Air |
|  |  | 193.326289 | 64× |  |
|  |  | 44.999970 | 100× |  |
| 13 | 103.846671 | 5.000000 |  | Silica |
| 14 | 57.151413 | 3.500000 |  | Air |
| 15 | 113.406488 | 7.000000 |  | Silica |
| 16 | −149.254887 | 58.301706 |  | Air |
| 17 | 41.730749 | 14.904897 |  | Silica |
| 18 | 17.375347 | 11.364798 |  | Air |
| 19 | −22.828011 | 5.892666 |  | Silica |
| 20 | −57.773872 | 1.000000 |  | Air |
| 21 | 174.740180 | 7.000000 |  | Silica |
| 22 | −48.056749 | 4.000000 |  | Air |
| 23 | 24.023380 | 11.500000 |  | Silica |
| 24 | −1.0394e+03 | 4.198255 |  | Air |
| 25 | −43.531092 | 5.000000 |  | Silica |
| 26 | −197.030499 | 1.000000 |  | Air |
| 27 | 45.618003 | 29.827305 |  | Silica |
| 28 | −81.744432 | 1.662262 |  | Air |
| 29 | 17.258988 | 4.000000 |  | Calcium fluoride |
| 30 | −31.010978 | 0.315372 |  | Air |
| 31 | −24.055515 | 2.000000 |  | Silica |
| 32 | 5.602559 | 0.020000 |  | Air |
| 33 | 5.602559 | 8.318486 |  | Calcium fluoride |

-continued

| Surface | Radius | Thickness | Material |
|---|---|---|---|
| 34 | −24.871116 | 7.710304 | Air |
| 35 | — | 8.328925 | Air |
| Aperture Stop |  |  |  |
| 36 | 85.000000 | 11.000000 | Silica |
| 37 | 70.542512 | 29.938531 | Air |
| 38 | 1.6514e+03 | 10.000000 | Silica |
| 39 | Infinity | −10.000000 | Reflect |
| 40 | 1.6514e+03 | −29.938531 | Air |
| 41 | 70.542512 | −11.000000 | Silica |
| 42 | 85.000000 | −8.328925 | Air |
| 43 | 74.648515 | 8.328925 | Reflect |
| 44 | 85.000000 | 11.000000 | Silica |
| 45 | 70.542512 | 29.938531 | Air |
| 46 | 1.6514e+03 | 10.000000 | Silica |
| 47 | Infinity | 1.500000 | Air |

Figure 42:
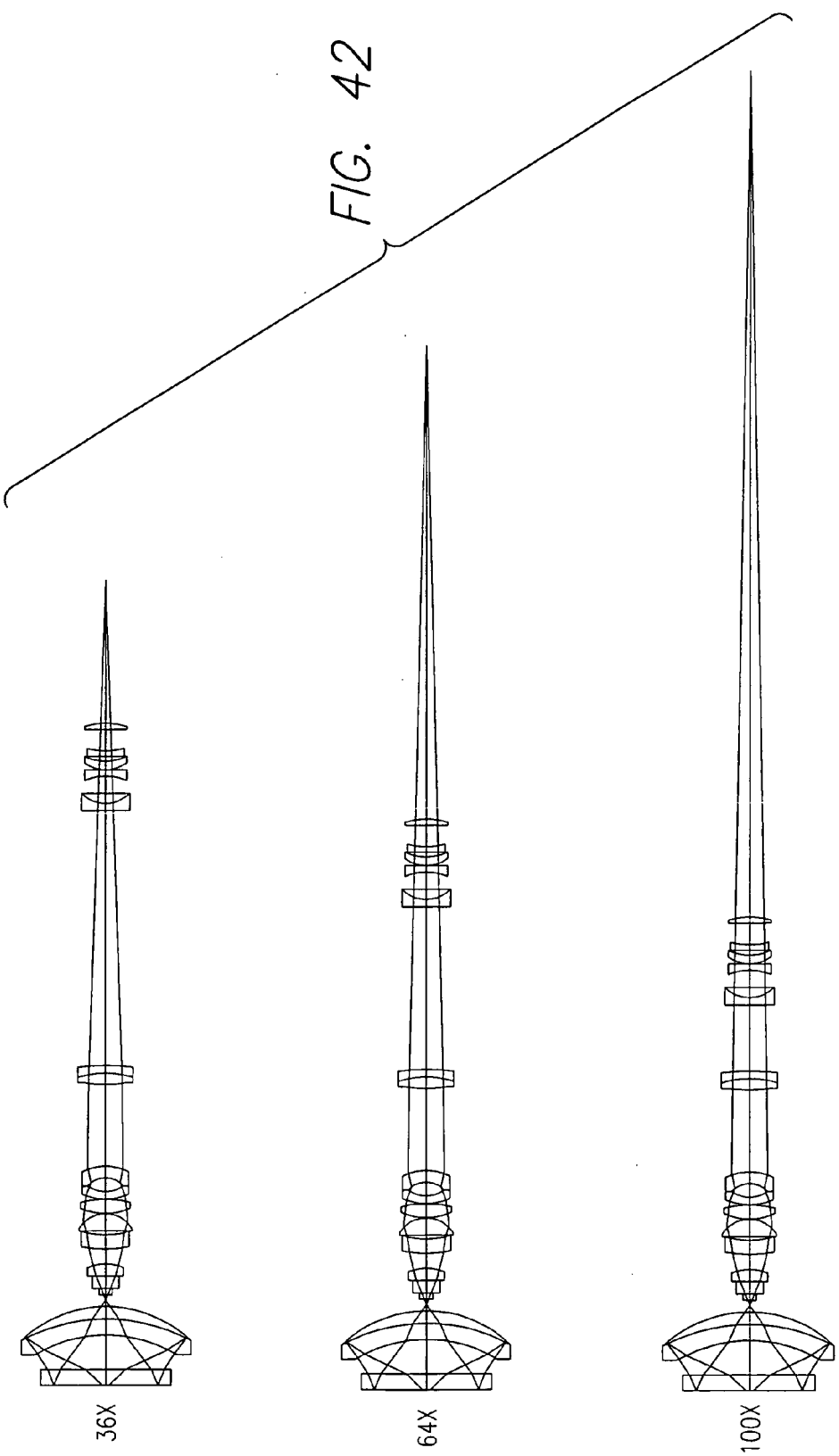
FIG. 42 is a schematic side view of a catadioptric imaging system in three positions having 36×, 64× and 100× power magnifications.

The second aspect of zoom lenses provides linear zoom motion with a moving detector array position and FIG. 42 shows the 36× zoom arrangement of the lenses, the 64× zoom arrangement of the lenses and the 100× zoom arrangement of the lenses. The following table lists the surfaces shown in FIG. 42, where the surface numbering begins at "0" for the final image incrementing by 1 towards the object being inspected.

Lens Data for the Second Aspect 0.90 N.A., moving detector, 36× to 100× zoom, 1.0 mm field size

| Surface | Radius | Thickness | | Material |
|---|---|---|---|---|
| 0 | Infinity | 110.004950 | 36× | Air |
|  |  | 405.371660 | 64× |  |
|  |  | 785.131189 | 100× |  |
| 1 | 73.156621 | 5.000000 |  | Calcium fluoride |
| 2 | −609.638437 | 18.230155 |  | Air |
| 3 | −30.303090 | 3.500000 |  | Calcium fluoride |
| 4 | 44.361656 | 4.000000 |  | Air |
| 5 | −51.318999 | 7.765282 |  | Silica |
| 6 | −23.231195 | 1.564401 |  | Air |
| 7 | −119.756315 | 4.000000 |  | Calcium fluoride |
| 8 | 40.002701 | 12.019418 |  | Air |
| 9 | 54.594789 | 10.000000 |  | Calcium flouride |
| 10 | −28.923744 | 0.100000 |  | Air |
| 11 | −29.957411 | 5.000000 |  | Silica |
| 12 | −156.281481 | 202.434836 | 36 × | Air |
|  |  | 108.230318 | 64× |  |
|  |  | 64.650627 | 100× |  |
| 13 | 188.664770 | 4.500000 |  | Silica |
| 14 | 56.034008 | 3.500000 |  | Air |
| 15 | 214.395300 | 6.000000 |  | Silica |
| 16 | −79.842174 | 62.685096 |  | Air |
| 17 | 29.721624 | 10.000000 |  | Silica |
| 18 | 18.529920 | 11.406390 |  | Air |
| 19 | −23.406055 | 5.864347 |  | Silica |
| 20 | −46.076628 | 1.000000 |  | Air |
| 21 | 94.310969 | 7.000000 |  | Silica |
| 22 | −75.041727 | 4.000000 |  | Air |
| 23 | 23.509091 | 11.500000 |  | Silica |
| Aperture Stop |  |  |  |  |
| 24 | −399.710365 | 4.516455 |  | Air |
| 25 | −42.987793 | 10.000000 |  | Silica |
| 26 | −217.407455 | 12.083912 |  | Air |
| 27 | 24.940148 | 10.000000 |  | Calcium flouride |
| 28 | −177.604306 | 0.100000 |  | Air |
| 29 | 24.508018 | 10.000000 |  | Calcium flouride |

-continued

| Surface | Radius | Thickness | Material |
|---|---|---|---|
| 30 | −54.909641 | 0.664880 | Air |
| 31 | −16.389836 | 2.000000 | Silica |
| 32 | 4.296836 | 0.020000 | Air |
| 33 | 4.296836 | 3.000000 | Calcium fluoride |
| 34 | −14.014264 | 7.000000 | Air |
| 35 Internal image | — | 11.160093 | — |
| 36 | 102.631452 | 11.000000 | Silica |
| 37 | 84.741293 | 27.845569 | Air |
| 38 | 1.1470e+03 | 10.000000 | Silica |
| 39 | Infinity | −10.000000 | Reflect |
| 40 | 1.1470e+03 | −27.845569 | Air |
| 41 | 84.741293 | −11.000000 | Silica |
| 42 | 102.631452 | −11.160093 | Air |
| 43 | 75.033466 | 11.160093 | Reflect |
| 44 | 102.631452 | 11.000000 | Silica |
| 45 | 84.741293 | 27.845569 | Air |
| 46 | 1.1470e+03 | 10.000000 | Silica |
| 47 | Infinity | 1.500000 | Air |

Figure 43:
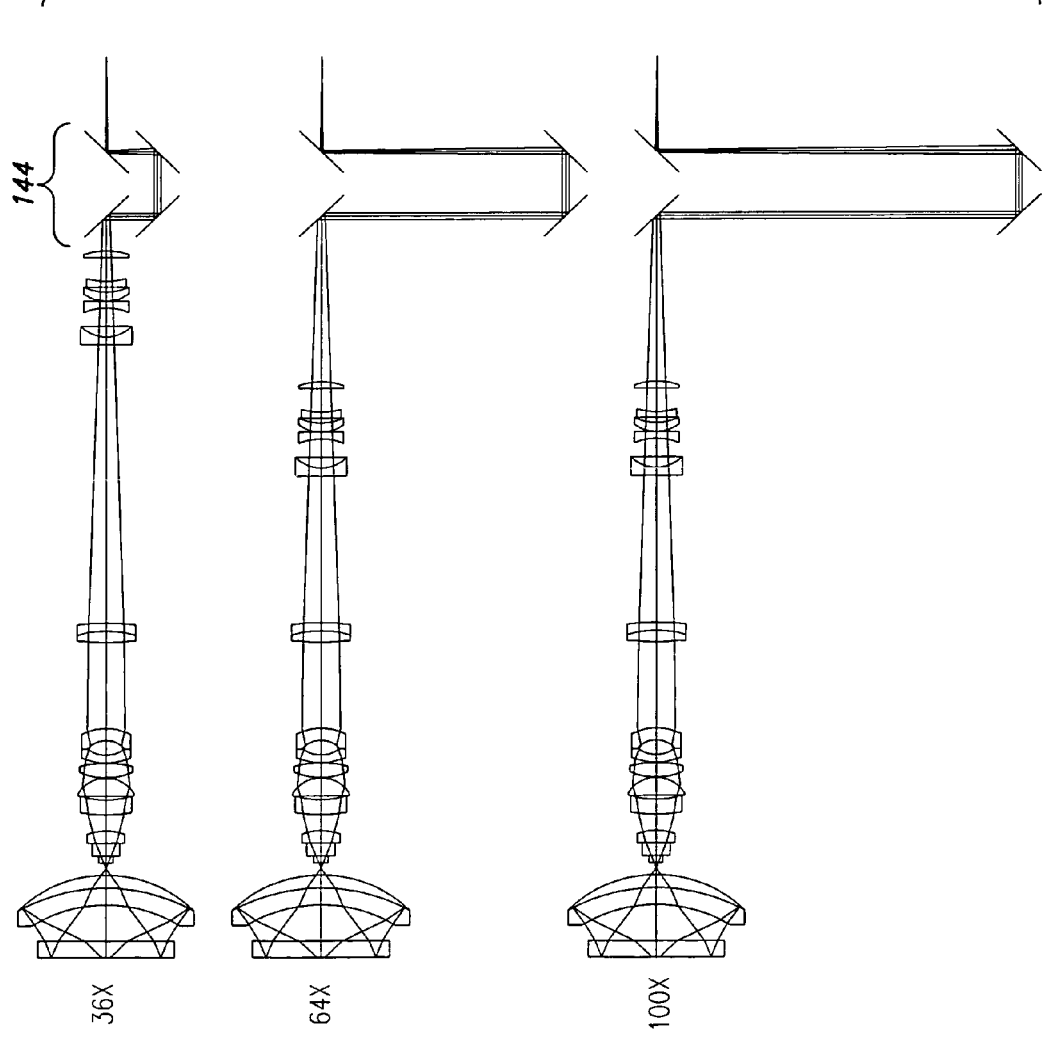
FIG. 43 is a schematic side view of a catadioptric imaging system in three positions having 36×, 64× and 100× power magnification.
Figure 44:
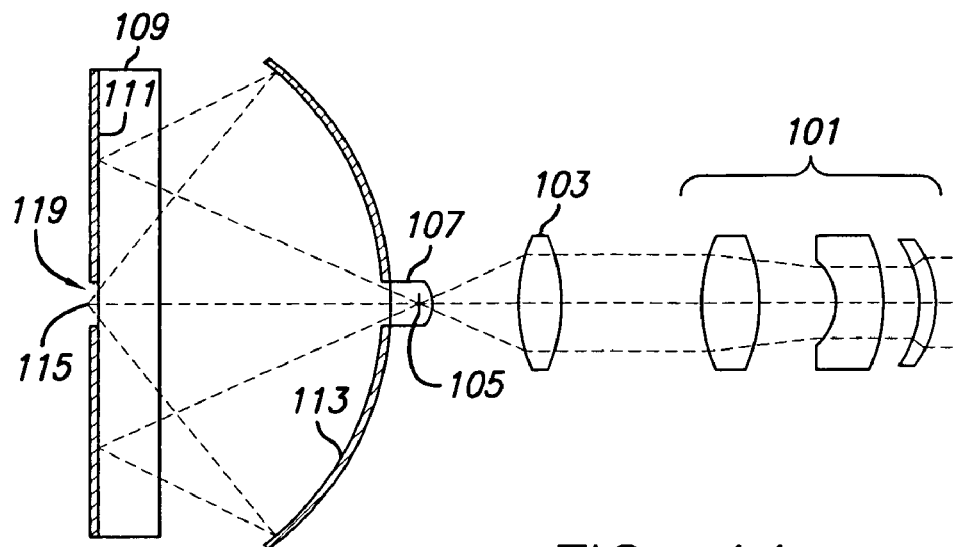
FIG. 44 is a prior art system that completely corrects for primary, secondary and tertiary axial color over a broad wavelength band in the near and deep ultraviolet (0.2 micron to 0.4 micron), but not for residual lateral color.
Figure 45:
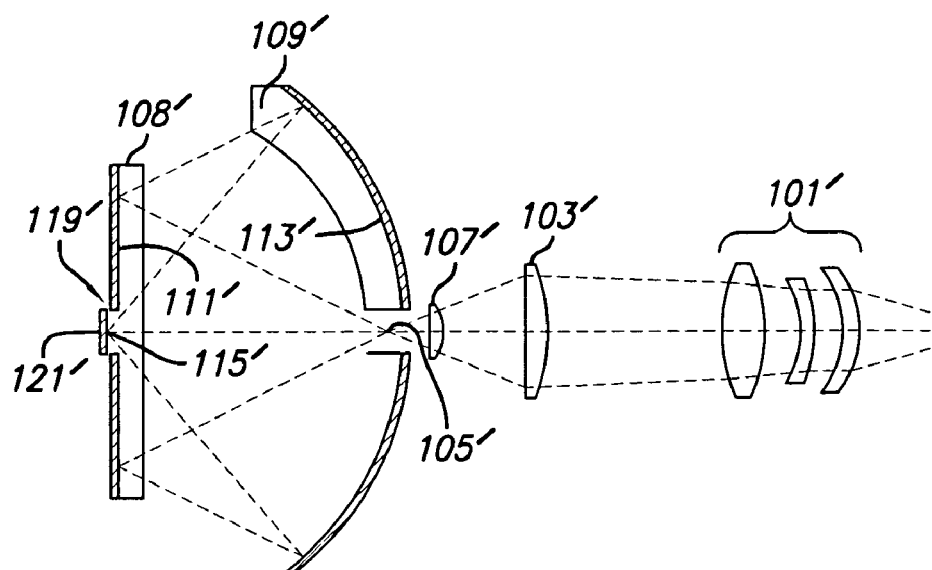
FIG. 45 is a modified version of the '976 Shafer patent optimized for use in 0.193 micron wavelength high power excimer laser applications.

A third aspect of zoom lenses provides linear zoom motion with a fixed sensor position by using the same lens design as the second aspect and incorporating a "trombone" system of reflective elements so that the detector array does not move. FIG. 43 shows the 36× zoom arrangement of the lenses and reflective elements, the 64× zoom arrangement of the lenses and reflective elements and the 100× zoom arrangement of the lenses and reflective elements. The folding mirror group 144 is the "trombone" system of reflective elements. This folding mirror arrangement is just one example. Many other arrangements are possible, such as, using a different number of reflective elements.

Module Transfer Function curves (not shown) indicate that the FIG. 43 aspect is essentially perfect at 64× and 100×, and is good at 36×. Zooming is done by moving a group of six lenses, as a unit, and also moving the arm of the trombone slide. Since the trombone motion only affects focus and the f-speed at location is very slow, the accuracy of this motion could be very loose. One advantage of the trombone aspect is that it significantly shortens the system. Another advantage is that there is only one zoom motion that involves active (non-flat) optical elements. And the other zoom motion, with the trombone slide, is insensitive to errors.

Figure 15:
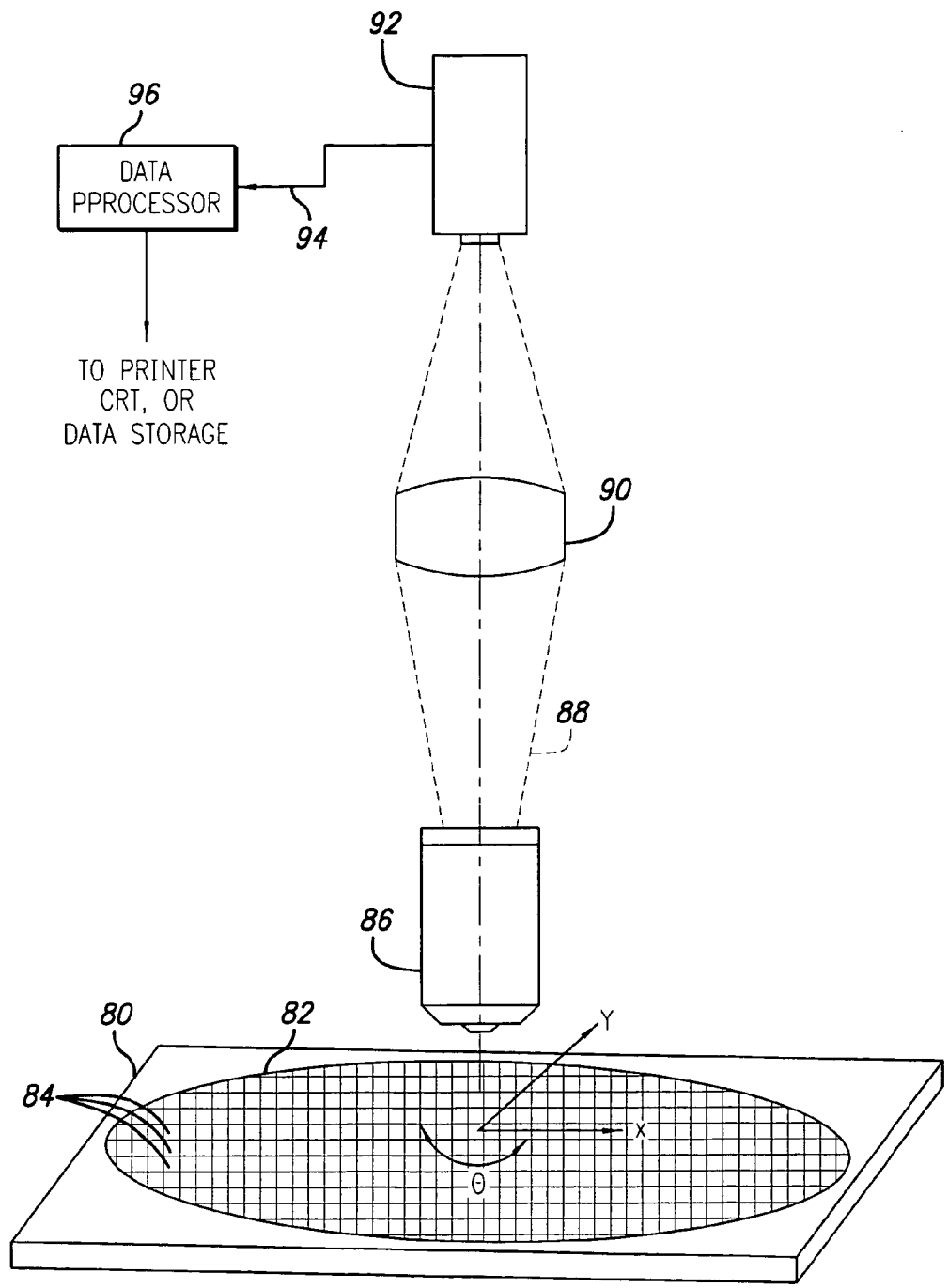
FIG. 15 is a schematic side view of a zooming catadioptric imaging system in an application for the inspection of specimens including semiconductor wafers.

FIG. 15 is a schematic side view of a catadioptric imaging system with a zoom in an application for the inspection of semiconductor wafers. Platform 80 holds a wafer 82 that is composed of several integrated circuit dice 84. The catadioptric objective 86 transfers the light ray bundle 88 to the zooming tube lens 90 which produces an adjustable image received by the detector 92. The detector 92 converts the image to binary coded data and transfers the data over cable 94 to data processor 96.

Figure 16:
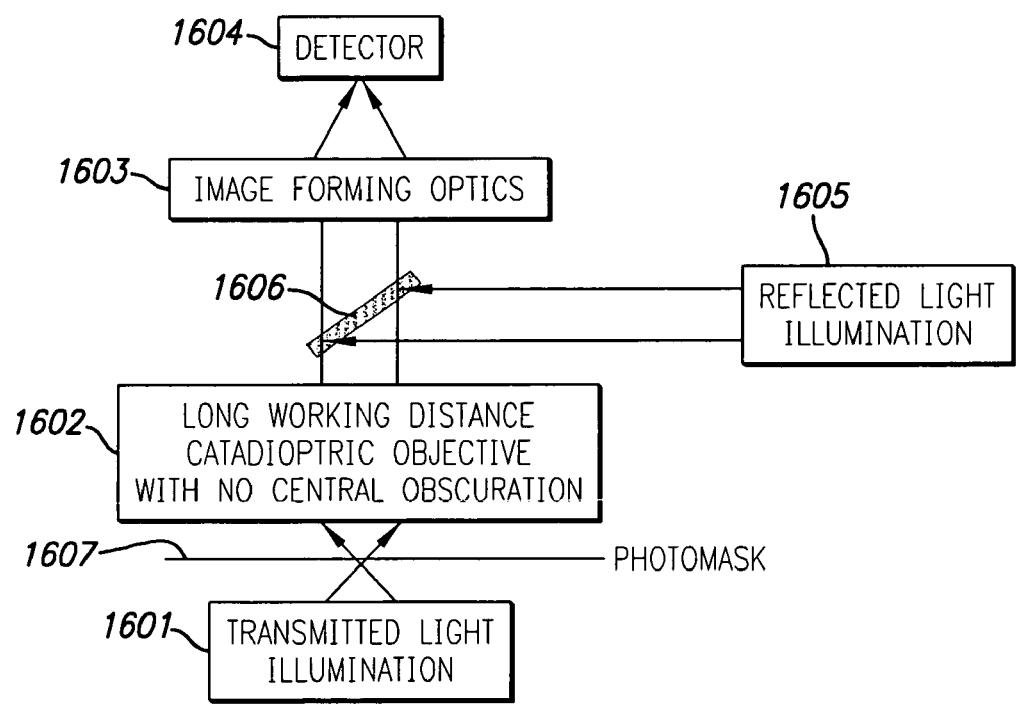
FIG. 16 illustrates a method of optical imaging and bright field and dark field inspection at wavelengths at or below 365 nm.

A further aspect of the present design is that of operating in deep ultraviolet or vacuum ultraviolet conditions. In one aspect of the deep ultraviolet/vacuum ultraviolet design, a method of bright field or ring dark field inspection, and is illustrated in FIG. 16. This method is particularly suited for photomask or wafer inspection and comprises illumination optics such as transmission illumination source 1601 or reflected illumination source 1605, a long working distance catadioptric imaging objective 1602, image forming optics 1603, and a detector 1604. For wafer inspection, only reflected light illumination would be required. The design of the long working distance catadioptric objective and the image forming optics are enabling technologies for photomask inspection at wavelengths at or below 365 nm. The optics and detector are all carefully designed and optimized for the wavelength and spectral bandwidth of the illumination.

Different types of illumination sources may be employed in this design and incorporated in the transmitted light illumination 1601 and reflected light illumination 1605 and with the designs of aspects 3–10 and with respect to FIGS. 47–59. These light sources include but are not limited to excimer lasers and lamps. Different wavelength lasers are possible using frequency mixing techniques. Many different lamp sources are available including mercury xenon (365–220 nm), cadmium lamp (210–220 nm), deuterium (150–190 nm), as well as various excimer lamps. These sources can have very different spectral bandwidths. For example, an unnarrowed excimer laser, a lamp with a bandpass filter, or a frequency converted laser can each produce light having a 1 nm bandwidth or less. An unfiltered lamp or lamp with a larger bandpass filter, such as an arc lamp, excimer lamp, or a deuterium lamp, are also possible sources having bandwidth greater than 1 nm. Relatively few light sources are available at 193 nm and 157 nm wavelengths. Of these light sources, excimer lasers have the brightness required to support high speed photomask inspection. The illumination used in this aspect can be either transmitted light, shown as transmitted illumination source 1601, reflected light, shown as reflected illumination source 1605, or both. As noted, the illumination may also be in the form of a ring such as required for ring dark field imaging. For example, this ring illumination can be obtained by placing a ring shaped aperture at or near a pupil plane located in the illumination system. This aperture may block small illumination angles near the optical axis of the pupil and allow higher illumination angles away from the optical axis of the pupil. This ring should be matched to a similar ring in the catadioptric objective or image forming optics such that all the rays from the illumination ring are blocked in the image.

Note that in the case of the reflected illumination source that beamsplitter/reflector 1606 is employed. In the case of transmitted illumination using transmitted illumination source 1601, photomask 1607 is disposed between transmitted illumination source 1601 and objective 1602. The illumination system for transmitted light may preferably employ a condenser objective. The purpose of the condenser objective is to illuminate a region nominally the same size as the imaging region on a wafer or photomask. As the condenser objective is used only for illumination, it does not require high optical quality. Such an objective can be a reduced performance version of the catadioptric objectives presented in this system or a simple all refractive design. Such designs are possible for those skilled in the art when presented with this disclosure. The illumination for reflected light uses a beamsplitter and is implemented as in a standard microscope.

The long working distance imaging objective 1602 includes those described in designs 3 through 8 and illustrated in FIGS. 47–57. The objective working distance may be greater than 6 mm so it will not interfere with a pellicle that protects the photomask. The objective may also be well corrected for aberrations over the bandwidth of the illumination source. Many of the available illumination sources have a bandwidth that is greater than the 1–2 pm bandwidth obtained from a standard type of single material all refractive objective design. An example of this is an unnarrowwed excimer laser that typically has a spectral bandwidth around 1 nm. The catadioptric designs 3–8 address this problem. The objective may also be capable of imaging over a large field. Large fields and high data acquisition rates are essential to make inspecting the photomask as fast as possible. There are similar requirements for wafer inspection, however a shorter working distance is possible.

The image forming optics 1603 may be corrected over the spectral bandwidth of the illumination source and the catadioptric imaging objective. The image forming optics 1603 should also be capable of various magnifications required in a photomask inspection environment. The image forming optics 1603 and the catadioptric objective 1602 may each and together be fully corrected for aberrations. Such aberration correction permits testing the image forming optics 1603 and the catadioptric objective 1602 as separate units. Alternately, aberration correction may be shared between the catadioptric objective 1602 and the image forming optics 1603.

The image forming optics or catadioptric objective may also contain a ring aperture at or near a pupil plane such as required for ring dark field imaging. This aperture may block all direct illumination light from reaching the detector, corresponding to a similar aperture in the illumination. Thus the illumination aperture may be a transmissive ring and the imaging aperture may be a corresponding opaque ring. Combinations of bright field imaging and ring dark field imaging are also possible. They may be combined on separate detectors or on the same detector at the same times or in an alternate fashion. When on the same detector at the same time, the relative intensity and phase can be modified by suitable apertures in the illumination and imaging.

In the DUV-VUV aspect of the current design, the detector 1604 is preferably a high speed detector capable of the high data rates used for inspection systems. Detector 1604 can be a single point diode type detector or an area type detector such as a CCD or a CCD operating in the Time Delay and Integration (TDI) mode. This detector 1604 may have a high quantum efficiency, low noise, and a good Modulation Transfer Function (MTF). Back thinned CCD sensors can be used for this purpose.

Figure 46:
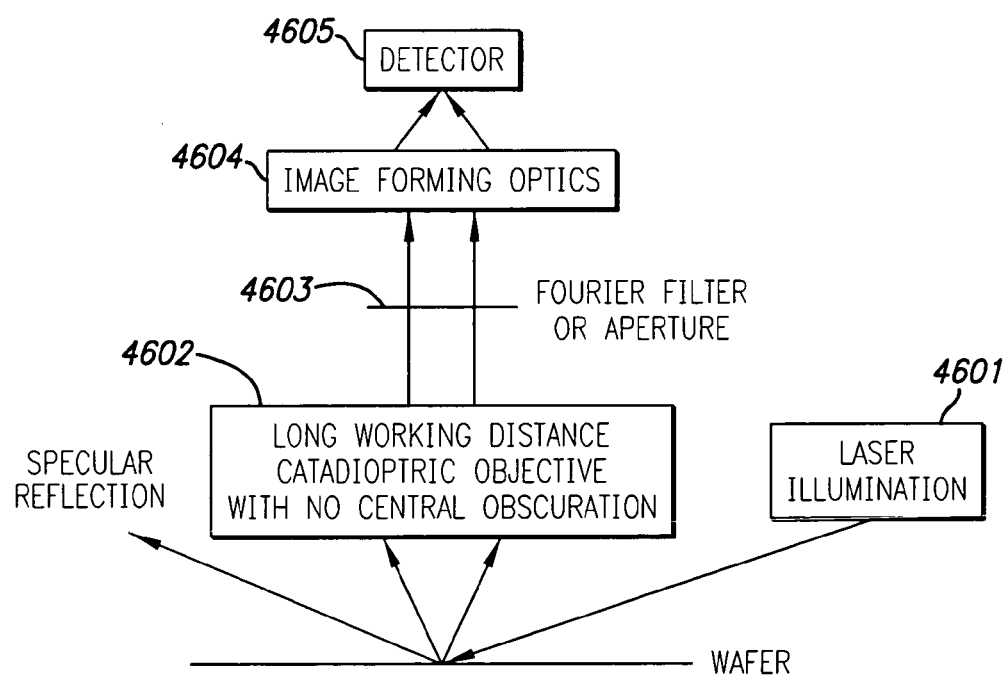
FIG. 46 illustrates a method of optical imaging and inspection using laser dark-field at wavelengths at or below 365 nm.

The second aspect is a method for laser dark-field inspection at or below 365 nm, and is illustrated in FIG. 46. It is suited for wafer and photomask inspection. This apparatus consists of illumination optics, such as laser illumination element 4601, a long working distance catadioptric imaging objective 4602, a Fourier filter or aperture 4603 at the external pupil plane, image forming optics 4604, and a detector 4605. Catadioptric imaging designs using two glass materials are achievable when using an excimer laser illumination source with greater than 1 nm bandwidth.

The types of illumination that can be used for this system are similar to those used for bright field and ring dark field inspection. One method or apparatus for laser-dark field illumination of a semiconductor specimen is direct illumination of the specimen from outside the objective. In such an arrangement, only light scattered from the specimen is collected by the catadioptric objective. The specularly reflected beam is beyond the numerical aperture of the objective and is not collected.

Again, the long working distance imaging objective 4602 is described with respect to FIGS. 47–57. For laser dark field inspection, these designs should fulfill certain basic requirements. The long working distance offered by the designs of FIGS. 47–57 simplifies delivering laser energy to the wafer in the semiconductor specimen environment from outside the objective without interfering with the operation of the imaging system. The objective is preferably also well corrected for aberrations over the bandwidth of the illumination source 4601. Many of the available illumination sources have a bandwidth that is greater than the 1–2 pm bandwidth obtained from a standard type of single material all refractive objective design. The objective 4602 images over a large field, as large fields and high data acquisition rates provide for rapid wafer or photomask inspection.

The objective also preferably has an easily accessible pupil plane to support Fourier filtering or aperturing, such as by the Fourier filter or aperture 4603. Fourier filtering can reduce the noise caused by repeating patterns on the wafer, thereby permitting smaller random defects to be more readily detected.

The image forming optics 4604 may be corrected over the spectral bandwidth of the illumination and the catadioptric imaging objective 4602. The image forming optics 4604 also preferably support the various magnifications required by a dark field inspection system. One implementation of the image forming optics 4604 is to have them and the catadioptric objective 4602 each fully corrected for aberrations. Such a system allows simplified testing of image forming optics 4604 and the catadioptric objective 4602 as separate units. An alternate technique is sharing aberration correction between the catadioptric objective 4602 and the image forming optics 4604. Such an approach can be mechanically or optically simpler, but can complicate image forming optics and catadioptric objective testing.

Again, as shown in FIG. 16, the detector 4605 is preferably a high speed detector capable of the high data rates used for an inspection system. Detector 4605 can be a single point diode type detector or an area type detector such as a CCD or a CCD operating in the Time Delay and Integration (TDI) mode. Ideally, this detector should have a high quantum efficiency, low noise, and a good Modulation Transfer Function (MTF). Such detectors are generally known to by those skilled in the art.

The design of FIGS. 16 and 46 can support bright field, laser directional dark field, ring dark field, and simultaneous bright-field and dark-field schemes, where each of these schemes can be achieved in the presence of UV, DUV, and VUV wavelengths. The opaqueness of CMP layers in the deep UV and VUV ranges makes a system using this objective ideally suited to finding surface defects and microscratches on semiconductor wafers.

The catadioptric optical apparatus presented to support bright field and dark field imaging and inspection are also ideal for use in a variety of other applications. The design can be easily optimized by one skilled in the art for wavelengths from the visible range to the deep UV range and to the vacuum UV range. Longer wavelengths can be optimized for larger bandwidths because the glass dispersion is less. For example, bandwidths of greater than 140 nm are possible with a two material design and a center wavelength of 300 nm. The light energy can include shorter wavelengths and the design permits use of multiple wavelengths. For semiconductor inspection, the designs presented can support bright field, laser directional dark field, ring dark field, and simultaneous bright-field and dark-field schemes. The optical designs presented are also suited for use as a lithography lens or for lithography simulation, a research tool for microelectronic development, florescence measurements, or in biology where a long working distance is required for sample clearance. Due to the ability of this objective to provide applications in the presence of extremely varied light wavelengths and spectral bandwidths, the designs in FIGS. 16 and 46 are well suited for florescence measurements.

FIG. 47 illustrates a third aspect of the design. This third aspect is simple example of a folded 0.7 NA catadioptric objective 300 utilizing a single glass material. This example is presented mainly to simplify the explanation of the aberration correction and objective functionality. FIG. 47 includes a line in the upper left corner indicating a reference measurement of the number of millimeters the line represents. Also, as in other figures discussed herein, light is shown entering from the left side of FIG. 47 from an excimer laser energy source 47000 (not shown). The energy from the energy source 47000 is focused by a group of positive and negative lenses 4701 arranged in either a telephoto or inverse telephoto configuration. The positive lens may be either in the front or in the back of the arrangement, where front and back are relative terms with respect to the energy source. Here negative lens 4702 is in front of positive lens 4703, where negative lens 4702 and positive lens 4703 form the group of positive and negative lenses 4701. A positive field lens 4704 is located somewhat in front of the focus for lens group 4701. Very close to the small image formed is located a relatively small pair of flat fold mirrors 4705 arranged in a V-shape. The first small flat mirror 4705a reflects the light at 90 degrees to the optical axis. Some other angular amount may be used depending on the application desired while still within the course and scope of the present system. The diverging light then proceeds to the Mangin mirror 4706 located at the bottom of FIG. 47. A Mangin mirror is a lens/mirror element that is refractive and has a reflective back surface. The Mangin mirror 4706 re-images the first image onto the second small flat folding mirror 4705b, at substantially unit magnification. The system is implemented far enough off axis such that the returning second image is displaced laterally enough from the first image so that the lateral separation permits optical manipulation of each separate image. The amount of lateral separation allows the second small flat mirror 4705b to fold the light path back onto the original optical axis. This effect is illustrated in FIG. 48.

According to FIG. 48, the input rays in the field of the substantially unit magnification Mangin mirror relay are on one side of the field and the output rays are on the opposite side. From FIG. 47, the second small fold mirror 4705b is followed by a second field lens 4707. From there the light proceeds up to the final focusing lenses 4708 discussed below. This final focusing lens group 4708 provides a relatively long working distance to the surface of the specimen, such as the photomask or semiconductor wafer.

If the two field lenses were not present in the design of FIG. 47, this design would constitute an application of the Schupmann type design using a Mangin mirror. The Mangin mirror would provide the means by which the virtual image of the Schupmann system would be turned into a real image, just as shown in previously known systems. This new configuration provides two significant advantages over the previous designs: lack of obscuration and a relatively long working distance. Both advantages result from the novel arrangement of the small fold mirrors 4705, the substantially unit magnification Mangin mirror 4706, and the presence of the two intermediate images in the system.

The small fold mirrors 4705 can be implemented in a variety of ways. Objective designs can be optimized where these fold mirrors are on the sides of the field lenses opposite to the internal images. Objective designs can also be optimized where the small fold mirrors are on the side of the internal image closest to the Mangin mirror. Also, a prism or prisms can be used for the reflective surfaces in a variety of ways. A reflective coating can be added to one or more of the prism surfaces. Two prisms can then be used as reflective mirrors. Alternately, one prism can have two surfaces coated and serve as both reflective surfaces. This is advantageous because a highly accurate angle can be polished on the prism to define the angle of the optical axis. The prisms can also be used in total internal reflection mode. This is advantageous when high efficiency optical coatings are difficult, such as for short wavelengths or broad spectral bandwidths.

In this mode, the hypotenuse of a near 90 degree prism is used in total internal reflection, replacing a reflecting surface. The surfaces of the prism that are near normal to the incoming and reflecting beams may be anti reflection coated to improve transmission efficiency.

Addition of one field lens to the system, in either of the two locations where the design has its two field lenses, provides the ability to correct the design for either secondary axial color or primary lateral color. Primary axial color is corrected without field lenses by balancing the positive refractive power of the Mangin mirror element 4706 with the positive power of the lenses, as in connection with the Schumpmann principle. Use of two field lenses 4704 and 4707 near the intermediate images provides for correction of both secondary axial color and primary lateral color. The result is a design with a fairly broad spectral range having good axial color correction, but one that is limited by secondary axial color. Correction of the secondary lateral color can be accomplished by balancing the secondary color between the first half of the system with the second half of the system, where the first half of the system includes all lenses from the incoming energy source up to the reflective portion of the Mangin mirror 4706, including lens group 4701, field lens 4704, first small fold mirror 4705a, and Mangin mirror 4706. This secondary lateral color balancing scheme works well due to the two intermediate images produced as in FIG. 48 and the two separate field lenses 4704 and 4707 present in the system. As in known systems, tertiary axial color is improved by moving the field lenses 4704 and 4707 a significant distance to one side of the intermediate images.

The present design is a catadioptric system requiring a single refractive material, in conjunction with the particularly described arrangement of mirrors, to correct for chromatic aberrations. For a design intended for use in the presence of an excimer laser source wavelength near 193 nm, the preferred lens material is silica. For a similar design intended for use in wavelengths near 157 nm, the preferred lens material is $CaF_2$. At 157 nm wavelength, for example, $CaF_2$ is preferred since it does not have severe problems with birefringence, water solubility, or mechanical softness. Further chromatic correction can also be achieved using two glass materials, but such an arrangement may require additional cost or present birefringence, water solubility, or mechanical softness drawbacks.

Special challenges are presented when correcting various color aberrations when only one glass type is used. Conventional designs usually use two or three glass types to correct color aberrations. The present invention performs the correction in the presence of a single material type used in all lenses due to the specific lens and mirror configuration. In very deep UV, both silica and $CaF_2$ are highly dispersive, so even a narrow spectral bandwidth at very short wavelengths can require the correction of quite a few distinct color aberrations. Such color aberrations may include primary and secondary axial color, primary and secondary lateral color, chromatic variation of spherical aberration, and chromatic variation of coma. In the present system, lens and mirror positioning permits primary axial and lateral color to be completely corrected. Secondary axial and lateral color cannot be completely corrected, but can be kept small enough to be acceptable over a relatively narrow spectral bandwidth. Chromatic variation of both spherical aberration and coma can also be corrected using this small fold mirror and dual field lens design. The physical separation between positive and negative axial color contributions present in the design of FIG. 47, particularly the separation to positionally disparate locations within the design, leads to special problems in correcting the chromatic variation of aberrations. Minimization of chromatic aberration variations requires a very particular arrangement of lens powers and shapes such as illustrated in FIG. 47 and later in designs 4–8.

The design of FIG. 47 provides an optical system having a long working distance between the optical system and the surface being inspected, particularly between the final lens in the system 4708 and the surface of the object or specimen 4709 (not shown) being imaged. The arrangement of FIG. 47 further provides a high numerical aperture and no central obscuration. A high numerical aperture provides for high resolution imaging and collecting as large an angular range above the surface being imaged as possible. Numerical apertures of greater than 0.8 can be achieved in the DUV-VUV inspection design with excellent performance. A numerical aperture of 0.8 corresponds to collecting angles above the surface from normal to 53 degrees. Further, unlike many catadioptric optical systems, the design of FIG. 47 has no central obscuration to block low frequency information. The FIG. 47 design does not have this problem and permits utilization of all low frequency information.

The design illustrated in FIG. 47 also provides relatively reasonable tolerances which can be more easily manufactured. The benefit of reasonable tolerances in the design of FIG. 47 is that it overcomes problems present in many known high NA, broad bandwidth systems having some optical elements with very tight position and thickness tolerances. These tight tolerances may make previous designs either too expensive or in some cases impossible to build and operate in a production environment.

Figure 49:
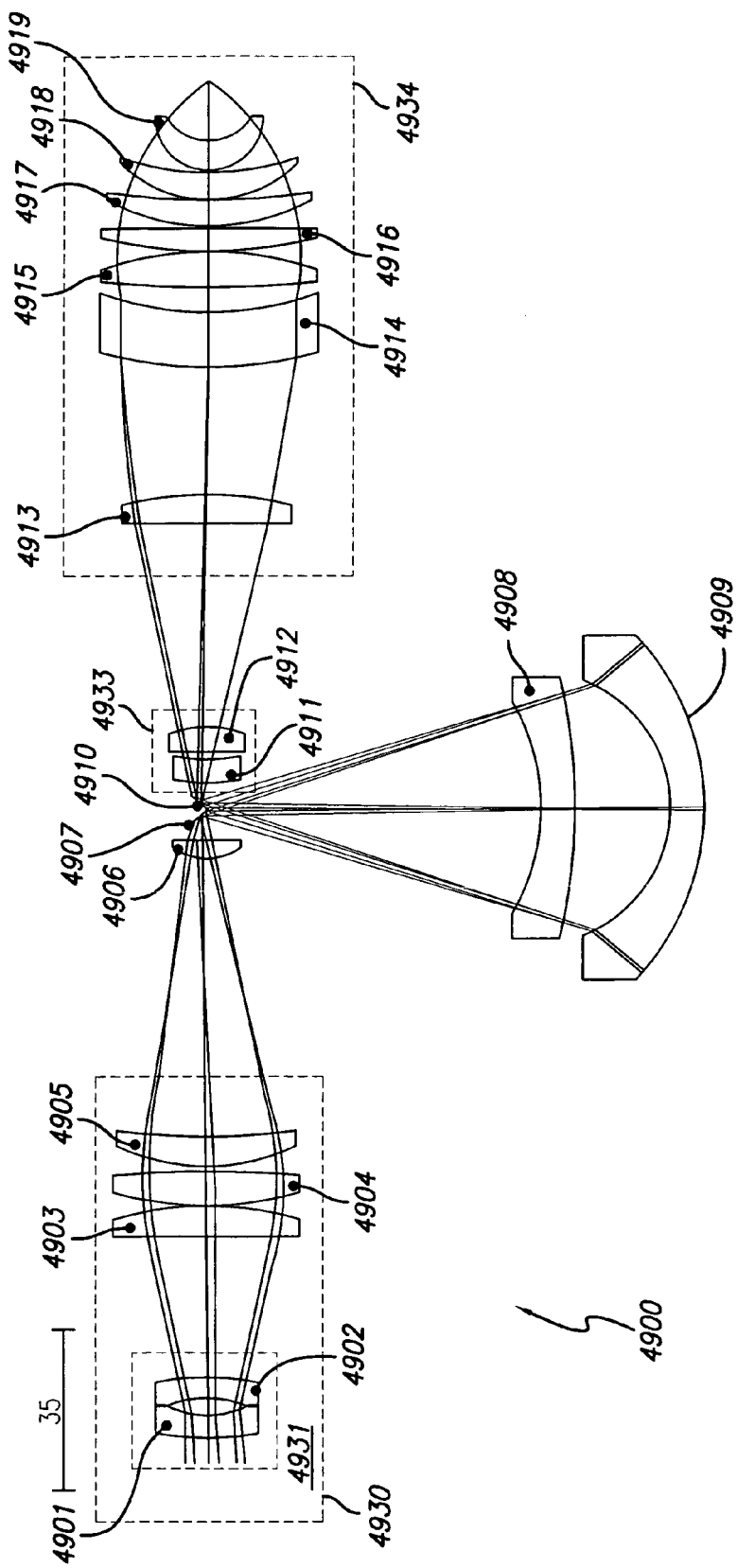
FIG. 49 presents an aspect of the design that provides narrow band aberration correction to give a 0.7 NA, long working distance, unobscured design using only fused silica.

FIG. 49 shows a more complex version of the design that provides additional narrow band aberration correction to give a 0.7 NA, long working distance, unobscured design using only fused silica. The object extends from 0.25 mm to 0.75 mm off axis and the design has a bandwidth of 1 nm from 192.8–193.8 nm. The surface data for an example of this type of design is listed in Table 1. Performance for the system shown in FIG. 49 is limited by chromatic variation in aberrations rather than higher order axial color. Other versions are possible and would require minimal effort by those of ordinary skill when presented with this disclosure.

As illustrated in FIG. 49, energy, such as laser energy, is transmitted from energy source 49000 (not shown) and into objective 4900. Objective 4900 includes lens arrangement 530, which includes a first lens pair 531 including first lens 4901 and second lens 4902, followed by third lens 4903, fourth lens 4904, and fifth lens 4905. Energy is focused by lens arrangement 4930 toward field lens 4906, which then directs energy toward the small folding mirror or reflecting surface, here specifically first mirror 4907. Energy is directed from first mirror 4907 toward lens 4908 and to Mangin mirror 4909, which reflects light energy back through lens 4908 and toward the second part of the small folding mirror or reflecting surface, specifically to second mirror 510.

In FIG. 49, light is reflected from second folding mirror 4910 to field lens 4933, which includes first field lens 4911 and second field lens 4912. From the field lens 4933, light is transmitted to focusing lens arrangement 4934, which includes first focusing lens 4913, second focusing lens 4914, third focusing lens 4915, fourth focusing lens 4916, fifth focusing lens 4917, sixth focusing lens 4918, and seventh focusing lens 4919. The specimen or surface 520 to be examined is not shown in FIG. 49, but is located to the right of the objective 4900 in the orientation of FIG. 49. Light energy strikes the specimen and reflects back through the objective 4900 of FIG. 49. Alternately, light energy can transmit through the specimen and then through the objective 4900 from right to left as shown in FIG. 49.

TABLE 1

Surface data for the folded design of FIG. 5 operating at 193 nm wavelength with a 1 nm bandwidth

| Surf | Radius | Thickness* | Material | Element Number |
|---|---|---|---|---|
| OBJ | Infinity | Infinity | | N/S** |
| STO | Infinity | −32.038 | | N/S |
| 2 | 81.983 | 5.000 | Silica | 4901 |
| 3 | 18.305 | 4.216 | | 4901 |
| 4 | −27.049 | 5.000 | Silica | 4902 |
| 5 | −61.738 | 33.261 | | 4902 |
| 6 | 1276.054 | 7.000 | Silica | 4903 |
| 7 | −83.831 | 0.500 | | 4903 |
| 8 | 79.482 | 8.000 | Silica | 4904 |
| 9 | −229.250 | 1.000 | | 4904 |
| 10 | 47.191 | 7.000 | Silica | 4905 |
| 11 | 138.080 | 66.471 | | 4905 |
| 12 | 14.544 | 4.000 | Silica | 4906 |
| 13 | 514.189 | 7.697 | | 4906 |
| 14 | Infinity | 0.000 | Mirror | 4907 |
| 15 | Infinity | −77.947 | | 4907 |
| 16 | 50.786 | −8.000 | Silica | 4908 |
| 17 | 139.802 | −22.299 | | 4908 |
| 18 | 32.934 | −8.000 | Silica | 4909 |
| 19 | 60.774 | 8.000 | Mirror | 4909 |
| 20 | 32.934 | 22.299 | | 4909 |
| 21 | 139.802 | 8.000 | Silica | 4908 |
| 22 | 50.786 | 77.947 | | 4908 |
| 23 | Infinity | 0.000 | Mirror | 4910 |
| 24 | Infinity | −3.500 | | 4910 |
| 25 | Infinity | −2.500 | | 4910 |
| 26 | −50.929 | −5.724 | Silica | 4911 |
| 27 | −41.159 | −1.814 | | 4911 |
| 28 | 302.166 | −6.000 | Silica | 4912 |
| 29 | 24.557 | −48.713 | | 4912 |
| 30 | 544.674 | −6.500 | Silica | 4913 |
| 31 | 89.379 | −30.822 | | 4913 |
| 32 | −90.727 | −12.569 | Silica | 4914 |
| 33 | −64.505 | −6.000 | | 4914 |
| 34 | −233.637 | −8.000 | Silica | 4915 |
| 35 | 83.534 | −0.500 | | 4915 |
| 36 | −92.578 | −5.679 | Silica | 4916 |
| 37 | 1208.052 | −0.500 | | 4916 |
| 38 | −50.386 | −5.8316 | Silica | 4917 |
| 39 | −146.956 | −0.500 | | 4917 |
| 40 | −30.274 | −5.971 | Silica | 4918 |
| 41 | −56.351 | −0.500 | | 4918 |
| 42 | −12.744 | −7.155 | Silica | 4919 |
| 43 | −12.195 | −14.453 | | 4919 |
| 44 | Infinity | 1.68E−05 | | N/S |
| IMA | Infinity | | | N/S |

*Surface thickness represents the thickness of a surface when at the "upstream" side of the element or distance between the surface and the next surface if at the "downstream" side of the element. For example, surface 2 on element 4901 has a radius of 81.983 millimeters and the lens is 5.000 millimeters thick. Surface 3 of lens element 4901 has a radius of 18.305 millimeters and is 4.216 millimeters from the next surface, which is surface 4 on element 4902.
**Certain elements relating to but not critical to the design are not shown in the figures.

Figure 50:
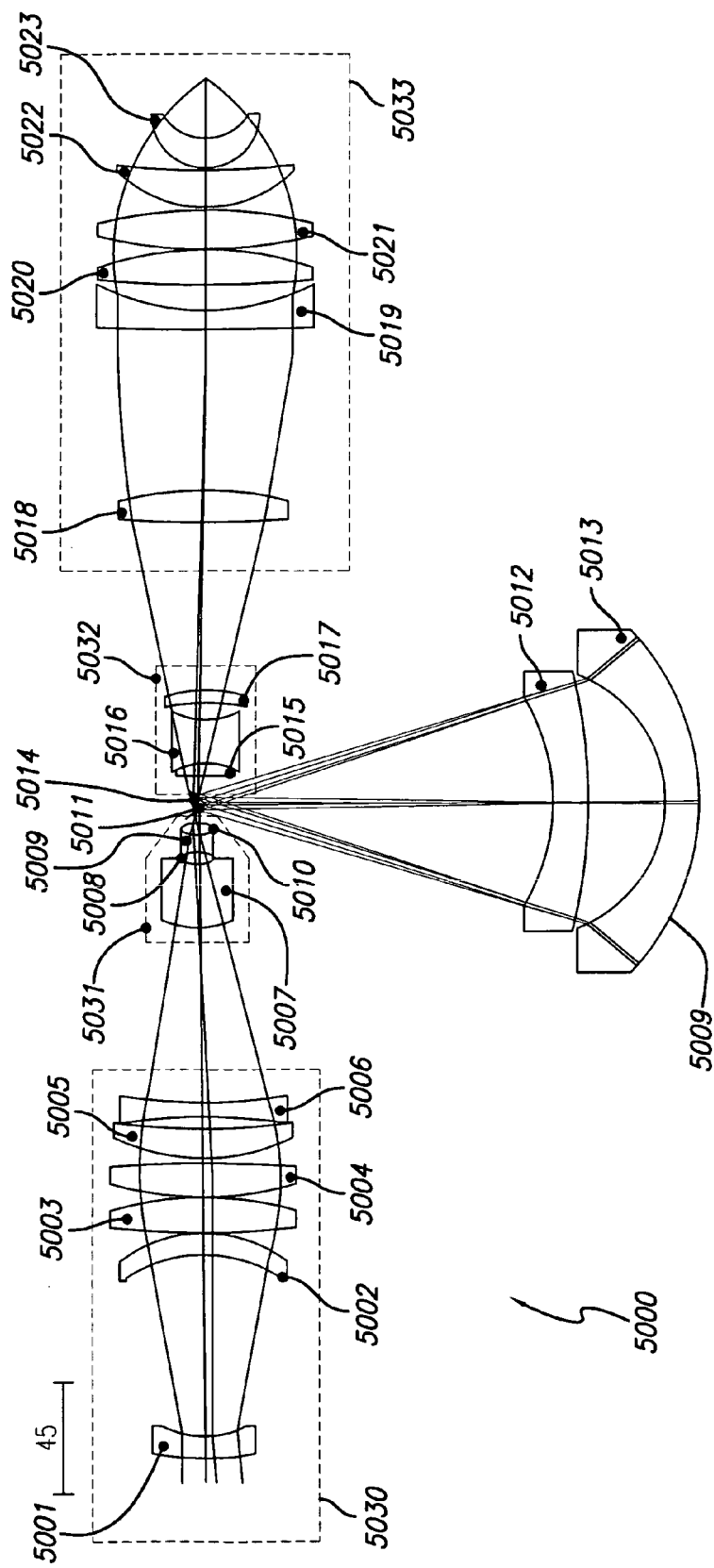
FIG. 50 presents an aspect of the system having a folded 0.7 NA catadioptric objective using silica and calcium fluoride to further increase system bandwidth.

A fourth aspect is presented in FIG. 50. FIG. 50 illustrates a folded 0.7 NA catadioptric objective using two materials. This design uses silica and calcium fluoride to further increase system bandwidth. Calcium fluoride is added to the field lenses in this design make both such lenses achromats. The design of FIG. 50 is corrected for light energy from 193 to 225 nm. Surface data for a system of the fourth aspect is presented in Table 2.

As shown in FIG. 50, light energy or laser energy is transmitted from energy source 50000 (not shown) and into objective 5000. Objective 5000 includes a lens arrangement 5030, which includes first lens 5001, second lens 5002, third lens 5003, fourth lens 5004, fifth lens 5005, and sixth lens 5006. Energy is focused by lens arrangement 5030 toward field lens arrangement 5031, which includes seventh lens 5007, eighth lens 5008, ninth lens 5009, and tenth lens 5010. Eighth lens 5008 and tenth lens 5010 are formed of calcium fluoride (CaF$_2$). This field lens arrangement 5031 directs light energy to first small folding mirror or reflecting surface 5011, which directs energy toward lens 5012 and to Mangin mirror 5013. Light energy reflects back from Mangin mirror 5013 back through lens 5012 and toward the second part of the small folding mirror or reflecting surface, specifically to second mirror 5014.

Light is reflected from second folding mirror 5014 to second field lens arrangement 5032, which includes first field lens 5015, second field lens 5016, and third field lens 5017. Both first field lens 5015 and third field lens 5017 are formed of calcium fluoride. From the field lens arrangement 5032, light energy is transmitted to focusing lens arrangement 5033, which includes first focusing lens 5018, second focusing lens 5019, third focusing lens 5020, fourth focusing lens 5021, fifth focusing lens 5022, and sixth focusing lens 5023. The specimen or surface 5024 to be examined is not shown in FIG. 50, but is located to the right of the objective 5000 in the orientation of FIG. 50.

TABLE 2

Surface data for a folded design at 193 nm with a 32 nm bandwidth

| Surf | Radius | Thickness | Material | Element Number |
|---|---|---|---|---|
| OBJ | Infinity | Infinity | | N/S |
| STO | Infinity | −32.204 | | N/S |
| 2 | −101.014 | 3.000 | Silica | 5001 |
| 3 | 25.381 | 74.761 | | 5001 |
| 4 | −29.809 | 5.000 | Silica | 5002 |
| 5 | −31.309 | 1.000 | | 5002 |
| 6 | 183.355 | 7.500 | Silica | 5003 |
| 7 | −109.361 | 0.500 | | 5003 |
| 8 | 99.287 | 7.000 | Silica | 5004 |
| 9 | −250.439 | 1.000 | | 5004 |
| 10 | 50.010 | 5.500 | Silica | 5005 |
| 11 | 118.693 | 3.882 | | 5005 |
| 12 | −216.754 | 4.000 | Silica | 5006 |
| 13 | 127.307 | 44.956 | | 5006 |
| 14 | 28.389 | 24.000 | Silica | 5007 |
| 15 | 7.676 | 0.683 | | 5007 |
| 16 | 12.387 | 3.000 | CaF$_2$ | 5008 |
| 17 | −10.095 | 0.475 | | 5008 |
| 18 | −8.982 | 5.497 | Silica | 5009 |
| 19 | 8.000 | 0.093 | | 5009 |
| 20 | 8.069 | 3.000 | CaF$_2$ | 5010 |
| 21 | −9.002 | 5.673 | | 5010 |
| 22 | Infinity | 0.000 | Mirror | 5011 |
| 23 | Infinity | −94.049 | | 5011 |
| 24 | 60.160 | −8.000 | Silica | 5012 |
| 25 | 158.201 | −20.471 | | 5012 |
| 26 | 34.636 | −8.000 | Silica | 5013 |
| 27 | 65.450 | 8.000 | Mirror | 5013 |
| 28 | 34.636 | 20.471 | | 5013 |
| 29 | 158.201 | 8.000 | Silica | 5012 |
| 30 | 60.160 | 94.049 | | 5012 |
| 31 | Infinity | 0.000 | Mirror | 5013 |
| 32 | Infinity | −3.500 | | 5013 |
| 33 | Infinity | −2.500 | | 5013 |
| 34 | −26.228 | −2.500 | CaF$_2$ | 5014 |
| 35 | 12.608 | −0.102 | | 5014 |
| 36 | 12.417 | −9.995 | Silica | 5015 |
| 37 | −34.270 | −2.110 | | 5015 |
| 38 | 70.277 | −2.000 | CaF$_2$ | 5016 |
| 39 | 25.599 | −36.553 | | 5016 |
| 40 | −139.138 | −7.000 | Silica | 5017 |
| 41 | 75.025 | −63.911 | | 5017 |
| 42 | −347.832 | −6.000 | Silica | 5018 |

TABLE 2-continued

Surface data for a folded design at 193 nm with a 32 nm bandwidth

| Surf | Radius | Thickness | Material | Element Number |
|---|---|---|---|---|
| 43 | −60.817 | −6.000 | | 5018 |
| 44 | −125.144 | −9.000 | Silica | 5019 |
| 45 | 146.610 | −0.500 | | 5019 |
| 46 | −69.321 | −9.000 | Silica | 5020 |
| 47 | 482.420 | −0.500 | | 5020 |
| 48 | −44.275 | −10.217 | Silica | 5021 |
| 49 | −474.223 | −0.500 | | 5021 |
| 50 | −19.707 | −10.437 | Silica | 5022 |
| 51 | −30.002 | −18.250 | | 5022 |
| 52 | Infinity | 3.14E−05 | | N/S |
| IMA | Infinity | | | |

It is also possible to use a diffractive optic instead of a second glass material to increase the bandwidth. In this case, the diffractive optic must be manufactured with a specific phase profile to ensure proper diffraction efficiency and angles. This would be possible for those skilled in the art once presented with this disclosure.

The aspects illustrated in FIGS. 49 and 50 have two disadvantages. First, the optical axis of the Mangin mirror image relay is at 90 degrees to the optical axis defined by the focusing lenses. This arrangement can mandate very high angular and position tolerances for the optical elements in the Mangin mirror image relay. This can result in manufacturing difficulties and increased system cost. For this reason, it is desirable to have a minimum number of lens elements in this 90 degree path. Thus, the 90 degree optical axis can limit the design options for this objective. Second, the pupil plane for aperturing and Fourier filtering is located in a noncollimated region inside the objective. This can produce problems for introducing apertures and filters. Also, because the pupil is in a noncollimated region, it is not at the Fourier plane of the object being inspected. This can significantly reduce the effectiveness of Fourier filtering.

Figure 51:
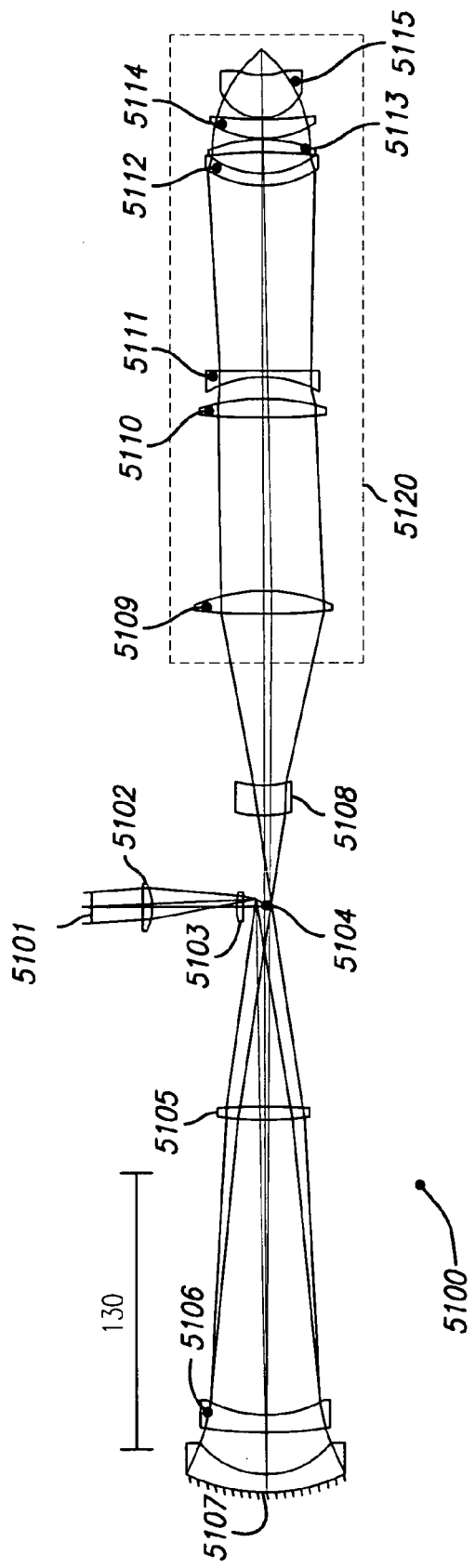
FIG. 51 presents an aspect of the system having an in-line or straight 0.7 NA catadioptric objective employing a single glass material.
Figure 52:
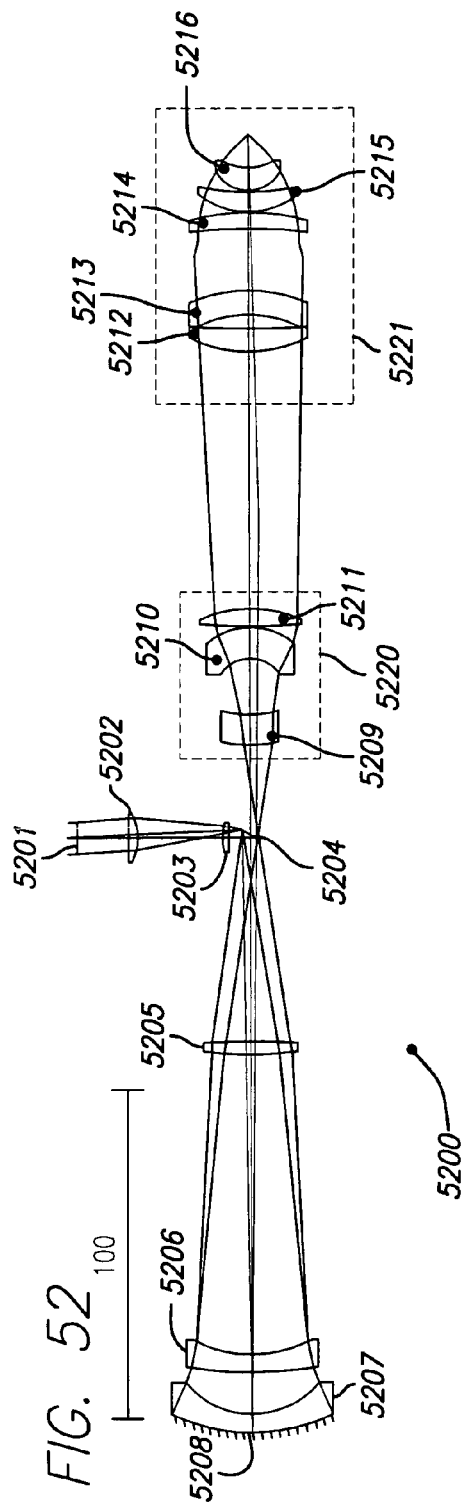
FIG. 52 presents an aspect of the system optimized for a wavelength of 157 nm wherein the lenses shown are fashioned from calcium fluoride.

The fifth aspect, illustrated in FIG. 51, solves the problems of the 90 degree bend issue with respect to the Mangin mirror image relay and the internal pupil plane. FIG. 52 illustrates an in-line or straight 0.7 NA catadioptric objective employing a single glass material. The arrangement of FIG. 51 also allows for improved design performance and relaxes manufacturing tolerances. For example, the decentering of any lens element by 5 microns will cause less than one quarter wave of coma without using any compensation elements. Using element decenters and tilts as compensation elements, the tolerances become even more relaxed. The arrangement of FIG. 51 includes one bend with some lenses after the second internal image. These lenses have extremely relaxed tolerances and tend not to affect the manufacturability of the system. The arrangement of FIG. 51 also has an external pupil plane 5101 for aperturing and Fourier filtering. This pupil plane is in the collimated region so it corresponds to the Fourier plane of the object. The object in the arrangement of FIG. 51 extends from 0.25 mm to 0.75 mm off axis and the design has a bandwidth of 1 nm from 192.8–193.8 nm.

As shown in FIG. 51, light energy or laser energy is transmitted from energy source 51000 (not shown) and into objective 5100. Objective 5100 includes first lens 5102 and first field lens 5103. This first field lens 5103 directs light energy to small folding mirror or reflecting surface 5104, which directs energy toward focusing lenses 5105 and 5106 and to Mangin mirror 5107. Light energy reflects back from Mangin mirror 5107 back through focusing lenses 5106 and 5105 and past small folding mirror or reflecting surface 5104. Light energy then passes through second field lens 5108 and through focusing lens arrangement 5120, which includes first focusing lens 5109, second focusing lens 5110, third focusing lens 5111, fourth focusing lens 5112, fifth focusing lens 5113, sixth focusing lens 5114, and seventh focusing lens 5115. The specimen or surface 5116 to be examined is not shown in FIG. 51, but is located to the right of the objective 5100 in the orientation shown in FIG. 51. Light energy strikes the specimen 5117 and reflects back through the objective 5100 of FIG. 51. Surface data for a system employing the design of FIG. 51 is listed in Table 3.

In a darkfield arrangement, light energy is directed toward the specimen surface as shown in FIG. 2. Light energy may scatter toward the objective, i.e. toward seventh focusing lens 5105 in the design of FIG. 51. In such an arrangement, light energy passes back through the system, striking the Mangin mirror 5107 and passing through first lens 5102. The design of FIG. 51 provides an optical system with an external pupil plane 5101 to support aperturing and Fourier filtering. An aperture can be used in connection with the FIG. 51 design to provide control of the numerical aperture of the imaging system. Such an aperture could be placed at the pupil plane hereby permitting control of overall resolution and depth of focus. Fourier filtering is very important for applications like laser dark field. Fourier filtering permits filtering surface patterns that repeat by increasing the signal-to-noise ratio for defects on the surface.

TABLE 3

Surface data for linear design shown in FIG. 51 at 193 nm with a 1 nm bandwidth

| Surf | Radius | Thickness | Material | Element Number |
|---|---|---|---|---|
| OBJ | Infinity | Infinity | | N/S |
| STO | Infinity | 25.000 | | 5101 |
| 2 | −222.386 | 4.000 | Silica | 5102 |
| 3 | −28.670 | 40.503 | | 5102 |
| 4 | 39.160 | 2.500 | Silica | 5103 |
| 5 | 177.023 | 10.000 | Silica | 5103 |
| 6 | Infinity | 0.000 | Mirror | 5104 |
| 7 | Infinity | −98.015 | | 5104 |
| 8 | −320.423 | −6.000 | Silica | 5105 |
| 9 | 149.893 | −142.852 | | 5105 |
| 10 | 58.250 | −8.000 | Silica | 5106 |
| 11 | 210.014 | −20.290 | | 5106 |
| 12 | 41.193 | −9.000 | Silica | 5107 |
| 13 | 81.848 | 9.000 | Mirror | 5107 |
| 14 | 41.193 | 20.290 | | 5107 |
| 15 | 210.014 | 8.000 | Silica | 5106 |
| 16 | 58.250 | 142.852 | | 5106 |
| 17 | 149.893 | 6.000 | Silica | 5105 |
| 18 | −320.423 | 98.015 | | 5105 |
| 19 | Infinity | 44.416 | | 5105 |
| 20 | 70.917 | 15.000 | Silica | 5108 |
| 21 | 48.487 | 83.467 | | 5108 |
| 22 | 326.205 | 11.000 | Silica | 5109 |
| 23 | −86.355 | 83.991 | | 5109 |
| 24 | 235.491 | 9.000 | Silica | 5110 |
| 25 | −111.089 | 10.357 | | 5110 |
| 26 | −58.901 | 4.000 | Silica | 5111 |
| 27 | −3728.698 | 89.493 | | 5111 |
| 28 | 45.959 | 6.365 | Silica | 5112 |
| 29 | 41.432 | 9.332 | | 5112 |
| 30 | −739.118 | 6.000 | Silica | 5113 |
| 31 | −79.014 | 1.000 | | 5113 |
| 32 | 44.790 | 9.000 | Silica | 5114 |
| 33 | 182.972 | 1.000 | | 5114 |
| 34 | 22.072 | 20.822 | Silica | 5115 |

TABLE 3-continued

Surface data for linear design shown in FIG. 51 at 193 nm with a 1 nm bandwidth

| Surf | Radius | Thickness | Material | Element Number |
|---|---|---|---|---|
| 35 | 36.911 | 11.529 | | 5115 |
| IMA | Infinity | | | N/S |

The sixth aspect of the DUV-VUV design presented in FIG. 52 is similar to the fifth aspect of FIG. 51, but has been optimized for a wavelength of 157 nm. The change in wavelength requires changing the material used from fused silica to calcium fluoride. The index of fused silica at a wavelength of 193 nm is nearly identical to the index for calcium fluoride at 157 nm, so the design requires no major changes aside from the material. However, the dispersion of calcium fluoride at 157 nm is larger than the dispersion of fused silica at 193 nm, which may require some minor changes to further optimize the design. The design presented in FIG. 52 also provides the option of splitting the Mangin mirror into a front surface mirror and a meniscus lens. This can simplify manufacturing in some cases. This approach can be used on the other catadioptric objective designs of FIGS. 47–52 as well. The object extends from 0.25 mm to 0.75 mm off axis and the design has a bandwidth of 0.5 nm from 156.75–157.25 nm.

As shown in FIG. 52, light energy or laser energy is transmitted from energy source 52000 (not shown) and into objective 5200. This objective 5200 also has an external pupil plane 5201 as in the design presented in FIG. 51. Objective 5200 includes first lens 5202 and first field lens 5203. This first field lens 5203 directs light energy to small folding mirror or reflecting surface 5204, which directs energy toward focusing lenses 5205, 5206, and 5207 and to mirror surface 5208. Light energy reflects back from mirror surface 5208 back through focusing lenses 5207, 5206, and 5205 and past small folding mirror or reflecting surface 5204. Light energy then passes through second field lens group 5220 which includes first field lens 5209, second fiend lens 5210, and third field lens 5211. Light then passes through focusing lens arrangement 5221, which includes first focusing lens 5212, second focusing lens 5213, third focusing lens 5214, fourth focusing lens 5215, fifth focusing lens 5216. The specimen or surface 5217 to be examined is not shown in FIG. 52, but is located to the right of the objective 5200 in the orientation shown in FIG. 52. Light energy strikes the specimen 5217 and reflects back through the objective 5200 of FIG. 52. Light from specimen 5217 can be apertured or Fourier filtered at pupil plane 5201 as described in the fifth aspect presented in FIG. 51.

The surface data for a system having the objective shown in FIG. 52 is listed in Table 4.

TABLE 4

Surface data for a linear design as shown in FIG. 52 at 157 nm with a 0.5 nm bandwidth

| Surf | Radius | Thickness | Material | Element Number |
|---|---|---|---|---|
| OBJ | Infinity | Infinity | | N/S |
| STO | Infinity | 25.000 | | 5201 |
| 2 | −228.090 | 4.000 | CaF$_2$ | 5202 |
| 3 | −26.271 | 34.743 | | 5202 |

TABLE 4-continued

Surface data for a linear design as shown in
FIG. 52 at 157 nm with a 0.5 nm bandwidth

| Surf | Radius | Thickness | Material | Element Number |
|---|---|---|---|---|
| 4 | 27.340 | 2.500 | CaF$_2$ | 5203 |
| 5 | 78.838 | 10.000 |  | 5203 |
| 6 | Infinity | 0 | Mirror | 5204 |
| 7 | Infinity | −75.368 |  | 5204 |
| 8 | 332.074 | −6.000 | CaF$_2$ | 5205 |
| 9 | 75.615 | −84.484 |  | 5205 |
| 10 | 53.058 | −7.000 | CaF$_2$ | 5206 |
| 11 | 129.105 | −12.000 |  | 5206 |
| 12 | 40.981 | −7.000 | CaF$_2$ | 5207 |
| 13 | 128.091 | −7.480 |  | 5207 |
| 14 | 69.614 | 7.480 | Mirror | 5208 |
| 15 | 128.091 | 7.000 | CaF$_2$ | 5207 |
| 16 | 40.981 | 12.000 |  | 5207 |
| 17 | 129.105 | 7.000 | CaF$_2$ | 5206 |
| 18 | 53.058 | 84.484 |  | 5206 |
| 19 | 75.615 | 6.000 | CaF$_2$ | 5205 |
| 20 | 332.074 | 75.368 |  | 5205 |
| 21 | Infinity | 39.173 |  |  |
| 22 | 24.018 | 15.000 | CaF$_2$ | 5209 |
| 23 | 26.501 | 24.354 |  | 5209 |
| 24 | −15.238 | 13.419 | CaF$_2$ | 5210 |
| 25 | −26.901 | 1.000 |  | 5210 |
| 26 | 355.973 | 7.000 | CaF$_2$ | 5211 |
| 27 | −56.508 | 110.232 |  | 5211 |
| 28 | 58.858 | 10.000 | CaF$_2$ | 5212 |
| 29 | 1338.307 | 6.0469 |  | 5212 |
| 30 | −54.890 | 10.000 | CaF$_2$ | 5213 |
| 31 | −72.556 | 26.319 |  | 5213 |
| 32 | −308.917 | 6.500 | CaF$_2$ | 5214 |
| 33 | −95.467 | 1.000 |  | 5214 |
| 34 | 34.0794 | 8.000 | CaF$_2$ | 5215 |
| 35 | 110.300 | 1.000 |  | 5215 |
| 36 | 16.407 | 9.697 | CaF$_2$ | 5216 |
| 37 | 29.683 | 11.927 |  | 5216 |
| IMA | Infinity |  |  |  |

Figure 53:
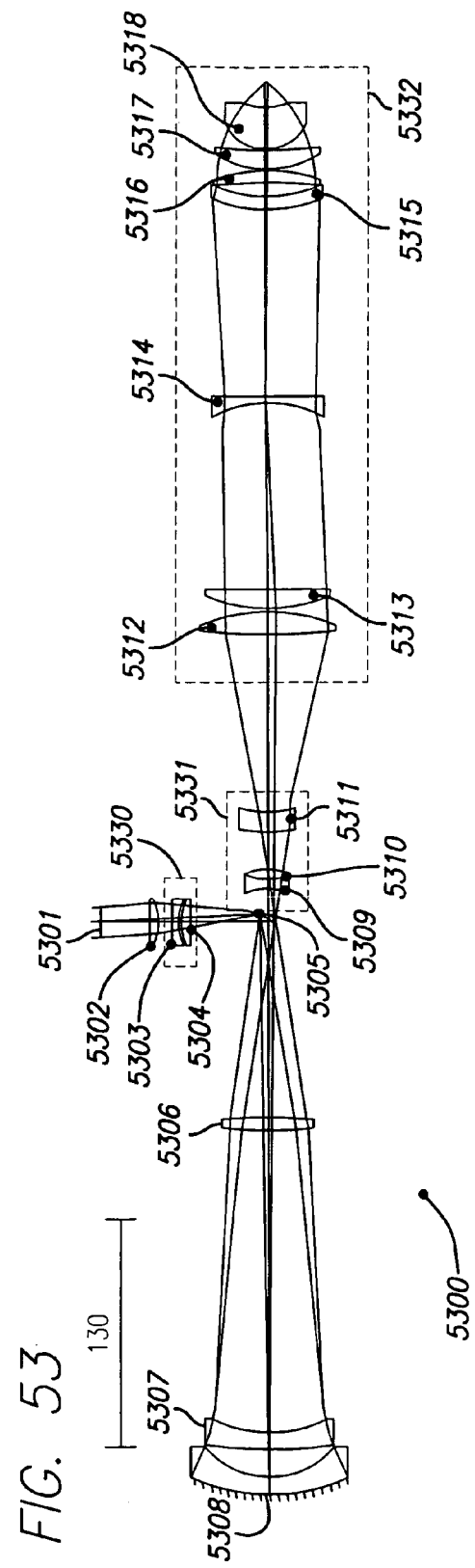
FIG. 53 presents an aspect of the system using two glass materials to increase the correction bandwidth from 193 to 203 nm.

The seventh aspect illustrated in FIG. 53 has similarities to the fifth and sixth aspects presented in FIGS. 51 and 52. The design presented in FIG. 53 uses the straight through 0.7 NA catadioptric approach to allow more design flexibility, improve performance, and relax the manufacturing tolerances. In addition, similar to the design of FIG. 50, a second glass material, calcium fluoride, is used to increase the correction bandwidth. The design of FIG. 53 is corrected from 193 to 203 nm. The FIG. 53 design has one calcium fluoride element in the eyepiece group and one calcium fluoride/silica doublet near the intermediate image. The object extends from 0.25 mm to 0.75 mm off axis and the design has a bandwidth from 193.3–203.3 nm.

As shown in FIG. 53, light energy or laser energy is transmitted from energy source 53000 (not shown) and into objective 5300. As in objective aspects presented in FIG. 51 and FIG. 52, an external pupil plane 5301 is available for aperturing and Fourier Filtering. Objective 5300 includes first lens 5302 and first field lens arrangement 5330, which includes first field lens 5303 and second field lens 5304. This first field lens arrangement 5330 directs light energy to small folding mirror or reflecting surface 5305, which reflects energy toward focusing lenses 5306 and 5307 and to Mangin mirror 5308. Light energy reflects back from Mangin mirror 5308 back through focusing lenses 5307 and 5306, and past small folding mirror or reflecting surface 5305. Light energy then passes through second field lens arrangement 5331, which includes third field lens 5309, fourth field lens 5310, and fifth field lens 5311. Light then passes through focusing lens arrangement 5332, which includes first focusing lens 5312, second focusing lens 5313, third focusing lens 5314, fourth focusing lens 5315, fifth focusing lens 5316, sixth focusing lens 5317, seventh focusing lens 5318. The specimen or surface 5319 to be examined is not shown in FIG. 53, but is located to the right of the objective 5300 in the orientation shown in FIG. 53. Light energy strikes the specimen 5317 and reflects back through the objective 5300 of FIG. 53.

The surface data for the design of FIG. 53 is listed in Table 5.

TABLE 5

Surface data for a linear design as in FIG.
53 at 193 nm with a 10 nm bandwidth

| Surf | Radius | Thickness | Material | Element Number |
|---|---|---|---|---|
| OBJ | Infinity | Infinity |  | N/S |
| STO | Infinity | 35.063 |  | 5301 |
| 2 | 527.763 | 4.000 | Silica | 5302 |
| 3 | −32.542 | 8.204 |  | 5302 |
| 4 | 572.044 | 2.000 | Silica | 5303 |
| 5 | 16.118 | 1.447 |  | 5303 |
| 6 | 17.545 | 5.000 | CaF2 | 5304 |
| 7 | −65.290 | 35.838 |  | 5304 |
| 8 | Infinity | 0.000 | Mirror | 5305 |
| 9 | Infinity | −96.873 |  | 5305 |
| 10 | −795.110 | −10.000 | Silica | 5306 |
| 11 | 92.663 | −199.957 |  | 5306 |
| 12 | 64.768 | −8.000 | Silica | 5307 |
| 13 | 281.874 | −14.019 |  | 5307 |
| 14 | 38.871 | −9.000 | Silica | 5308 |
| 15 | 80.841 | 9.000 | Mirror | 5308 |
| 16 | 38.871 | 14.019 |  | 5308 |
| 17 | 281.874 | 8.000 | Silica | 5307 |
| 18 | 64.768 | 199.957 |  | 5307 |
| 19 | 92.663 | 10.000 | Silica | 5306 |
| 20 | −795.110 | 96.873 |  | 5306 |
| 21 | Infinity | 9.399 |  | 5306 |
| 22 | −16.045 | 2.000 | Silica | 5309 |
| 23 | 24.034 | 0.217 |  | 5309 |
| 24 | 24.751 | 4.000 | CaF2 | 5310 |
| 25 | −16.515 | 22.166 |  | 5310 |
| 26 | 38.990 | 4.000 | Silica | 5311 |
| 27 | 41.231 | 164.091 |  | 5311 |
| 28 | 1232.004 | 10.000 | Silica | 5312 |
| 29 | −95.859 | 1.000 |  | 5312 |
| 30 | 79.148 | 9.000 | Silica | 5313 |
| 31 | −1367.718 | 33.541 |  | 5313 |
| 32 | −59.580 | 4.000 | Silica | 5314 |
| 33 | 201.391 | 45.680 |  | 5314 |
| 34 | 173.228 | 4.500 | Silica | 5315 |
| 35 | 58.668 | 7.500 |  | 5315 |
| 36 | −127.932 | 6.000 | Silica | 5316 |
| 37 | −41.246 | 1.000 |  | 5316 |
| 38 | 31.082 | 38.000 | Silica | 5317 |
| 39 | 153.068 | 1.000 |  | 5317 |
| 40 | 17.627 | 12.491 | Silica | 5318 |
| 41 | 35.390 | 11.566 |  | 5318 |
| IMA | Infinity |  |  |  |

A complete imaging system, such as presented in FIG. 57 and 46, requires an objective, such as presented in FIGS. 47–53, and image forming optics. The image forming optics can be many different designs. The image forming optics can be a static tube lens capable of producing a single magnification. In this case, different magnifications are achieved by using different tube lenses. This type of image forming optics can be designed by someone skilled in the art. Another type of image forming optics is a zooming tube lens. A zooming tube lens has the advantage that only a single optical system is required to produce a wide range of magnifications. Examples of two different types of zooming tube lenses will be presented in design aspects 7 and 8. It is important that the image forming optics are corrected for the wavelength and spectral bandwidth of the illumination source.

Figure 54:
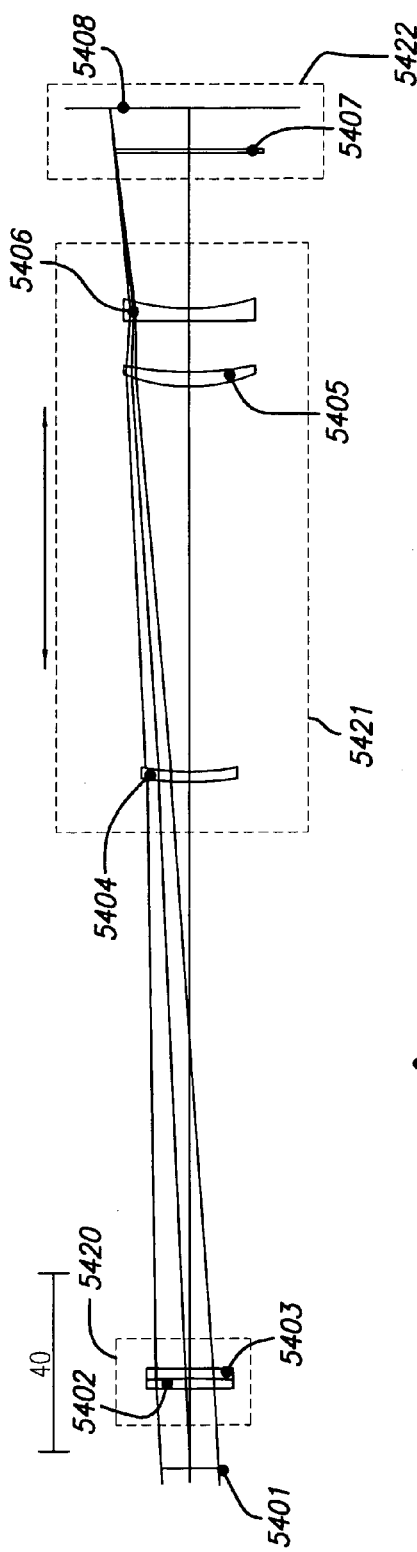
FIG. 54 presents an aspect of the image forming optics using a varifocal two motion zoom.
Figure 55:
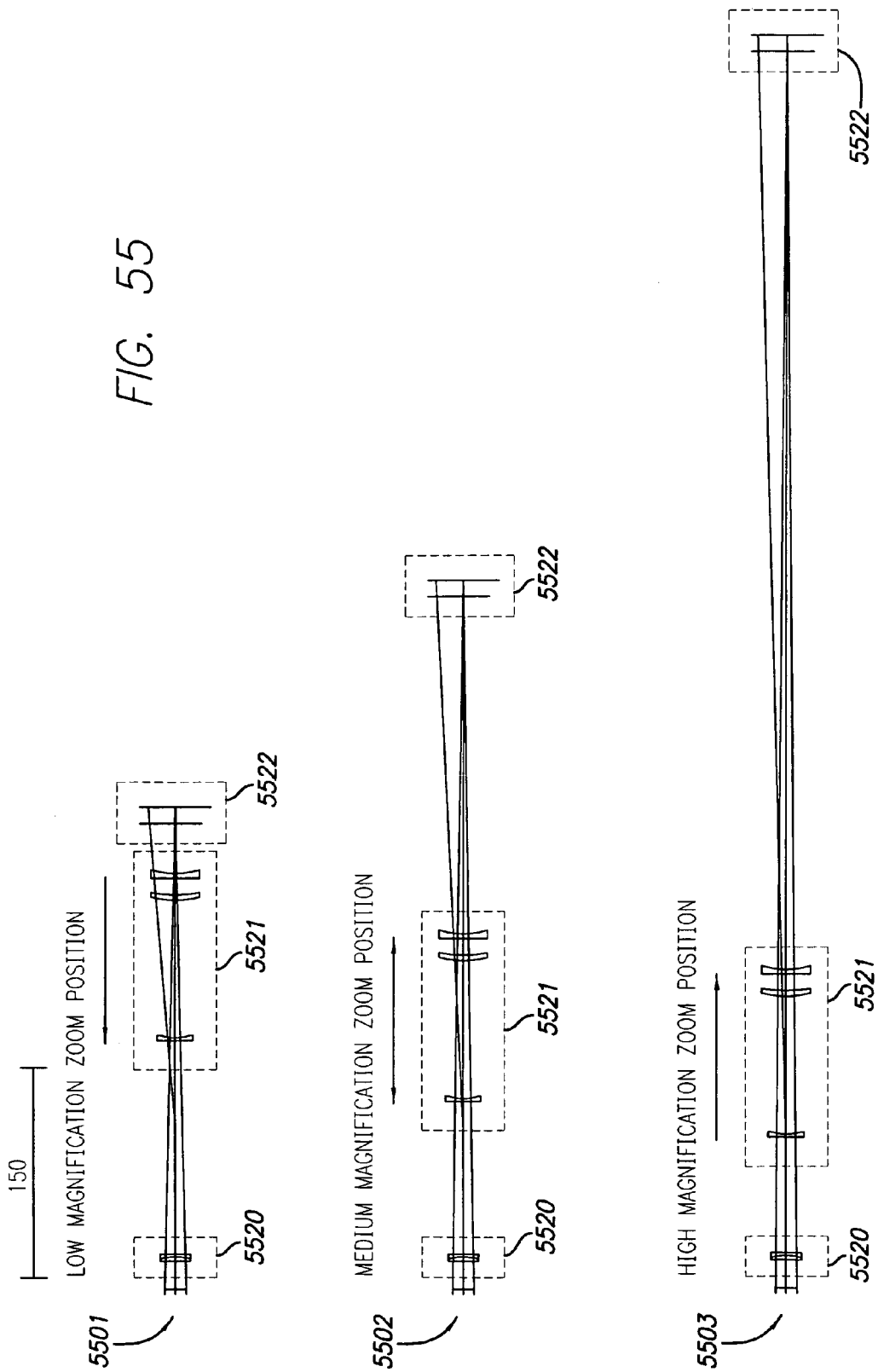
FIG. 55 presents three different magnifications possible with the varifocal zoom.

The seventh aspect illustrated in FIG. 54 is an image forming tube lens that uses a varifocal two motion zoom to change magnifications. The design methodology is similar to that presented above. The design comprises a stationary doublet 5420, a zooming group 5421, and a detector group 5422. The stationary doublet consists of a first doublet lens 5402 and a second doublet lens 5403. The zooming group consists of a first zoom lens 5404, a second zoom lens 5405, and a third zoom lens 5406. The detector group 5422 consists of a protective window 5407 and a detector 5408. Different magnifications are achieved by moving the zoom group along the optical axis and then moving the detector with the protective window to refocus. Three example magnifications are shown in FIG. 55. The low magnification zoom position 5501 has the shortest total length with the zoom group 5521 farthest away from the doublet 5520. For the medium magnification 5502 the total length from the doublet 5520 to the detector group 5522 increases and the distance from the doublet 5520 to the zoom group 5521 decreases. For the high magnification 5503 the maximum distance from the doublet 5520 to the detector group 5522 is achieved and the distance from the doublet 5520 to the zoom group 5521 is minimized. This design is capable of magnifications from 38 times to greater than 152 times. Over the magnification range from 38 times to 152 times, the total length of the system from the doublet 5520 to the detector 5508 changes from 320 mm to 880 mm. The three lenses that move in the zooming group 5521 move by 68 mm. The pupil 5501 of the design in FIG. 55 is matched to the design presented in FIG. 51. It is possible for someone skilled in the art, when presented with this disclosure, to design a similar tube lens for use with the objective designs presented in FIGS. 47–53 as well as other designs. The design of a varifocal two motion zoom with other magnifications and magnification ranges is also possible. The surface data for the design of FIG. 54 is listed in Table 6.

TABLE 6

Surface data for an image forming tube lens as in FIG. 54 at 193 nm with a 1.5 nm bandwidth

| Surf | Radius | Thickness | Glass | Surface number |
|---|---|---|---|---|
| OBJ | Infinity | Infinity | | N/S |
| STO | Infinity | 20.000 | | 5401 |
| 2 | 121.600 | 3.000 | Caf2 | 5402 |
| 3 | −77.915 | 0.500 | | 5402 |
| 4 | −78.860 | 2.000 | Silica | 5403 |
| 5 | −1820.981 | 90.732 | | 5403 |
| 6 | 106.439 | 2.500 | Caf2 | 5404 |
| 7 | 59.162 | 99.528 | | 5404 |
| 8 | 50.266 | 4.000 | Silica | 5405 |
| 9 | 124.701 | 14.006 | | 5405 |
| 10 | −687.986 | 3.000 | Caf2 | 5406 |
| 11 | 53.069 | 470.445 | | 5406 |
| 12 | Infinity | 1.000 | Silica | 5407 |
| 13 | Infinity | 1.000 | | 5407 |
| IMA | Infinity | | | 5408 |

Figure 56:
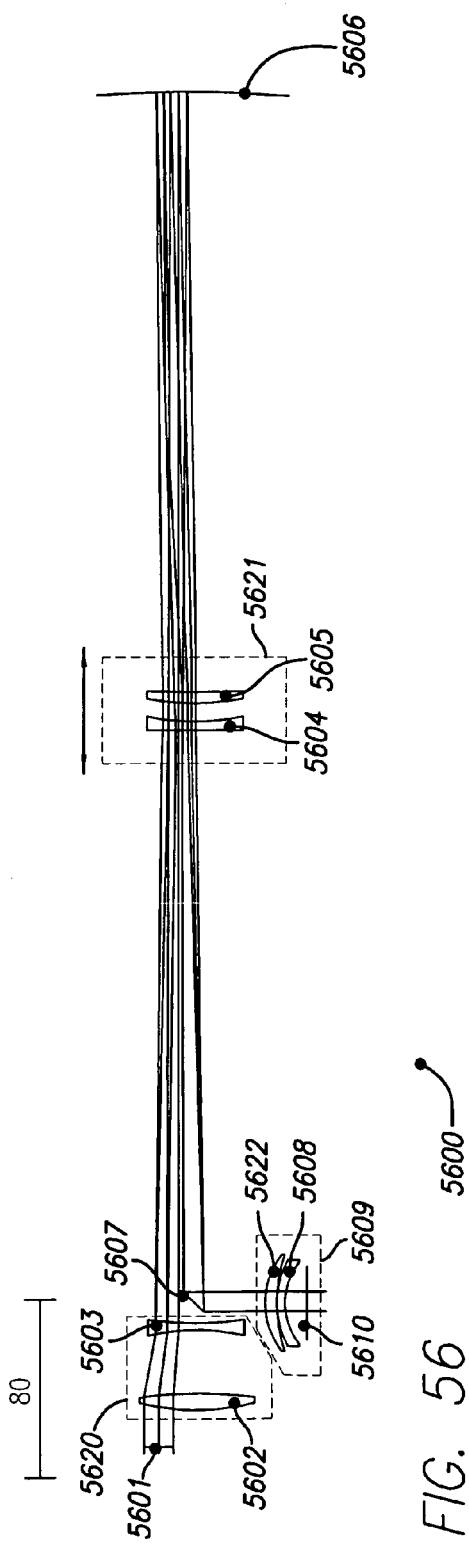
FIG. 56 presents an aspect of the image forming optics using a single motion optically compensated zoom.

The eighth aspect of the DUV/VUV design illustrated in FIG. 56 is an image forming tube lens that uses an optically compensated single motion zoom to change magnifications. The design methodology is similar to that in the paper by David R. Shafer, "Catadioptric optically compensated zooming system with one moving element" Proc SPIE Vol. 2539, p235–240. The design consists of a first doublet 5620, a zooming group 5621, a mirror 5606, a second doublet 5622, and a detector 5610. The first doublet consists of a doublet lens 5602 and a following doublet lens 5603. The zooming group consists of a first zoom lens 5604 and a second zoom lens 5605. Different magnifications are achieved by moving the zoom group 5621 along the optical axis of the first doublet 5620, the zoom group 5621, and the mirror 5606. No other motion is required. Three example magnifications are shown in FIG. 57. The low magnification zoom position 5701 has the zoom group 5721 very close to the first doublet 5720. For the medium magnification 5702, the zoom group is in between the first doublet 5720 and the mirror 5704. For the high magnification 5703 the zoom group 5721 is very close to the mirror 5704. The design is capable of magnifications from 60 times to greater than 180 times. The pupil 5601 of the design in FIG. 56 is matched to The design presented in FIG. 51. It is possible for someone skilled in the art, when presented with this disclosure, to design a similar tube lens for use with the objective designs presented in FIGS. 47–53 as well as other designs. It is also possible for someone skilled in the art, when presented with this disclosure, to design an optically compensated single motion zoom with other magnifications and magnification ranges. The surface data for the design of FIG. 56 is listed in Table 7.

TABLE 7

Surface data for an image forming tube lens as in FIG. 56 at 193 nm with a 1.5 nm bandwidth

| Surf | Radius | Thickness | Glass | Surface number |
|---|---|---|---|---|
| OBJ | Infinity | Infinity | | N/S |
| STO | Infinity | 20.000 | | 5601 |
| 2 | — | 0.000 | — | N/S |
| 3 | 123.897 | 8.000 | caf2 | 5602 |
| 4 | −213.430 | 33.518 | | 5602 |
| 5 | −119.986 | 4.000 | silica | 5603 |
| 6 | 206.676 | 315.675 | | 5603 |
| 7 | 24267.100 | 4.000 | caf2 | 5604 |
| 8 | 117.959 | 10.577 | | 5604 |
| 9 | 125.844 | 5.000 | silica | 5605 |
| 10 | 325.138 | 319.238 | | 5605 |
| 11 | −1125.668 | −319.238 | MIRROR | 5606 |
| 12 | 325.138 | −5.000 | silica | 5605 |
| 13 | 125.844 | −10.577 | | 5605 |
| 14 | 117.959 | −4.000 | caf2 | 5604 |
| 15 | 24267.100 | −305.678 | | 5604 |
| 16 | — | 0.000 | — | N/S |
| 17 | Infinity | 0.000 | MIRROR | 5607 |
| 18 | — | 0.000 | — | N/S |
| 19 | Infinity | 36.000 | | N/S |
| 20 | 39.403 | 6.000 | silica | 5608 |
| 21 | 81.584 | 0.500 | | 5608 |
| 22 | 50.614 | 4.000 | silica | 5609 |
| 23 | 33.375 | 11.140 | | 5609 |
| IMA | Infinity | | | 5610 |

Autofocus

As the semiconductor device moves during high speed inspection, minute changes in the focus position must be corrected. Thus such a system may be served by employing automatic focusing to maintain a high fidelity image.

The present system may employ an autofocus subsystem in connection with the positioning subsystem to automatically focus the light energy received from the illumination subsystem. Many different types of automatic focusing subsystems have been successfully applied to semiconductor inspection. These automatic focusing subsystems consist of detecting a focus change, focusing the wafer or photomask, and using feedback to maintain the desired focus position.

Various techniques exist for detecting a focus change. One such method described in U.S. Pat. No. 4,639,587, assigned to KLA Instruments, the assignee of the present invention and hereby incorporated by reference, describes an automatic focusing system that uses the comparison of two masks and is used primarily for semiconductor wafer inspection. This technique has the advantage that it can be used to measure the focus position of a wafer containing a partially fabricated integrated circuit. Measuring the best focus position on a wafer containing a partially fabricated integrated circuit is complicated by the fact there may be multiple layers with complex geometries with varying reflectivities. The desired focus position is usually the top most layer of the wafer. However separating an actual focus change from a change in the circuit patterns can be a difficult task. This technique produces a best focus location that is an average of the different levels on the wafer multiplied by the reflected signal. Focus location and correction is less of an issue at short wavelengths where materials may be more strongly absorbing.

Another method of automatic focus involves astigmatic focusing on a quadrant detector. The astigmatic focusing technique is commonly used in photomask inspection and in Compact Disc readers and writers. In this method, light from an illumination source is focused on the sample surface, typically through the imaging subsystem optics. The reflected light, typically collected by the imaging subsystem optics, is then focused by an astigmatic lens onto a quadrant detector. As the sample is moved through focus, the shape of the focus changes and is measured by the quadrant detector. This astigmatic focusing technique typically works effectively for samples with limited topology variations.

The pulsed nature of the excimer laser can complicate the automatic focusing method if pulsed light from the excimer laser is used for the focusing. This may allow the focus position of the sample to be measured during each pulse, which may be adequate on a sample with minimal topology variations or very high precision stage. To address this issue, one option is to use a continuous or nearly continuous energy source to maintain focus when the specimen is not illuminated by pulsed light.

The method for detecting the focus change must also account for separation of the automatic focusing signal from the image in the imaging subsystem. Both variable wavelength and different field aspects may be incorporated. If a different wavelength is used between the autofocus and the imaging subsystems, a dichroic device such as a beamsplitter or grating may be used to separate the signals. If a slightly different position on the sample is used for the autofocus and imaging subsystems, the signals can be separated at an internal field plane within the imaging subsystem or at the final image plane. In this case, the same illumination source can be used for the illumination and autofocus subsystems.

Several methods can be used to focus the semiconductor device. Moving the semiconductor device itself to maintain focus is typically done during wafer inspection. Moving the objective to maintain focus is typically performed for photomask inspection. For transmitted light, the condenser focusing the light on the photomask may also be moved. For large high precision optical systems such as previously described, it may not be feasible to move the objective for focusing. In this situation, one or more of the optical elements in the imaging subsystem may be used to compensate for focus changes. Preferable performance may result when focusing does not greatly affect the magnification or telecentricity of the imaging subsystem.

Feedback control may be employed to maintain the proper focusing. The feedback control may take into account the resonance of the different autofocus mechanical and electronic components and minimize overshoot and ringing. Such feedback controls are used in autofocus systems for semiconductor inspection, compact disc players, and other high precision optical devices. The particular feedback loop parameters, such as those used in a Proportional Integral Derivative (PID) loop controller, and are specific to the autofocus subsystem design.

Sensor

One type of sensor that may be employed in the present system is back thinned silicon. A back thinned silicon sensor has high speed with low noise readout, high quantum efficiency, long lifetimes, and high MTF. Many other types of sensors may be employed, including but not limited to front side devices with open silicon areas, lumogen coated front side sensors, photo-diamond sensors, and silicon carbide sensors. Photo-diamond type and silicon carbide type sensors tend to have very little sensitivity to visible wavelengths.

These sensor types can be operated in different modes including frame transfer and time delay and integration (TDI). The frame transfer mode is useful for an inspection system using a single excimer laser pulse to illuminate an area on the sample. Each pulse generally corresponds to one frame of the sensor. This has the advantage that two halves of the detector can be read out simultaneously for increased data rates. If multiple pulses from the excimer laser are used to expose a single area on the sample, a TDI mode sensor can be used. In special inspection modes, such as the confocal and dark field inspection modes, single point detectors or arrays of single point detectors may also be used.

The system performs a high speed sample inspection with high resolution. For example an inspection system with a pixel size of 50 nm would require a data rate of 1.1 Gpixels/second to scan an area of 10 cm×10 cm in one hour. Increasing the inspection speed tends to reduce the per-sample cost of an inspection system. The sensor may also have very low noise at these high data rates. For example less than 1 count of noise out of 256 counts of signal. Often less than 1 count of noise out of 1024 counts of signal is required. To obtain low noise is an extremely complex issue that involves careful design of the sensor layout, amplifier, packaging, and readout electronics by one skilled in the art. The electrical design of each of these is critical to minimize the effects of crosstalk, feedthrough and adequately isolate the ground. The sensor subsystem also has high quantum efficiency, long lifetimes, and a high contrast transfer function. High quantum efficiencies generally require less light from the illumination system to fully expose the sensor. In this scenario, a smaller excimer laser can be used for the illumination subsystem. A smaller laser can have longer lifetimes. Higher quantum efficiency also means less energy is required on the sample surface, thus tending to limit the potential for damage from the high peak powers of an excimer laser pulse. Long lifetimes minimize the possibility that the sensor performance changes with time, decreasing the risk of system recalibration. Typical performance changes with excimer laser exposure are an increase in dark current and a decrease in quantum efficiency. If these changes are too large, the sensor may be out of range for recalibration and have to be replaced. A high Contrast Transfer Function (CTF) is required to detect the image with adequate resolution. If the imaging subsystem produces a very high resolution image, the inspection system will not be able to detect the high resolution image if the sensor has a low CTF. A CTF generally as low as approximately 0.4 is acceptable for an inspection system, however a value of 0.6 or greater may be employed with acceptable results in certain conditions.

The sensor employed in the present system may be a single point diode type detector or an area type detector such as a CCD or a CCD operating in the Time Delay and Integration (TDI) mode. This sensor may have a high quantum efficiency, low noise, and a good Modulation Transfer Function (MTF). Back thinned CCD sensors can be used for this purpose.

One possible sensor that may be employed in the current design is presented in U.S. Pat. No. 4,877,326, entitled "Method and Apparatus for Optical Inspection of Substrates," assigned to the assignee of the present application, the entirety of which is incorporated herein by reference.

The sensor may be back illuminated or front illuminated, where front illumination may include virtual phase design, solid state, with open areas to be UV sensitive, and may incorporate sensors with florescent coatings. The system may be a point, line, 2D, multitap readout, linear, photodiode array, CCD, or split readout to double the speed. The sensor may be a diamond based sensor, and may have antiblooming capability. The sensor may be staggered or comprise multiple sensors in one package. Sensor electronics may provide for exposure correction. Adjacent images or total power may be viewed by the sensor and sensor readings may be used to correct long term drift in the laser or correct jitter.

The sensor employed may include aspects of high quantum efficiency at the excimer laser wavelength. Back thinned silicon sensors may be employed to offer adequate performance. The sensor further may have high resolution capabilities to support high resolution imaging, high speed capability to support high speed inspection, and low noise and high dynamic range to support the various defect detection modes contemplated herein.

Data Acquisition

The data acquisition subsystem for the current system includes frame mode operation and TDI mode operation. When operating in frame mode, only a single laser pulse exposes a frame as the positioning stage scans. In this mode, the effects of stage vibration are reduced by virtue of the short exposure pulse, and improved sensor MTF over a sensor, such as a TDI sensor. TDI mode entails integrating multiple excimer laser pulses. This helps improve speckle smoothing and reduce peak powers as described in the illumination subsystem.

The data acquisition subsystem can use a single sensor, which may have a large area for sensing in accordance with the description above. The sensor may fill the imaging field of view to maximize the available area and decrease peak powers.

Multiple sensors may also be employed to reduce the overall cost of the sensor, as use of more small sensors is typically less than use of one large sensor of similar area. These sensors may be located in relatively close proximity. They can be mounted on the same electronics board and even butted together effectively producing a larger sensor. The sensors can also be spatially separated from each other. This can have an advantage because it may be difficult to pack all the readout electronics near the location of the sensor. The field if the imaging subsystem can be split into multiple parts using a scraping mirror, beam splitter, prism, grating, or diffractive optic. Each part can then be sent to one sensor. Ideally, the splitting is done at a field plane so the impact on the image fidelity is minimized. It is also possible to locate the sensors at different focal positions to gather in and out of focus data simultaneously. It is also possible to have different imaging modes on the different sensors to simultaneously gather defect data. For example, bright field and dark field data could be gathered simultaneously to look for different types of defects.

Additional difficulties arise using high speed sensors in the presence of an excimer laser. The sensor readout and excimer laser may be synchronized, usually with the sample being inspected.

Synchronization entails matching the timing of the excimer laser pulsing, the sensor readout, and the desired location of the positioning stage to each other. Typically, one of these devices is used as a reference and the others are synchronized to it. One such method uses a sensor and laser that are synchronized to the positioning subsystem. Synchronization of the sensor readout, positioning stage, and laser occur by the stage producing a timing signal.

An additional method may use a sensor and positioning subsystem synchronized to the laser. A further method would allow the laser and positioning subsystem to be synchronized to the sensor.

Data acquisition can occur as the stage accelerates and decelerates, but the synchronzation between the elements provides the improved characteristics of data acquisition for the design.

For an excimer laser, the first few pulses received after the laser has not been pulsing may be unstable and can be discarded. This will reduce the dynamic range over which the exposure must be corrected. The system may also include selectable frequency, pulse skipping, and adjustable power. To optimize the sensor exposure during the scanning of the positioning stage.

Data Analysis

The purpose of the data analysis subsystem is to identify yield limiting defects on a sample. Defects are primarily identified using comparison techniques. One comparison technique used for wafer and photomask inspection uses the comparison of different dies. For example, if dies 1 and 2 are compared and a difference is found at location A and dies 2 and 3 are compared and a difference is also found at location A, the defect at location a is attributed to die 2.

Another technique uses a comparison between different cells within a die. A cell is defined such that it repeats many times within the inspection area of interest. This type of comparison is useful for memory, and logic areas within a die. It is often desired to have an adjustable magnification in the imaging subsystem to each cell can be adjusted to an integral number of sensor pixels.

A third comparison technique is die-to-database comparison. This is useful for inspecting photomasks because they are relatively simple structures and their desired patterns are precisely known in an electronic format or database. In order to compare data from the inspection system to the database, the database must be rendered by taking into account the performance of the imaging and sensor subsystems and their effect on the database. This rendered database can then be compared to the data gathered by the inspection system. It is also possible to take inspection data and render it to the database for comparison, however this can be more difficult. It has its main advantage for the aerial imaging inspection mode. Aerial imaging is complicated by the fact that the errors in the mask must be inferred from the measured data. Compensation may also be done for field aberrations like distortion.

The data is acquired in a frame-by-frame basis. Each frame can come from a single excimer laser pulse or multiple excimer laser pulses. Each frame can be allowed to slightly overlap with the previous and subsequent frames so no data is lost. This overlapping region can also be used for accurately aligning the frames.

Alignment of the comparison data is a major challenge for data analysis. It is often desirable for the data being compared to contain an integer number of pixels. It can also be desirable for some frames of data to begin at known locations to simplify comparison. For example, in die-to-die comparison, it simplifies the computation if the beginning of each die is in the same location within a frame. This can be accomplished by accurately adjusting the timing of the acquisition system and adjusting the frame overlap a desired amount so the beginning on a first die and the beginning of a second die are located at the same position within a frame.

It may also be desirable to have an auxiliary light source that can be used for frame alignment. This light source can be continuous and the frame alignment and timing checked prior to the arrival of the excimer pulse. Any variation in the desired position can be compensated for by adjusting the timing of the excimer laser pulse.

The defect data can then be sent to other systems for further analysis such as e-beam review, macro review, or focused ion beam destructive analysis. The data can also be sent to yield management software for use in fab wide yield improvement.

While the invention has been described in connection with specific embodiments thereof, it will be understood that the invention is capable of further modifications. This application is intended to cover any variations, uses or adaptations of the invention following, in general, the principles of the invention, and including such departures from the present disclosure as come within known and customary practice within the art to which the invention pertains.

What is claimed is:

1. A system for inspecting a specimen comprising:
an illumination subsystem comprising a relatively low coherence excimer laser for directing low coherence light energy toward said specimen wherein light energy originating from said excimer laser is generated using a plurality of gasses within the excimer laser and light energy originating from said excimer laser is provided to said specimen using a numerical aperture in excess of approximately 0.90; and
a sensor subsystem for receiving light energy reflected from said specimen;
wherein said sensor subsystem comprises a silicon sensor and said specimen comprises a semiconductor specimen.

2. The system of claim 1 where the silicon sensor comprises a back thinned sensor.

3. The system of claim 2 where the silicon sensor is operated in a predetermined sensing mode.

4. The system of claim 1 where the silicon sensor has anti-blooming capability.

5. A system for inspecting a specimen comprising:
an illumination subsystem comprising a relatively low coherence excimer laser for directing low coherence light energy toward said specimen, said excimer laser generating the light energy from a plurality of gasses within a cavity of said excimer laser and said cavity comprising at least one dispersive component configured to narrow transmittal bandwidths of the light energy; and
a sensor subsystem for receiving light energy reflected from said specimen.

6. A system for inspecting a specimen comprising:
an illumination subsystem comprising a low coherence-excimer laser for directing low coherence light energy toward said specimen, said excimer laser comprising a cavity comprising at least one dispersive component configured to narrow transmittal bandwidths of the light energy and at least one curved reflective surface configured to reduce spatial coherence of the light energy; and
a sensor subsystem for receiving light energy reflected from said specimen.

7. A system for inspecting a specimen comprising:
an illumination subsystem comprising a reduced coherence excimer laser comprising a cavity comprising at least one curved reflective surface configured to reduce spatial coherence of the excimer laser, said excimer laser configured to direct low coherence light energy toward said specimen using a numerical aperture in excess of approximately 0.65;
a sensor subsystem comprising a detector for detecting reflected light energy received from said specimen; and
a data analysis subsystem receiving image data from said sensor and using image comparisons to identify defects on said specimen.

8. The system of claim 7 where the comparison is a die-to-die comparison.

9. The system of claim 8 where any frame overlap is adjusted in the data analysis subsystem to align a portion of one die with a particular pixel in the sensor subsystem.

10. The system of claim 7 where the comparison system is a cell-to-cell comparison.

11. The system of claim 7 where the comparison is a die-to-database comparison.

12. The system of claim 11 where the database is rendered to an image for comparison.

13. The system of claim 11 where the image is rendered to a database for comparison.

14. A system for inspecting a specimen comprising:
an illumination subsystem comprising a relatively low coherence excimer laser transmitting low coherence light energy toward said specimen, said excimer laser comprising a cavity employing at least one dispersive component configured to narrow transmission bandwidth of the light energy transmitted toward the specimen;
a sensing subsystem for sensing light energy received from said specimen, said sensor subsystem producing a sensor readout; and
a data acquisition subsystem that synchronizes the excimer laser to the sensor readout.

15. The system of claim 14, further comprising an imaging subsystem between said illuminating subsystem and said specimen, wherein the data acquisition subsystem employs at least one sensor within the imaging subsystem field of view.

16. The system of claim 14, further comprising an imaging subsystem between said illuminating subsystem and said specimen, wherein the data acquisition subsystem that employs a plurality of sensors within the imaging subsystem field of view.

17. A system for inspecting a specimen comprising:
an illumination subsystem comprising a relatively low coherence excimer laser and at least one catadioptric element, said illumination subsystem employed to transmit low coherence light energy toward the specimen, said excimer laser comprising a cavity employing at least one dispersive component configured to narrow transmission bandwidth of the light energy transmitted toward the specimen;
a positioning subsystem for positioning the specimen in a desired orientation, the positioning subsystem comprising a positioning stage;
a sensing subsystem for sensing low coherence light energy received from said specimen, said sensor subsystem producing a sensor readout; and
a data acquisition subsystem that synchronizes the sensor readout to the positioning stage.

18. The system of claim 17, further comprising an imaging subsystem between said illuminating subsystem and said specimen, wherein the data acquisition subsystem employs at least one sensor within the imaging subsystem field of view.

19. The system of claim 17, further comprising an imaging subsystem between said illuminating subsystem and said specimen, wherein the data acquisition subsystem that employs a plurality of sensors within the imaging subsystem field of view.

20. A system for inspecting a specimen comprising:
an illumination subsystem comprising a relatively low coherence excimer laser configured to direct low coherence light energy toward the specimen;
a sensing subsystem for sensing light energy received from said specimen, said sensor subsystem producing a sensor readout; and
a data acquisition subsystem that synchronizes the sensor readout to the excimer laser.

21. The system of claim 20, further comprising an imaging subsystem between said illuminating subsystem and said specimen, wherein the data acquisition subsystem employs at least one sensor within the imaging subsystem field of view.

22. The system of claim 20, further comprising an imaging subsystem between said illuminating subsystem and said specimen, wherein the data acquisition subsystem that employs a plurality of sensors within the imaging subsystem field of view.

23. The system of claim 21 where each sensor is located proximate within a field of view of the imaging subsystem.

24. The system of claim 23 wherein each sensor is physically spaced from any other sensor; and
an imaging subsystem field comprises a plurality of portions and each portion of the field is sent to a different sensor.

25. A method of inspecting a specimen, comprising:
illuminating at least a portion of said specimen using a relatively low coherence excimer source using at least one relatively intense wavelength, said illuminating occurring at a numerical aperture in excess of approximately 0.97;
detecting radiation received from said illuminated portion of said specimen;
analyzing said detected radiation to view potential defects present in said portion of said specimen; and
exposing at least a portion of said specimen to a second, relatively weak wavelength from said excimer source.

26. The method of claim 25, wherein said relatively weak wavelength is used to assist in focusing said specimen to a desired location on said specimen.

27. A method of inspecting a specimen, comprising:
illuminating at least a portion of said specimen using a relatively low coherence excimer source using at least one relatively intense wavelength from said source, said illuminating occurring at a numerical aperture in excess of approximately 0.97;
detecting radiation received from said illuminated portion of said specimen;
analyzing said detected radiation to view potential defects present in said portion of said specimen; and
exposing at least a portion of said specimen to a second, relatively weak wavelength without concurrently exposing said portion to said relatively intense wavelength, wherein said relatively weak wavelength may be used to assist in focusing said specimen.

28. A method of inspecting a specimen, comprising:
illuminating at least a portion of said specimen using a relatively low coherence excimer source;
detecting radiation received from said illuminated portion of said specimen;
analyzing said detected radiation to detect potential defects present in said portion of said specimen; and
monitoring the dose of excimer radiation to which said portion of said specimen is exposed;
wherein illumination of said portion is discontinued once a predetermined dose limit is reached.

29. The method of claim 28, wherein said illumination is terminated automatically upon reaching the predetermined dose limit.

30. The method of claim 28, wherein data concerning exposure dose as a function of position is maintained for said specimen.

31. The method of claim 30, wherein said data is stored and used to limit overexposure of said specimen during subsequent processing steps.

32. The method of claim 31, wherein said data is stored in an open format accessible by a plurality of process tools.

33. A method of inspecting a specimen, comprising:
illuminating at least a portion of said specimen using a relatively low coherence excimer source using at least one relatively intense wavelength from said source, said illuminating occurring at a numerical aperture in excess of approximately 0.97;
detecting radiation received from said illuminated portion of said specimen; and
exposing at least a portion of said specimen to a second, relatively weak wavelength from said excimer source.

34. The method of claim 33, further comprising analyzing said detected radiation to view potential defects present in said portion of said specimen subsequent to said detecting.

35. The method of claim 33, wherein said relatively weak wavelength is used to assist in focusing a desired location on said specimen.

36. A method of inspecting a specimen, comprising:
illuminating at least a portion of said specimen using a relatively low coherence excimer source using at least one relatively intense wavelength from said source;
detecting radiation received from said illuminated portion of said specimen; and
exposing at least a portion of said specimen to a second, relatively weak wavelength without concurrently exposing said portion to said relatively intense wavelength, wherein exposing said portion to said relatively weak wavelength assists in navigating to a desired location on said specimen.

37. The method of claim 36, further comprising:

analyzing said detected radiation to view potential defects present in said portion of said specimen prior to said exposing.

38. An apparatus for inspecting a specimen, comprising:

an illuminator configured to illuminate at least a portion of said specimen using a relatively low coherence excimer source;

a detector configured to detect radiation received from said illuminated portion of said specimen; and a monitor configured to monitor a dose of excimer radiation to which said portion of said specimen is exposed;

wherein said illuminator discontinues illumination of said portion once a predetermined dose limit is reached.

39. The apparatus of claim 38, further comprising means for analyzing said detected radiation to detect potential defects present in said portion of said specimen subsequent to said detecting.

40. The apparatus of claim 38, wherein said illuminator discontinues illumination based on data received from said monitor.

41. The apparatus of claim 38, wherein said illumination is terminated automatically upon reaching the predetermined dose limit.

42. The apparatus of claim 38, wherein data concerning exposure dose as a function of position is maintained for said specimen.

43. The apparatus of claim 42, wherein said data is stored and used to limit overexposure of said specimen during subsequent processing.

44. The apparatus of claim 43, wherein said data is stored in an open format accessible by a plurality of process tools.

* * * * *